US010329550B2

(12) United States Patent
Briers et al.

(10) Patent No.: US 10,329,550 B2
(45) Date of Patent: Jun. 25, 2019

(54) ANTIMICROBIAL AGENTS

(71) Applicant: Lysando AG, Triesenberg (LI)

(72) Inventors: Yves Briers, Nederokkerzeel (BE); Rob Lavigne, Ekeren (BE); Martin Griessl, Forchheim (DE)

(73) Assignee: LYSANDO AG, Triesenberg (LI)

( * ) Notice: Subject to any disclaimer, the term of this patent is extended or adjusted under 35 U.S.C. 154(b) by 23 days.

(21) Appl. No.: 15/118,775

(22) PCT Filed: Feb. 13, 2015

(86) PCT No.: PCT/EP2015/053150
§ 371 (c)(1),
(2) Date: Aug. 12, 2016

(87) PCT Pub. No.: WO2015/121443
PCT Pub. Date: Aug. 20, 2015

(65) Prior Publication Data
US 2017/0051266 A1     Feb. 23, 2017

(51) Int. Cl.
| | | |
|---|---|---|
| *C12N 9/36* | (2006.01) | |
| *C12N 9/80* | (2006.01) | |
| *A01N 37/18* | (2006.01) | |
| *A23L 33/18* | (2016.01) | |
| *A61K 38/00* | (2006.01) | |
| *C07K 14/46* | (2006.01) | |
| *C07K 14/47* | (2006.01) | |
| *C12N 15/62* | (2006.01) | |
| *A23K 20/147* | (2016.01) | |
| *C07K 14/435* | (2006.01) | |

(52) U.S. Cl.
CPC .......... *C12N 9/2462* (2013.01); *A01N 37/18* (2013.01); *A23K 20/147* (2016.05); *A23L 33/18* (2016.08); *C07K 14/43563* (2013.01); *C07K 14/43572* (2013.01); *C07K 14/43577* (2013.01); *C07K 14/461* (2013.01); *C07K 14/47* (2013.01); *C12N 9/80* (2013.01); *C12N 15/62* (2013.01); *C12Y 302/01017* (2013.01); *C12Y 305/01028* (2013.01); *A23V 2002/00* (2013.01); *A61K 38/00* (2013.01); *C07K 2319/00* (2013.01); *C07K 2319/55* (2013.01); *C07K 2319/95* (2013.01)

(58) Field of Classification Search
None
See application file for complete search history.

(56) References Cited

FOREIGN PATENT DOCUMENTS

| | | |
|---|---|---|
| WO | WO 2010/023207 | 3/2010 |
| WO | WO 2010/149792 | 12/2010 |
| WO | WO 2010/149795 | 12/2010 |
| WO | WO 2011/023702 | 3/2011 |
| WO | WO 2011/134998 | 11/2011 |
| WO | WO 2012/059545 | 5/2012 |
| WO | WO 2012/085259 | 6/2012 |

OTHER PUBLICATIONS

UniProt sequence, A0A1421F03_9CAUD (integrated into UniProt/TrEMBL Jun. 8, 2016), (Year: 2016).*
"Putative endolysin", Database UniProt, Accession No. D6RR13, dated Aug. 10, 2010.
Cheng et al., "Removal of group B *Streptococci* colonizing the vagina and oropharynx of mice with a bacteriophage lytic enzyme", *Antimicrobial agents and chemotherapy*, 49(1): 111-117, 2005.
International Search Report and Written Opinion issued in International Application No. PCT/EP2015/053150, dated Apr. 21, 2015.
Loeffler et al., "Rapid killing of *Streptococcus pneumoniae* with a bacteriophage cell wall hydrolase", *Science* 294(5549): 2170-2, 2001.
Nelson et al., "Prevention and elimination of upper respiratory colonization of mice by group A *Streptococci* by using a bacteriophage lytic enzyme", *Proceedings of the National Academy of Sciences* 98(7): 4107-4112, 2001.
Rashel et al., "Efficient elimination of multidrug-resistant *Staphylococcus aureus* by cloned lysin derived from bacteriophage φMR11", *Journal of Infectious Diseases* 196(8): 1237-1247, 2007.
Schuch et al., "A bacteriolytic agent that detects and kills *Bacillus anthracis*"*Nature* 418(6900): 884-9, 2002.

* cited by examiner

*Primary Examiner* — Jennifer Pitrak McDonald
*Assistant Examiner* — Tara L Martinez
(74) *Attorney, Agent, or Firm* — Parker Highlander PLLC

(57) ABSTRACT

The present invention relates to polypeptides comprising an amino sequence selected from the group consisting of: SEQ ID NO: 1, and fragments and derivatives of these. The invention also relates to the corresponding nucleic acids vectors, host cells and compositions. The present inventions also relates to the use of said polypeptides, nucleic acids, vectors, host cells and compositions in a method for treatment of the human or animal body by surgery or therapy or in diagnostic methods practiced on the human or animal body, in particular for the treatment or prevention of Gram-negative bacterial infections. The polypeptides, nucleic acids, vectors, host cells and compositions according to the invention may also be used as an antimicrobial in food or feed, or in cosmetics, as disinfecting agent or in the environmental field.

Figure 1:
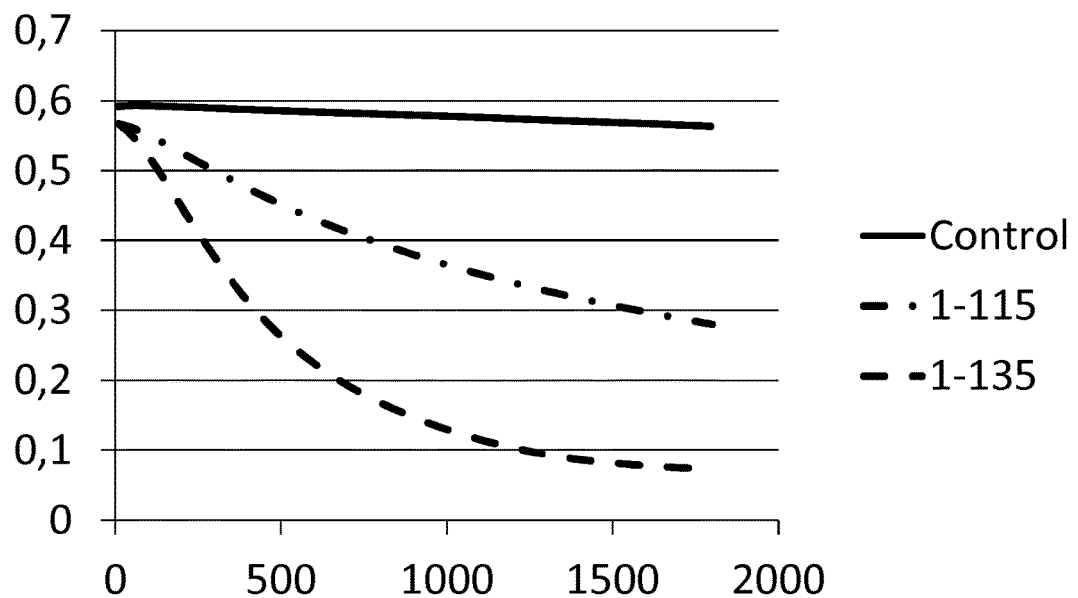

22 Claims, 10 Drawing Sheets
Specification includes a Sequence Listing.

ANTIMICROBIAL AGENTS

This application is a national phase application under 35 U.S.C. § 371 of International Application No. PCT/EP2015/053150, filed Feb. 13, 2015, which claims benefit of priority to European Application No. 14155288.5, filed Feb. 14, 2014, the entire contents of each of which are hereby incorporated by reference.

The present invention relates to polypeptides comprising an amino sequence selected from the group consisting of SEQ ID NO: 1, and fragments and derivatives thereof. The invention also relates to the corresponding nucleic acids vectors, host cells and compositions. The present inventions also relates to the use of said polypeptides, nucleic acids, vectors, host cells and compositions in a method for treatment of the human or animal body by surgery or therapy or in diagnostic methods practiced on the human or animal body, in particular for the treatment or prevention of Gram-negative bacterial infections. The polypeptides, nucleic acids, vectors, host cells and compositions according to the invention may also be used as an antimicrobial in food or feed, or in cosmetics, as disinfecting agent or in the environmental field.

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions ($Mg^{2+}$, $Ca^{2+}$) with the anionic components of the LPS molecule (phosphate groups in the lipid A and the inner core and carboxyl groups of KDO). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

Various types of agents having bactericidal or bacteriostatic activity are known, e.g. antibiotics, endolysins, antimicrobial peptides and defensins. Increasingly microbial resistance to antibiotics, however, is creating difficulties in treating more and more infections caused by bacteria. Particular difficulties arise with infections caused by Gram-negative bacteria like *Pseudomonas aeruginosa* and Enterobacteriaceae such as *Salmonella*.

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. They are either β(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage Cl endolysin towards group A streptococci (Nelson et al., 2001). Since then many publications have established endolysins as an attractive and complementary alternative to control bacterial infections, particularly by Gram positive bacteria. Subsequently different endolysins against other Gram positive pathogens such as *Streptococcus pneumoniae* (Loeffler et al., 2001), *Bacillus anthracis* (Schuch et al., 2002), *S. agalactiae* (Cheng et al., 2005) and *Staphylococcus aureus* (Rashel et al, 2007) have proven their efficacy as enzybiotics. Nowadays, the most important challenge of endolysin therapy lies in the insensitivity of Gram-negative bacteria towards the exogenous action of endolysins, since the outer membrane shields the access of endolysins from the peptidoglycan. This currently prevents the expansion of the range of effective endolysins to important Gram-negative pathogens.

Antimicrobial peptides (AMPs) represent a wide range of short, cationic or amphiphatic, gene encoded peptide antibiotics that can be found in virtually every organism. Different AMPs display different properties, and many peptides in this class are being intensively researched not only as antibiotics, but also as templates for cell penetrating peptides. Despite sharing a few common features (e.g., cationicity, amphiphaticity and short size), AMP sequences vary greatly, and at least four structural groups (α-helical, β-sheet, extended and looped) have been proposed to accommodate the diversity of the observed AMP conformations. Likewise, several modes of action as antibiotics have been proposed, and it was shown e.g. that the primary target of many of these peptides is the cell membrane whereas for other peptides the primary target is cytoplasmic invasion and disruption of core metabolic functions. AMPs may become concentrated enough to exhibit cooperative activity despite the absence of specific target binding; for example, by forming a pore in the membrane, as is the case for most AMPs. However, this phenomenon has only been observed in model phospholipid bilayers, and in some cases, AMP concentrations in the membrane that were as high as one peptide molecule per six phospholipid molecules were required for these events to occur. These concentrations are close to, if not at, full membrane saturation. As the minimum inhibitory concentration (MIC) for AMPs are typically in the low micromolar range, scepticism has understandably arisen regarding the relevance of these thresholds and their importance in vivo (Melo et al., Nature reviews, Microbiology, 2009, 245).

Defensins are a large family of small, cationic, cysteine- and arginine-rich antimicrobial peptides, found in both vertebrates and invertebrates. Defensins are divided into five groups according to the spacing pattern of cysteines: plant, invertebrate, α-, β-, and θ-defensins. The latter three are mostly found in mammals. α-defensins are proteins found in neutrophils and intestinal epithelia. β-defensins are the most widely distributed and are secreted by leukocytes and epithelial cells of many kinds. θ-defensins have been rarely found so far e.g. in leukocytes of rhesus macaques. Defensins are active against bacteria, fungi and many enveloped and nonenveloped viruses. However, the concentrations needed for efficient killing of bacteria are mostly high, i.e. in the micromolar range. Activity of many peptides may be limited in presence of physiological salt conditions, divalent cations and serum. Depending on the content of hydrophobic amino acid residues defensins also show haemolytic activity.

In the art several combinations of endolysins with further amino acid sequence stretches have been described (see for example WO 2010/023207, WO 2010/149792, WO 2010/149795, WO 2011/023702, WO 2011/134998, WO 2012/085259 and WO 2012/059545). However there is still a constant need for new antibacterial agents active against Gram-negative bacteria.

This object is solved by the subject matter defined in the claims.

In the following a brief description of the appended figures will be given. The figures are intended to illustrate the present invention in more detail. However, they are not intended to limit the subject matter of the invention to any extent.

Figure 2:
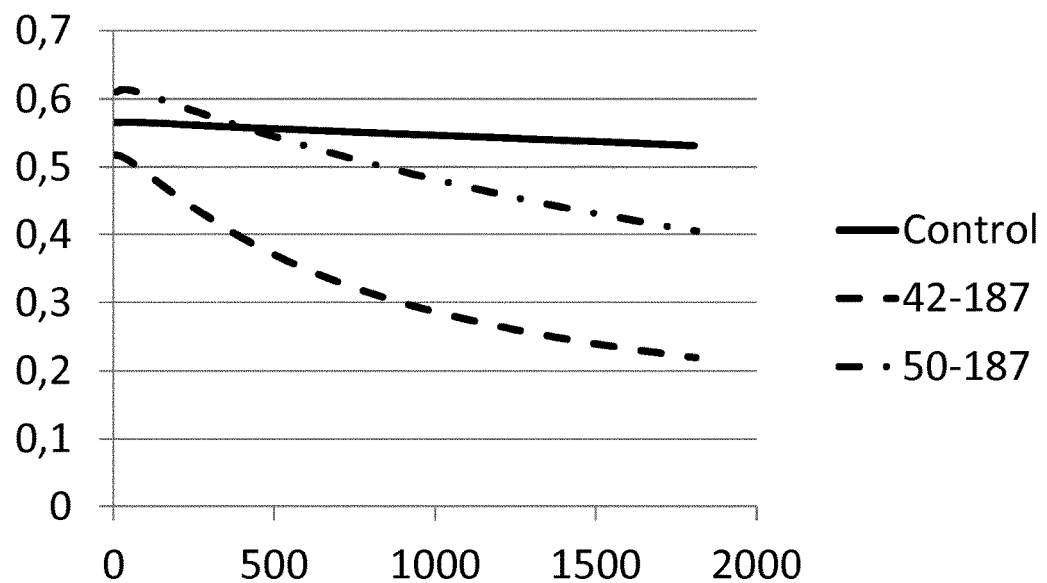

FIG. 1: illustrates that the C-terminal end of the endolysin isolated by the inventors (SEQ ID NO: 92) is dispensable for enzymatic activity on *E. coli*. Fragments 1-115 (SEQ ID NO: 50) and 1135 (SEQ ID NO: 54) show enzymatic activity. X-Axis: Time (s); Y-Axis: $OD_{600}$; Control: 20 mM HEPES pH 7.4, 0.5 M NaCl FIG. 2: illustrates that the N-terminal end of the endolysin isolated by the inventors (SEQ ID NO: 92) is dispensable for enzymatic activity on *E. coli*. Fragments 42-187 (SEQ ID NO: 82) and 50-187 (SEQ ID NO: 84) show enzymatic activity. X-Axis: Time (s); Y-Axis: $OD_{600}$; Control: 20 mM HEPES pH 7.4, 0.5 M NaCl.

Figure 3:
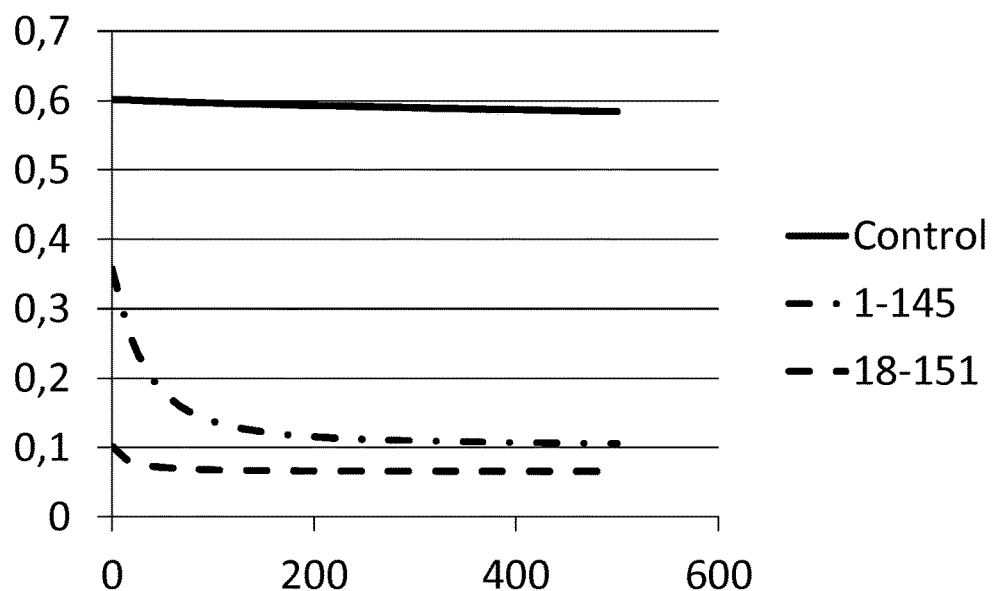
Figure 3:
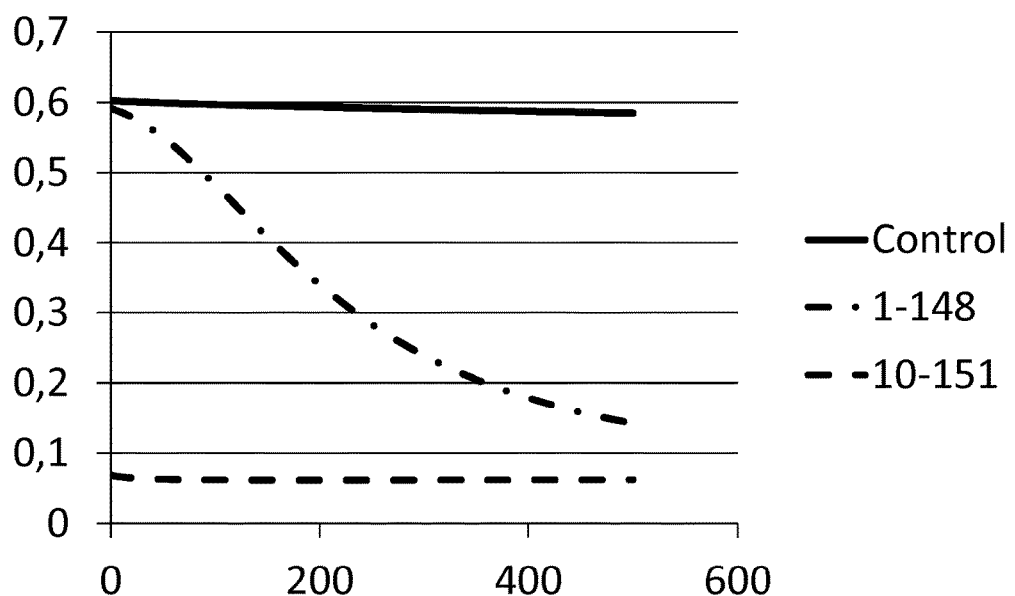

FIG. 3: illustrates enzymatic activity for further fragments of the endolysin isolated by the inventors (SEQ ID NO: 92). X-Axis: Time (s); Y-Axis: $OD_{600}$; Control: 20 mM HEPES pH 7.4, 0.5 M NaCl; A) Fragments 1-145 (SEQ ID NO: 56) and 18-151 (SEQ ID NO: 80) show enzymatic activity on *E. coli*. B) Fragments 1-148 (SEQ ID NO: 58) and 10-151 (SEQ ID NO: 74) show enzymatic activity on *E. coli*.

Figure 4:
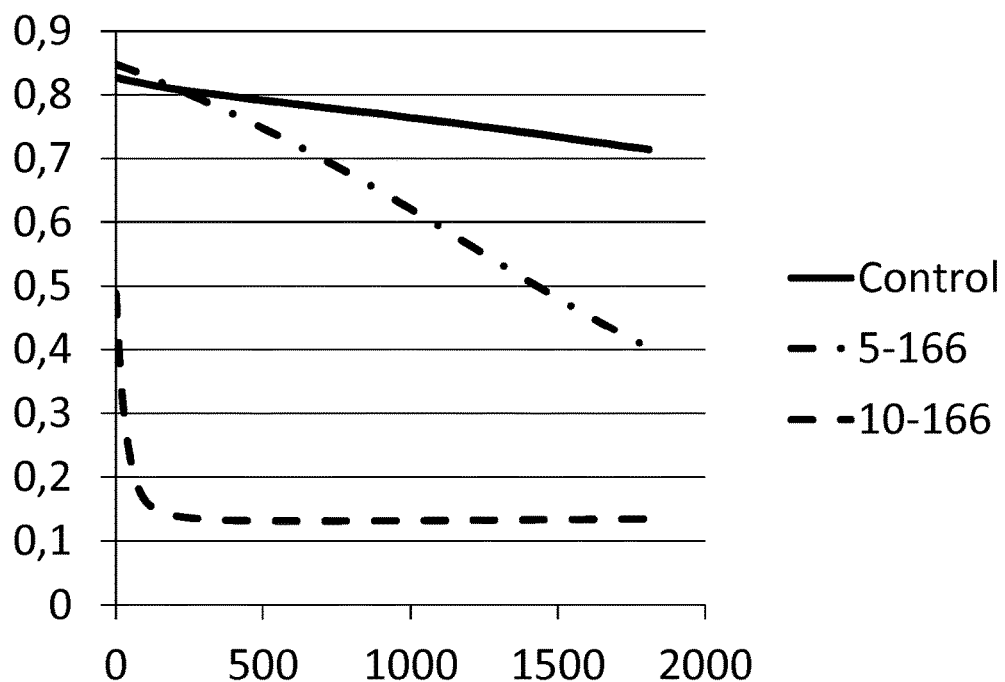
Figure 4:
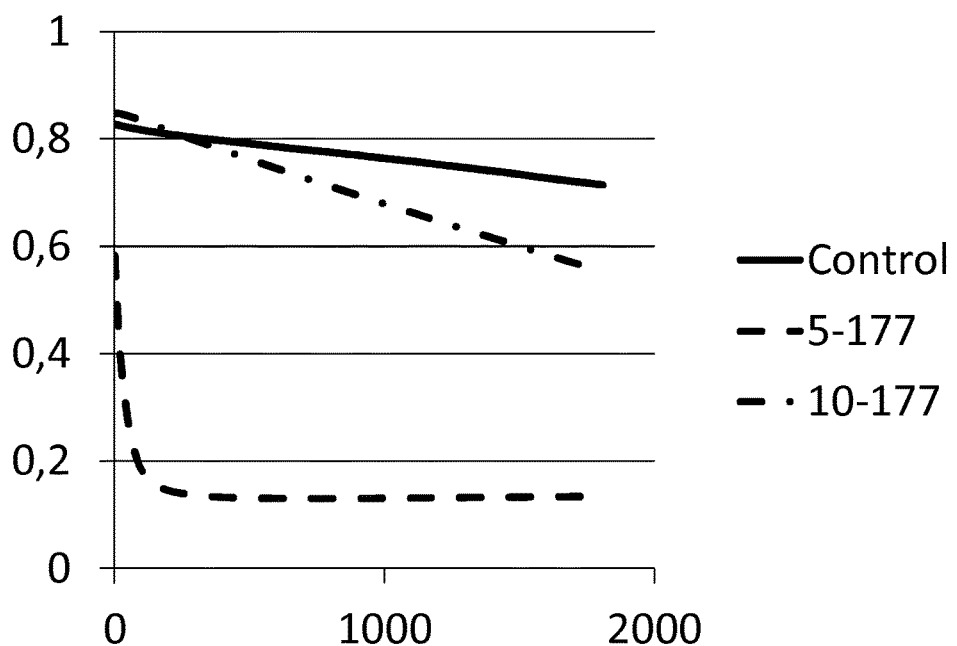

FIG. 4: illustrates enzymatic activity for further fragments of the endolysin isolated by the inventors (SEQ ID NO: 92). X-Axis: Time (s); Y-Axis: $OD_{600}$; Control: 20 mM HEPES pH 7.4, 0.5 M NaCl; A) Fragments 5-166 (SEQ ID NO: 70) and 10-166 (SEQ ID NO: 76) show enzymatic activity on *E. coli*. B) Fragments 5177 (SEQ ID NO: 72) and 10-177 (SEQ ID NO: 78) show enzymatic activity on *E. coli*.

Figure 5:
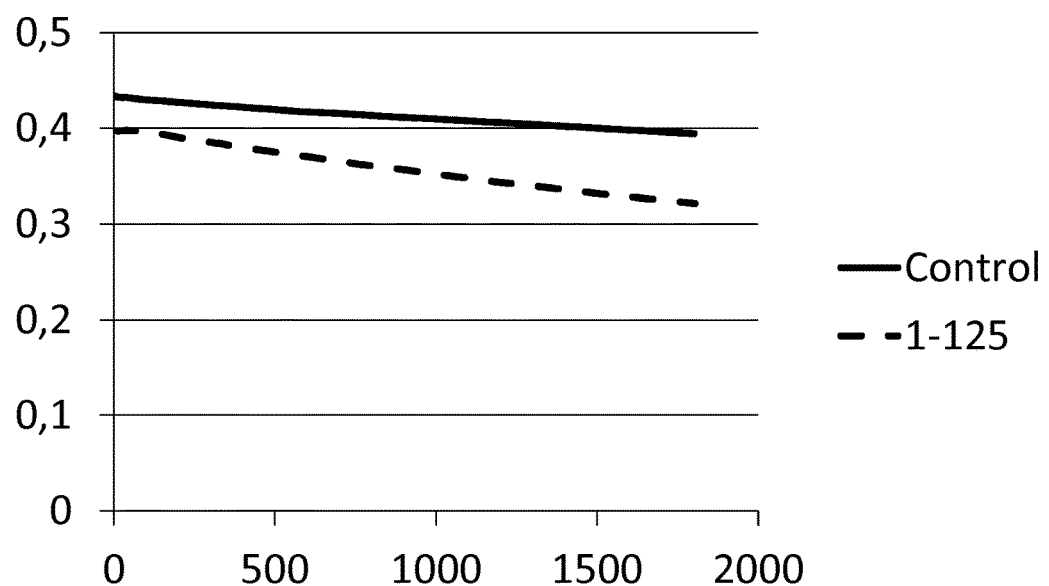

FIG. 5: illustrates enzymatic activity for a further fragment of the endolysin isolated by the inventors (SEQ ID NO: 92). Fragment 1-125 (SEQ ID NO: 52) shows enzymatic activity on *E. coli*. X-Axis: Time (s); Y-Axis: $OD_{600}$; Control: 20 mM HEPES pH 7.4, 0.5 M NaCl.

Figure 6:
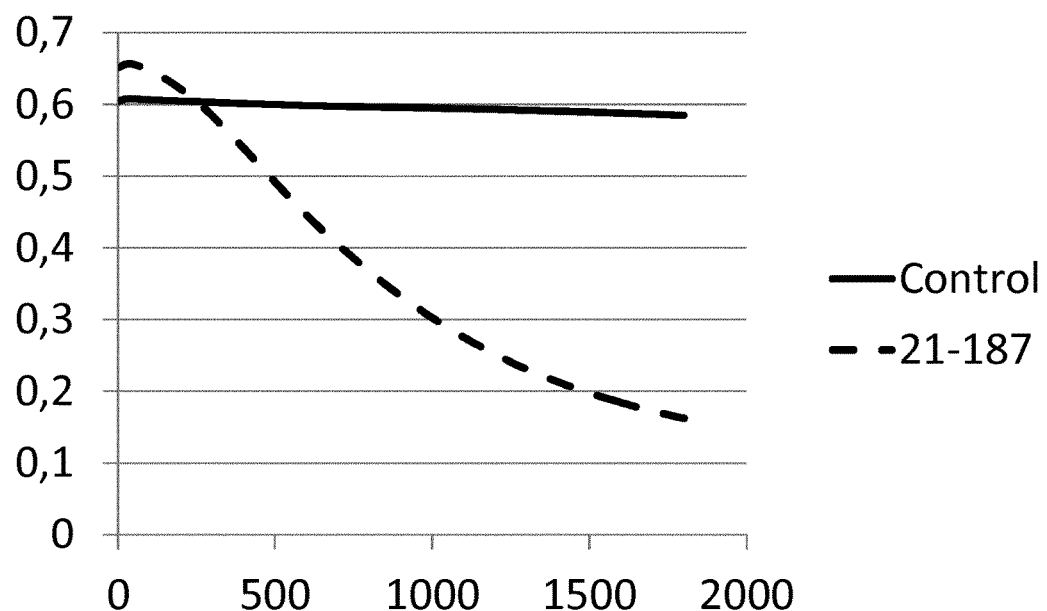
Figure 7:
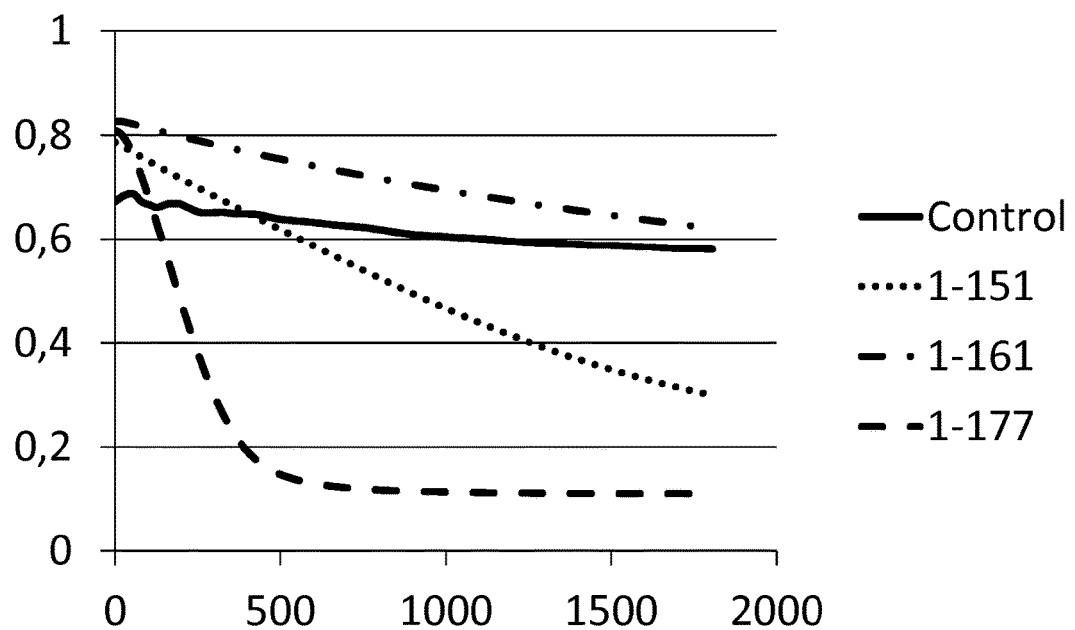
Figure 8:
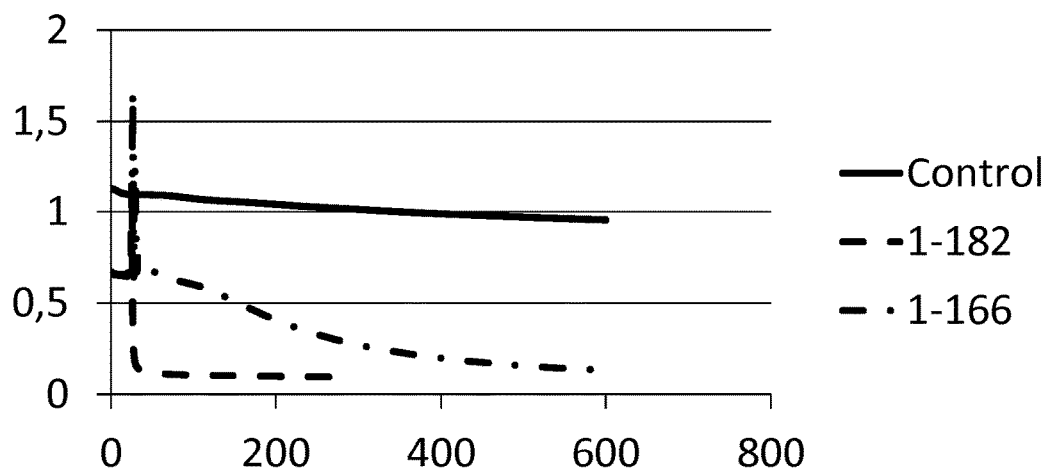
Figure 8:
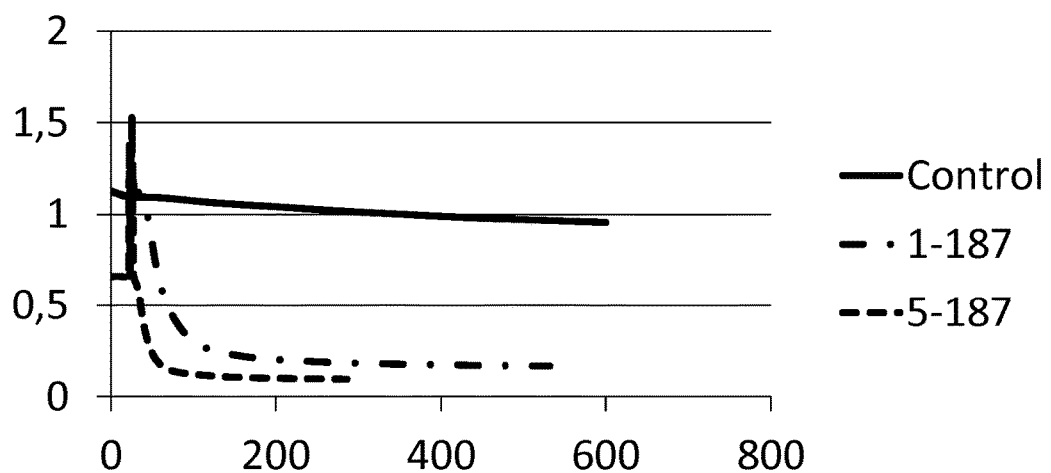

FIG. 6: illustrates enzymatic activity for a further fragment of the endolysin isolated by the inventors (SEQ ID NO: 92). Fragment 21-187 (SEQ ID NO: 86) shows enzymatic activity on *E. coli*. X-Axis: Time (s); Y-Axis: $OD_{600}$; Control: 20 mM HEPES pH 7.4, 0.5 M NaCl;

FIG. 7: illustrates enzymatic activity for further fragments of the endolysin isolated by the inventors (SEQ ID NO: 92). Fragments 1-151 (SEQ ID NO: 60), 1-161 (SEQ ID NO: 62) and 1-177 (SEQ ID NO: 66) show enzymatic activity on *E. coli*. X-Axis: Time (s); Y-Axis: $OD_{600}$; Control: 20 mM HEPES pH 7.4, 0.5 M NaCl. FIG. 8: illustrates enzymatic activity for the endolysin isolated by the inventors (SEQ ID NO: 92) as well as for fragments thereof. X-Axis: Time (s); Y-Axis: $OD_{600}$; Control: 20 mM HEPES pH 7.4, 0.5 M NaCl; A) Fragments 1-182 (SEQ ID NO: 68) and 1-166 (SEQ ID NO: 64) show enzymatic activity on *E. coli*. B) The full length endolysin (SEQ ID NO: 92) as well as fragment 5-187 (SEQ ID NO: 90) show enzymatic activity on *E. coli*.

Figure 9:
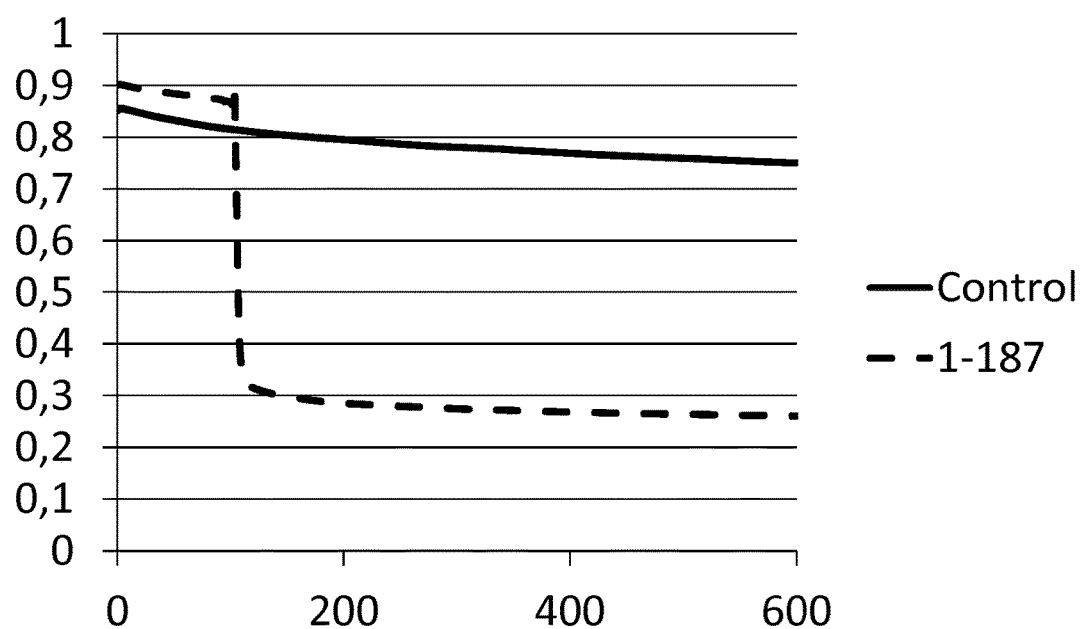

FIG. 9: illustrates enzymatic activity for the endolysin isolated by the inventors (SEQ ID NO: 92) on *Salmonella typhimurium*. X-Axis: Time (s); Y-Axis: $OD_{600}$; Control: 20 mM HEPES pH 7.4, 0.5 M NaCl.

Figure 10:
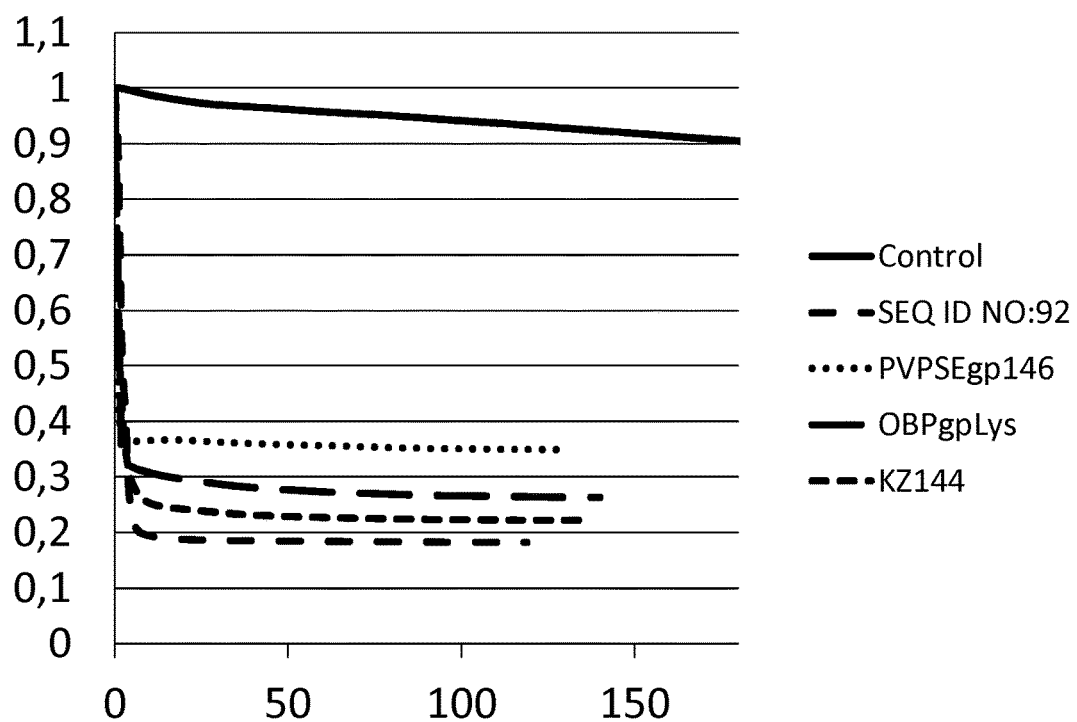

FIG. 10: compares enzymatic activity on *E. coli* for the endolysin isolated by the inventors (SEQ ID NO: 92) with endolysins KZ144 (SEQ ID NO: 226), OBPgpLys (SEQ ID NO: 227) and PVPSEgp146 (SEQ ID NO: 228). X-Axis: Time (s); Y-Axis: $OD_{600}$; Control: 20 mM HEPES pH 7.4, 0.5 M NaCl.

The term "polypeptide" as used herein refers in particular to a polymer of amino acid residues linked by peptide bonds in a specific sequence. The amino acid residues of a polypeptide may be modified by e.g. covalent attachments of various groups such as carbohydrates and phosphate. Other substances may be more loosely associated with the polypeptide, such as heme or lipid, giving rise to conjugated polypeptides which are also comprised by the term "polypeptide" as used herein. The term as used herein is intended to encompass also proteins. Thus, the term "polypeptide" also encompasses for example complexes of two or more amino acid polymer chains. The term "polypeptide" does encompass embodiments of polypeptides which exhibit optionally modifications typically used in the art, e.g. biotinylation, acetylation, pegylation, chemical changes of the amino-, SH- or carboxyl-groups (e.g. protecting groups) etc. As will become apparent from the description below, the polypeptide according to the present invention may also be a fusion protein, i.e. linkage of at least two amino acid sequences which do not occur in this combination in nature. The term "polypeptide" as used herein is not limited to a specific length of the amino acid polymer chain, but typically the polypeptide will exhibit a length of more than about 50 amino acids, more than about 100 amino acids or even more than about 150 amino acids. Usually, but not necessarily, a typical polypeptide of the present invention will not exceed about 750 amino acids in length. The inventive polypeptide may for instance be at most about 500 amino acids long, at most about 300 amino acids long, at most about 250 amino acids long or at most about 200 amino acids long. A possible length range for the inventive polypeptide, without being limited thereto, may thus for example be about 84 to about 250 amino acids, or about 100 to about 235 amino acids.

The term "fragment" as used herein refers to an amino acid sequence which is N-terminally, C-terminally, and/or on both termini truncated with respect to the respective reference sequence, for example a given SEQ ID NO. Thus, a fragment of an amino acid sequence as used herein is an amino acid sequence which is at least one amino acid shorter than the respective reference sequence. A fragment of an amino acid sequence as used herein is preferably an amino acid sequence which is at most 20, more preferably at most 19, more preferably at most 18, more preferably at most 17, more preferably at most 16, more preferably at most 15, more preferably at most 14, more preferably at most 13, more preferably at most 12, more preferably at most 11, more preferably at most 10, more preferably at most 9, more preferably at most 8, more preferably at most 7, more preferably at most 6, more preferably at most 5, more preferably at most 4, more preferably at most 3, more preferably at most 2, most preferably 1 amino acid residue shorter than the respective reference amino acid sequence. The fragment may for example exhibit vis-à-vis the reference sequence a truncation of 1, 2, 3, 4, 5, 6, 7, 8, 9, 10, 11, 12, 13, 14, 15, 16, 17, 18, 19 or 20 amino acids at the N-terminus, the C-terminus or both. It is understood that a polypeptide comprising a fragment of a given amino acid sequence does not comprise the full length of said reference amino acid sequence.

The term "derivative" as used herein refers to an amino acid sequence which exhibits, in comparison to the respective reference sequence, one or more additions, deletions, insertions, and/or substitutions. Such derived sequence will exhibit a certain level of sequence identity with the respective reference sequence, which is preferably at least 60%, such as at least 80%, at least 85%, at least 90%, at least 95%, at least 96%, at least 97%, at least 98% or at least 99%. Preferably, the differences in sequence are due to conservative amino acid substitutions.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 83, 63-98; Pearson and Lipman (1988), Proc. Natl. Acad. Sci. U. S. A 85, 2444-2448.). Sequences which are identical to other sequences to a certain extent can be identified by these programs. Furthermore, programs available in the Wisconsin Sequence Analysis Package, version 9.1 (Devereux et al, 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences. If herein reference is made to an amino acid sequence sharing a particular extent of sequence identity to a reference sequence, then said difference in sequence is preferably due to conservative amino acid substitutions. Preferably, such sequence retains the activity of the reference sequence, e.g. retains the activity of degrading the peptidoglycan layer of Gram-negative bacteria, albeit maybe at a slower rate. In addition, if reference is made herein to a sequence sharing "at least" at certain percentage of sequence identity, then 100% sequence identity are preferably not encompassed.

"Conservative amino acid substitutions", as used herein, may occur within a group of amino acids which have sufficiently similar physicochemical properties, so that a substitution between members of the group will preserve the biological activity of the molecule (see e.g. Grantham, R. (1974), Science 185, 862-864). Particularly, conservative amino acid substitutions are preferably substitutions in which the amino acids originate from the same class of amino acids (e.g. basic amino acids, acidic amino acids, polar amino acids, amino acids with aliphatic side chains, amino acids with positively or negatively charged side chains, amino acids with aromatic groups in the side chains, amino acids the side chains of which can enter into hydrogen bridges, e.g. side chains which have a hydroxyl function, etc.). Conservative substitutions are in the present case for example substituting a basic amino acid residue (Lys, Arg, His) for another basic amino acid residue (Lys, Arg, His), substituting an aliphatic amino acid residue (Gly, Ala, Val, Leu, lie) for another aliphatic amino acid residue, substituting an aromatic amino acid residue (Phe, Tyr, Trp) for another aromatic amino acid residue, substituting threonine by serine or leucine by isoleucine. Further conservative amino acid exchanges will be known to the person skilled in the art.

The term "deletion", as used herein, refers preferably to the absence of 1, 2, 3, 4, 5 (or even more than 5) continuous amino acid residues in the derivative sequence in comparison to the respective reference sequence, either intrasequentially or at the N- or C-terminus. A derivative of the present invention may exhibit one, two or more of such deletions.

The term "insertion", as used herein, refers preferably to the additional intrasequential presence of 1, 2, 3, 4, 5 (or even more than 5) continuous amino acid residues in the derivative sequence in comparison to the respective reference sequence. A derivative of the present invention may exhibit one, two or more of such insertions.

The term "addition" as used herein refers preferably to the additional presence of 1, 2, 3, 4, 5 (or even more than 5) continuous amino acid residues at the N- and/or C-terminus of the derivative sequence in comparison to the respective reference sequence.

The term "substitution" as used herein refers to the presence of an amino acid residue at a certain position of the derivative sequence which is different from the amino acid residue which is present or absent at the corresponding position in the reference sequence. A derivative of the present invention may exhibit 1, 2, 3, 4, 5, 6, 7, 8, 9, 10, 11, 12, 13, 14, 15, 16, 17, 18, 19, 20, or more of such substitutions. As mentioned above, preferably such substitutions are conservative substitutions.

As pointed out previously, the "derivative" as used herein, may comprise additions, deletions, insertions, and substitutions, i.e. combinations of one or more additions, deletions, insertions, and substitutions are conceivable. This includes for example combinations of deletions/insertions, insertions/deletions, deletions/additions, additions/deletions, insertion/additions, additions/insertions etc. A person skilled in the art will however understand that the presence of an amino acid residue at a certain position of the derivative sequence which is different from the one that is present at the respective same position in the reference sequence is not a combination of for example a deletion and a subsequent insertion at the same position but is a substitution as defined herein. Rather, if reference is made herein to combinations of one or more of additions, deletions, insertions, and substitutions, then combination of changes at distinct positions in the sequence are intended, e.g. an addition at the N-terminus and an intrasequential deletion.

The term "cell wall", as used herein, refers to all components that form the outer cell enclosure of Gram-negative bacteria and thus guarantee their integrity. In particular, the term "cell wall" as used herein refers to peptidoglycan, the outer membrane of the Gram-negative bacteria with the lipopolysaccharide, the bacterial cell membrane, but also to additional layers deposited on the peptidoglycan as e.g. capsules, outer protein layers or slimes.

The term "amino acid sequence stretch" as used herein refers to a particular stretch of amino acid sequence in the amino acid sequence of the polypeptide of the invention. Said sequence refers to a sequence of a cationic peptide, a polycationic peptide, an amphipathic peptide, a hydrophobic peptide, a sushi peptide and/or an antimicrobial peptide. The term does not refer to conventional tags like His-tags, such as $His_5$-tags, $His_6$-tags, $His_7$-tags, $His_8$-tags, $His_9$-tags, $His_{10}$-tags, $His_{11}$-tags, $His_{12}$-tags, $His_{16}$-tags and $His_{20}$-tags, Strep-tags, Avi-tags, Myc-tags, Gst-tags, JS-tags, cysteintags, FLAG-tags or other tags known in the art, thioredoxin or maltose binding proteins (MBP). The term "tag" (in contrast to the term "amino acid sequence stretch"), as used herein, refers to a peptide which can be useful to facilitate expression and/or affinity purification of a polypeptide, to immobilize a polypeptide to a surface or to serve as a marker or a label moiety for detection of a polypeptide e.g. by antibody binding in different ELISA assay formats as long as the function making the tag useful for one of the above listed facilitation is not caused by the positively charge of said peptide. Non-limiting examples for tags are the above mentioned conventional tags. However, the $His_6$-tag may, depending on the respective pH, also be positively charged, but is used as affinity purification tool as it binds to immobilized divalent cations and is not understood to be a "amino acid sequence stretch" as used herein. Preferably an amino acid sequence stretch, as used herein, has a length of about 6 to about 39 amino acid residues.

As used herein, the term "cationic peptide" refers preferably to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides, but also includes cationic peptides which comprise for example less than 20%, preferably less than 10% positively charged amino acid residues.

The term "polycationic peptide", as used herein, refers preferably to a peptide composed of mostly positively charged amino acid residues, in particular lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP), as used herein, refers preferably to any naturally occurring peptide that has microbicidal and/or microbistatic activity on for example bacteria, viruses, fungi, yeasts, *mycoplasma* and protozoa. Thus, the term "antimicrobial peptide" as used herein refers in particular to any peptide having anti-bacterial, antifungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties. Preferred are anti-bacterial peptides. The antimicrobial peptide may be a member of the RNase A super family, a defensin, cathelicidin, granulysin, histatin, psoriasin, dermicidine or hepcidin. The antimicrobial peptide may be naturally occurring in insects, fish, plants, arachnids, vertebrates or mammals. Preferably the antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis, Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga* peregrine, scorpion, horseshoe crab, catfish, preferably in *Parasilurus asotus*, cow, pig, sheep, porcine, bovine, monkey and human. As used herein, an "antimicrobial peptide" (AMP) may in particular be a peptide which is not a cationic peptide, polycationic peptide, amphipathic peptide, sushi peptide, defensins, and hydrophobic peptide, but nevertheless exhibits antimicrobial activity.

The term "sushi peptide", as used herein, refers to complement control proteins (CCP) having short consensus repeats. The sushi module of sushi peptides functions as a protein-protein interaction domain in many different proteins. Peptides containing a Sushi domain have been shown to have antimicrobial activities. Preferably, sushi peptides are naturally occurring peptides.

The term "amphipathic peptide", as used herein, refers to synthetic peptides having both hydrophilic and hydrophobic functional groups. Preferably, the term "amphipathic peptide" as used herein refers to a peptide having a defined arrangement of hydrophilic and hydrophobic groups e.g. amphipathic peptides may be e.g. alpha helical, having predominantly non polar side chains along one side of the helix and polar residues along the rest of its surface.

The term "hydrophobic group", as used herein, refers preferably to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a non-aqueous environment. Examples of amino acid residues with hydrophobic side chains are valine, isoleucine, leucine, methionine, phenylalanine, tryptophan, cysteine, alanine, tyrosine, and proline residues.

The term "hydrophobic peptide", as used herein, refers to a hydrophobic peptide, which is preferably composed of mostly amino acid residues with hydrophobic groups. Such peptide is preferably composed of mostly hydrophobic amino acid residues, i.e. at least about 20, 30, 40, 50, 60, 70, 75, 80, 85, 90, 95 or at least about 100% of the amino acid residues are hydrophobic amino acid residues. The amino acid residues being not hydrophobic are preferably neutral and preferably not hydrophilic.

The term "comprising", as used herein, shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The present invention relates in a first aspect to a polypeptide comprising an amino sequence selected from the group consisting of: a) SEQ ID NO: 1, b) a fragment of a) (wherein the fragment is preferably at most 20 amino acids shorter than SEQ ID NO: 1), and c) a derivative of a), or b). Preferred derivatives are derivatives of a). In a particular preferred embodiment the polypeptide according to the present invention comprises an amino sequence according to SEQ ID NO: 1.

An inventive polypeptide may for example comprise any amino sequence selected from: a2) the group consisting of amino acid sequences according to any one of SEQ ID NOs: 2 to 92, b2) a fragment of any one of the amino acid sequences according to SEQ ID NOs: 2 to 92, and c2) a derivative of any one sequence according to a) or b). Preferred derivatives are derivatives of a2).

An inventive polypeptide comprising a derivative sequence of SEQ ID NO: 1 comprises preferably an amino acid sequence sharing at least 80% sequence identity with SEQ ID NO: 1, more preferably at least 85% sequence identity with SEQ ID NO: 1, more preferably at least 90% sequence identity with SEQ ID NO: 1, more preferably at least 95% sequence identity with SEQ ID NO: 1, more preferably at least 96% sequence identity with SEQ ID NO: 1, more preferably at least 97% sequence identity with SEQ ID NO: 1, more preferably at least 98% sequence identity with SEQ ID NO: 1, most preferably at least 99% sequence identity with SEQ ID NO: 1.

Similarly, an inventive polypeptide comprising a derivative sequence of any one of the amino acid sequences according to SEQ ID NOs: 2 to 92 comprises preferably an amino acid sequence sharing at least 80% sequence identity with any one of the amino acid sequences according to SEQ ID NOs: 2 to 92, more preferably at least 85% sequence identity with any one of the amino acid sequences according to SEQ ID NOs: 2 to 92, more preferably at least 90% sequence identity with any one of the amino acid sequences according to SEQ ID NOs: 2 to 92, more preferably at least 95% sequence identity with any one of the amino acid sequences according to SEQ ID NOs: 2 to 92, more preferably at least 96% sequence identity with any one of the amino acid sequences according to SEQ ID NOs: 2 to 92, more preferably at least 97% sequence identity with any one of the amino acid sequences according to SEQ ID NOs: 2 to 92, more preferably at least 98% sequence identity with any one of the amino acid sequences according to SEQ ID NOs: 2 to 92, most preferably at least 99% sequence identity with any one of the amino acid sequences according to SEQ ID NOs: 2 to 92.

In particular, an inventive polypeptide comprising a derivative sequence of SEQ ID NO: 91, comprises preferably an amino acid sequence sharing at least 80% sequence identity with SEQ ID NO: 91, more preferably at least 85% sequence identity with SEQ ID NO: 91, more preferably at least 90% sequence identity with SEQ ID NO: 91, more preferably at least 95% sequence identity with SEQ ID NO: 91, more preferably at least 96% sequence identity with SEQ ID NO: 91, more preferably at least 97% sequence identity with SEQ ID NO: 91, more preferably at least 98% sequence identity with SEQ ID NO: 91, most preferably at least 99% sequence identity with SEQ ID NO: 91.

A derivative of any of SEQ ID NOs: 1 to 92 and respective fragments thereof may for example exhibit an addition, insertion, and/or deletion of 1, 2, 3, 4 or 5 amino acid residues. A derivative of any of SEQ ID NOs: 1 to 92 and respective fragments thereof may also for example exhibit 1, 2, 3, 4 or more substitutions, preferably only 1 amino acid substitution. Preferably 25 or less, more preferably 20 or less, more preferably 15 or less, more preferably 10 or less, most preferably 5 or less substitutions are present in the sequence stretch corresponding to SEQ ID NO: 1 in the inventive polypeptide.

Fragments of SEQ ID NO: 1, which are contemplated by the present invention, may for example be selected from the group consisting of SEQ ID NOs: 3, 5 and 7. Hence, a polypeptide according to the present invention may for example comprise a sequence selected from the group consisting of SEQ ID NOs: 4, 6 and 8.

The present invention also contemplates polypeptides comprising a sequence which is a derivative of a fragment of SEQ ID NO:1, such as a derivative of SEQ ID NOs: 4, 5, 6, 7 and 8. Preferably, such derivative shares at least 80% sequence identity with such fragment, e.g. selected from the group consisting of SEQ ID NOs: 4, 5, 6, 7 and 8, more preferably at least 85% sequence identity with such fragment, e.g. selected from the group consisting of SEQ ID NOs: 4, 5, 6, 7 and 8, more preferably at least 90% sequence identity with such fragment, e.g. selected from the group consisting of SEQ ID NOs: 4, 5, 6, 7 and 8, more preferably at least 95% sequence identity with such fragment, e.g. selected from the group consisting of SEQ ID NOs: 4, 5, 6, 7 and 8, more preferably at least 96% sequence identity with such fragment, e.g. selected from the group consisting of SEQ ID NOs: 4, 5, 6, 7 and 8, more preferably at least 97% sequence identity with such fragment, e.g. selected from the group consisting of SEQ ID NOs: 4, 5, 6, 7 and 8, more preferably at least 98% sequence identity with such fragment, e.g. selected from the group consisting of SEQ ID NOs: 4, 5, 6, 7 and 8, most preferably at least 99% sequence identity with such fragment, e.g. selected from the group consisting of SEQ ID NOs: 4, 5, 6, 7 and 8.

In a further embodiment, the polypeptide of the present invention may comprise a sequence selected from the group consisting of SEQ ID NOs: 9, 10, 11 and 12 or may comprise a derivative of any of these sequences, i.e. SEQ ID NOs: 9, 10, 11 and 12. Preferably, such derivative shares at least 80% sequence identity with such sequence, i.e. selected from the group consisting of SEQ ID NOs: 9, 10, 11 and 12, more preferably at least 85% sequence identity with such sequence, i.e. selected from the group consisting of SEQ ID NOs: 9, 10, 11 and 12, more preferably at least 90% sequence identity with such sequence, i.e. selected from the group consisting of SEQ ID NOs: 9, 10, 11 and 12, more preferably at least 95% sequence identity with such sequence, i.e. selected from the group consisting of SEQ ID NOs: 9, 10, 11 and 12, more preferably at least 96% sequence identity with such sequence, i.e. selected from the group consisting of SEQ ID NOs: 9, 10, 11 and 12, more preferably at least 97% sequence identity with such sequence, i.e. selected from the group consisting of SEQ ID NOs: 9, 10, 11 and 12, more preferably at least 98% sequence identity with such sequence, i.e. selected from the group consisting of SEQ ID NOs: 9, 10, 11 and 12, most preferably at least 99% sequence identity with such sequence, i.e. selected from the group consisting of SEQ ID NOs: 9, 10, 11 and 12.

Particularly preferred fragments and derivatives of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90 and 92 (even numbers) are those lacking at least the N-terminal methionine residue (SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, and 91; uneven numbers). Such embodiments are particularly preferred if the inventive polypeptide comprises further N-terminal sequences, e.g. an additional amino acid sequence stretch as defined herein.

It is understood that whatever the sequence of the inventive polypeptide looks like in other respects, for the purpose of recombinant expression it is preferred if at the N-terminus of the inventive polypeptide a methionine (Met) residue is (additionally) present, for example in combination with glycine and serine (Met-Gly-Ser).

The present invention is inter alia based on the identification of a novel endolysin (SEQ ID NO:92). Moreover, the inventors showed that absence of large N-terminal and C-terminal portions of said enzyme still yields active enzyme. Thus, also fragments of said endolysin sequence and in particular derivatives thereof can be used for technical applications. In table 1 exemplary sequence elements of SEQ ID NO:92 particularly contemplated by the inventors to be used in the context of the present invention are set forth:

TABLE 1

| SEQ ID NO: | Pos. in SEQ ID NO: 92 | length |
|---|---|---|
| 1 | 42-125 | 84 |
| 2 | 42-125* | 85 |
| 3 | 50-115 | 66 |
| 4 | 50-115* | 67 |
| 5 | 50-125 | 76 |
| 6 | 50-125* | 77 |
| 7 | 42-115 | 74 |
| 8 | 42-115* | 75 |
| 9 | 50-135 | 86 |
| 10 | 50-135* | 87 |
| 11 | 21-115 | 95 |
| 12 | 21-115* | 96 |
| 13 | 42-135 | 94 |
| 14 | 42-135* | 95 |
| 15 | 42-145 | 104 |
| 16 | 42-145* | 105 |
| 17 | 42-148 | 107 |
| 18 | 42-148* | 108 |
| 19 | 42-151 | 110 |
| 20 | 42-151* | 111 |
| 21 | 21-135 | 115 |
| 22 | 21-135* | 116 |
| 23 | 21-145 | 125 |
| 24 | 21-145* | 126 |
| 25 | 21-148 | 128 |
| 26 | 21-148* | 129 |
| 27 | 21-151 | 131 |
| 28 | 21-151* | 132 |
| 29 | 21-125 | 105 |
| 30 | 21-125* | 106 |
| 31 | 18-125 | 108 |
| 32 | 18-125* | 109 |
| 33 | 10-125 | 116 |
| 34 | 10-125* | 117 |
| 35 | 5-125 | 121 |
| 36 | 5-125* | 122 |
| 37 | 32-135 | 104 |

TABLE 1-continued

| SEQ ID NO: | Pos. in SEQ ID NO: 92 | length |
|---|---|---|
| 38 | 32-135* | 105 |
| 39 | 18-135 | 118 |
| 40 | 18-135* | 119 |
| 41 | 10-135 | 126 |
| 42 | 10-135* | 127 |
| 43 | 5-135 | 131 |
| 44 | 5-135* | 132 |
| 45 | 16-186 | 171 |
| 46 | 16-186* | 172 |
| 47 | 4-187 | 184 |
| 48 | 4-187* | 185 |
| 49 | 2-115 | 114 |
| 50 | 1-115 | 115 |
| 51 | 2-125 | 124 |
| 52 | 1-125 | 125 |
| 53 | 2-135 | 134 |
| 54 | 1-135 | 135 |
| 55 | 2-145 | 144 |
| 56 | 1-145 | 145 |
| 57 | 2-148 | 147 |
| 58 | 1-148 | 148 |
| 59 | 2-151 | 150 |
| 60 | 1-151 | 151 |
| 61 | 2-161 | 160 |
| 62 | 1-161 | 161 |
| 63 | 2-166 | 165 |
| 64 | 1-166 | 166 |
| 65 | 2-177 | 176 |
| 66 | 1-177 | 177 |
| 67 | 2-182 | 181 |
| 68 | 1-182 | 182 |
| 69 | 5-166 | 162 |
| 70 | 5-166* | 163 |
| 71 | 5-177 | 173 |
| 72 | 5-177* | 174 |
| 73 | 10-151 | 142 |
| 74 | 10-151* | 143 |
| 75 | 10-166 | 157 |
| 76 | 10-166* | 158 |
| 77 | 10-177 | 168 |
| 78 | 10-177* | 169 |
| 79 | 18-151 | 134 |
| 80 | 18-151* | 135 |
| 81 | 42-187 | 146 |
| 82 | 42-187* | 147 |
| 83 | 50-187 | 138 |
| 84 | 50-187* | 139 |
| 85 | 21-187 | 167 |
| 86 | 21-187* | 168 |
| 87 | 10-187 | 178 |
| 88 | 10-187* | 179 |
| 89 | 5-187 | 183 |
| 90 | 5-187* | 184 |
| 91 | 2-187 | 186 |
| 92 | 1-187 | 187 |

*Additional methionine at the N-terminus

Some of the above sequences, without being limited thereto, are set forth explicitly in table 2 below:

TABLE 2

| Sequence (N → C) | length | SEQ ID NO: | Pos. |
|---|---|---|---|
| ILYERHIMARLLKAKGVPIAGLPSDLVNTTPG GYGKFSEQHGKLDRAVKIDRECALQSCSWGMF QLMGFNYKLCGYATVQAFVN | 84 | SEQ ID NO: 1 | 42-125 |

TABLE 2-continued

| Sequence (N → C) | length | SEQ ID NO: | Pos. |
|---|---|---|---|
| MILYERHIMARLLKAKGVPIAGLPSDLVNTTP GGYGKFSEQHGKLDRAVKIDRECALQSCSWGM FQLMGFNYKLCGYATVQAFVN | 85 | SEQ ID NO: 2 | Met+ 42-125 |
| CEVAAIKAIASVETKGSAWITPGVPQILYERH IMARLLKAKGVPIAGLPSDLVNTTPGGYGKFS EQHGKLDRAVKIDRECALQSCSWGMFQLMGFN YKLCGYATVQAFVNAMYKSEDEQLNAFVGFIK SNLQLNDALKSKDWATVARLYNGADYKINSYD QKLAVAYESNK | 171 | SEQ ID NO: 45 | 16-186 |
| MCEVAAIKAIASVETKGSAWITPGVPQILYER HIMARLLKAKGVPIAGLPSDLVNTTPGGYGKF SEQHGKLDRAVKIDRECALQSCSWGMFQLMGF NYKLCGYATVQAFVNAMYKSEDEQLNAFVGFI KSNLQLNDALKSKDWATVARLYNGADYKINSY DQKLAVAYESNK | 172 | SEQ ID NO: 46 | Met 16-186 |
| EKSFVEAAASLGCEVAAIKAIASVETKGSAWI TPGVPQILYERHIMARLLKAKGVPIAGLPSDL VNTTPGGYGKFSEQHGKLDRAVKIDRECALQS CSWGMFQLMGFNYKLCGYATVQAFVNAMYKSE DEQLNAFVGFIKSNLQLNDALKSKDWATVARL YNGADYKINSYDQKLAVAYESNKR | 184 | SEQ ID NO: 47 | 4-187 |
| MEKSFVEAAASLGCEVAAIKAIASVETKGSAW ITPGVPQILYERHIMARLLKAKGVPIAGLPSD LVNTTPGGYGKFSEQHGKLDRAVKIDRECALQ SCSWGMFQLMGFNYKLCGYATVQAFVNAMYKS EDEQLNAFVGFIKSNLQLNDALKSKDWATVAR LYNGADYKINSYDQKLAVAYESNKR | 185 | SEQ ID NO: 48 | Met+ 4-187 |
| LSEKSFVEAAASLGCEVAAIKAIASVETKGSA WITPGVPQILYERHIMARLLKAKGVPIAGLPS DLVNTTPGGYGKFSEQHGKLDRAVKIDRECAL QSCSWGMFQLMGFNYKLCGYATVQAFVNAMYK SEDEQLNAFVGFIKSNLQLNDALKSKDWATVA RLYNG | 165 | SEQ ID NO: 63 | 2-166 |
| MLSEKSFVEAAASLGCEVAAIKAIASVETKGS AWITPGVPQILYERHIMARLLKAKGVPIAGLP SDLVNTTPGGYGKFSEQHGKLDRAVKIDRECA LQSCSWGMFQLMGFNYKLCGYATVQAFVNAMY KSEDEQLNAFVGFIKSNLQLNDALKSKDWATV ARLYNG | 166 | SEQ ID NO: 64 | 1-166 |
| LSEKSFVEAAASLGCEVAAIKAIASVETKGSA WITPGVPQILYERHIMARLLKAKGVPIAGLPS DLVNTTPGGYGKFSEQHGKLDRAVKIDRECAL QSCSWGMFQLMGFNYKLCGYATVQAFVNAMYK SEDEQLNAFVGFIKSNLQLNDALKSKDWATVA RLYNGADYKINSYDQK | 176 | SEQ ID NO: 65 | 2-177 |
| MLSEKSFVEAAASLGCEVAAIKAIASVETKGS AWITPGVPQILYERHIMARLLKAKGVPIAGLP SDLVNTTPGGYGKFSEQHGKLDRAVKIDRECA LQSCSWGMFQLMGFNYKLCGYATVQAFVNAMY KSEDEQLNAFVGFIKSNLQLNDALKSKDWATV ARLYNGADYKINSYDQK | 177 | SEQ ID NO: 66 | 1-177 |
| LSEKSFVEAAASLGCEVAAIKAIASVETKGSA WITPGVPQILYERHIMARLLKAKGVPIAGLPS DLVNTTPGGYGKFSEQHGKLDRAVKIDRECAL QSCSWGMFQLMGFNYKLCGYATVQAFVNAMYK SEDEQLNAFVGFIKSNLQLNDALKSKDWATVA RLYNGADYKINSYDQKLAVAY | 181 | SEQ ID NO: 67 | 2-182 |
| MLSEKSFVEAAASLGCEVAAIKAIASVETKGS AWITPGVPQILYERHIMARLLKAKGVPIAGLP SDLVNTTPGGYGKFSEQHGKLDRAVKIDRECA LQSCSWGMFQLMGFNYKLCGYATVQAFVNAMY KSEDEQLNAFVGFIKSNLQLNDALKSKDWATV ARLYNGADYKINSYDQKLAVAY | 182 | SEQ ID NO: 68 | 1-182 |
| IKAIASVETKGSAWITPGVPQILYERHIMARL LKAKGVPIAGLPSDLVNTTPGGYGKFSEQHGK LDRAVKIDRECALQSCSWGMFQLMGFNYKLCG YATVQAFVNAMYKSEDEQLNAFVGFIKSNLQL NDALKSKDWATVARLYNGADYKINSYDQKLAV AYESNKR | 167 | SEQ ID NO: 85 | 21-187 |
| MIKAIASVETKGSAWITPGVPQILYERHIMAR LLKAKGVPIAGLPSDLVNTTPGGYGKFSEQHG KLDRAVKIDRECALQSCSWGMFQLMGFNYKLC GYATVQAFVNAMYKSEDEQLNAFVGFIKSNLQ LNDALKSKDWATVARLYNGADYKINSYDQKLA VAYESNKR | 168 | SEQ ID NO: 86 | Met+ 21-187 |
| AAASLGCEVAAIKAIASVETKGSAWITPGVPQ ILYERHIMARLLKAKGVPIAGLPSDLVNTTPG GYGKFSEQHGKLDRAVKIDRECALQSCSWGMF QLMGFNYKLCGYATVQAFVNAMYKSEDEQLNA FVGFIKSNLQLNDALKSKDWATVARLYNGADY KINSYDQKLAVAYESNKR | 178 | SEQ ID NO: 87 | 10-187 |
| MAAASLGCEVAAIKAIASVETKGSAWITPGVP QILYERHIMARLLKAKGVPIAGLPSDLVNTTP GGYGKFSEQHGKLDRAVKIDRECALQSCSWGM FQLMGFNYKLCGYATVQAFVNAMYKSEDEQLN AFVGFIKSNLQLNDALKSKDWATVARLYNGAD YKINSYDQKLAVAYESNKR | 179 | SEQ ID NO: 88 | Met+ 10-187 |
| KSFVEAAASLGCEVAAIKAIASVETKGSAWIT PGVPQILYERHIMARLLKAKGVPIAGLPSDLV NTTPGGYGKFSEQHGKLDRAVKIDRECALQSC SWGMFQLMGENYKLCGYATVQAFVNAMYKSED EQLNAFVGFIKSNLQLNDALKSKDWATVARLY NGADYKINSYDQKLAVAYESNKR | 183 | SEQ ID NO: 89 | 5-187 |
| MKSFVEAAASLGCEVAAIKAIASVETKGSAWI TPGVPQILYERHIMARLLKAKGVPIAGLPSDL VNTTPGGYGKESEQHGKLDRAVKIDRECALQS CSWGMFQLMGENYKLCGYATVQAFVNAMYKSE DEQLNAFVGFIKSNLQLNDALKSKDWATVARL YNGADYKINSYDQKLAVAYESNKR | 184 | SEQ ID NO: 90 | Met+ 5-187 |
| LSEKSFVEAAASLGCEVAAIKAIASVETKGSA WITPGVPQILYERHIMARLLKAKGVPIAGLPS DLVNTTPGGYGKESEQHGKLDRAVKIDRECAL QSCSWGMFQLMGENYKLCGYATVQAFVNAMYK SEDEQLNAFVGFIKSNLQLNDALKSKDWATVA RLYNGADYKINSYDQKLAVAYESNKR | 186 | SEQ ID NO: 91 | 2-187 |
| MLSEKSFVEAAASLGCEVAAIKAIASVETKGS AWITPGVPQILYERHIMARLLKAKGVPIAGLP SDLVNTTPGGYGKESEQHGKLDRAVKIDRECA LQSCSWGMFQLMGENYKLCGYATVQAFVNAMY KSEDEQLNAFVGFIKSNLQLNDALKSKDWATV ARLYNGADYKINSYDQKLAVAYESNKR | 187 | SEQ ID NO: 92 | 1-187 |

Pos.: Indicates the position within SEQ ID NO: 92

A polypeptide according to the present invention may thus comprise a sequence selected from the group of sequences consisting of SEQ ID NO: 1 to 92, in particular selected from the group of sequences consisting of SEQ ID NO: 13 to 91. Furthermore, a polypeptide according to the invention may also comprise a derivative of any of said sequences, i.e. selected from the group of sequences consisting of SEQ ID NO: 1 to 92, in particular selected from the group of sequences consisting of SEQ ID NO: 13 to 91. Preferably, such derivative shares at least 80% sequence identity, more preferably at least 85% sequence identity, more preferably at least 90% sequence identity, more preferably at least 95% sequence identity, more preferably at least 96% sequence identity, more preferably at least 97% sequence identity, more preferably at least 98% sequence identity, most preferably at least 99% sequence identity with such sequence selected from the group of sequences consisting of SEQ ID NO: 1 to 92, in particular selected from the group of sequences consisting of SEQ ID NO: 13 to 91.

A polypeptide according to the present invention exhibits preferably the activity of a peptidoglycan degrading enzyme, i.e. is capable of degrading bacterial peptidoglycan. Typically a polypeptide of the present invention will be capable of degrading the peptidoglycan of bacteria of Gram-negative bacteria, such as *Salmonella* sp., *Escherichia*, *Acinetobacter*, *Vibrio*, and/or *Pseudomonas* (in particular *Pseudomonas syringae* pv. *porri*) bacteria. A peptidoglycan degrading enzyme usually exhibits at least one of the following enzymatic activities: endopeptidase, N-acetyl-muramoyl-L-alanine-amidase (amidase), N-acetyl-muramidase, N-acetyl-glucosaminidase or transglycosylase and thus is in principle suitable for degrading the peptidoglycan of gram negative bacteria.

The peptidoglycan degrading activity on gram negative bacteria can be measured by assays well known in the art, e.g. by muralytic assays in which the outer membrane of gram negative bacteria is permeabilized or removed (e.g. with chloroform) to allow the putative enzyme access to the peptidoglycan layer. If the enzyme is active, degradation of the peptidoglycan layer will lead to a drop of turbidity, which can be measured photometrically (see for example Briers et al., *J. Biochem. Biophys Methods* 70: 531-533, (2007).

Due to the similar structure of the peptidoglycan of Gram negative bacteria a polypeptide according to the present invention may also have the activity of degrading the peptidoglycan of various Gram-negative bacteria, i.e. selected preferably from the group consisting of:

Enterobacteriaceae,
   in particular *Escherichia, Shigella, Citrobacter, Edwardsiella, Enterobacter, Hafnia, Klebsiella, Morganella, Proteus, Providencia, Serratia,* and *Yersinia,*
Pseudomonadaceae,
   in particular *Burkholderia, Stenotrophomonas, Shewanella, Sphingomonas* and *Comamonas,*
*Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella, Spirochaetaceae,*
   in particular *Treponema* and *Borrelia,*
Leptospiraceae, *Campylobacter, Helicobacter, Spirillum, Streptobacillus,* Bacteroidaceae,
   in particular *Bacteroides, Fusobacterium, Prevotella* and *Porphyromonas;* and
*Acinetobacter,*
   in particular *A. baumanii.*

A polypeptide according to the present invention may comprise additionally at least one further amino acid sequence stretch selected from the group consisting of amphipathic peptide, cationic peptide, polycationic peptide, hydrophobic peptide, or naturally occurring antimicrobial peptide, like sushi peptide and defensin. This additional at least one amino acid sequence stretch may in principle be present at any position in the inventive polypeptide, but is preferably present at the termini, i.e. in the N- or C-terminal region of the inventive polypeptide. Such additional amino acid sequence stretch may be fused directly, or via a peptide linker, to the rest of the polypeptide. It is understood that if one (or more) such additional amino acid sequence stretches according to the present invention are present in the N-terminal region of the inventive polypeptide, then there may be further additional amino acids on the N-terminus of the additional amino acid sequence stretch. Preferably these comprise the amino acid methionine (Met), or the sequence methionine, glycine and serine (Met-Gly-Ser).

This at least one additional amino acid sequence stretch preferably has the function to lead the inventive polypeptide through the outer membrane of bacteria and may have activity or may have no or only low activity when administered without being fused to the polypeptide of the invention. The function to guide the polypeptide through the outer membrane of Gram-negative bacteria is caused by the outer membrane or LPS disrupting, permeabilising or destabilizing activity of said amino acid sequence stretches.

Such outer membrane or LPS disrupting or permeabilising or destabilizing activity of these amino acid sequence stretches may be determined in a method as follows: The bacteria cells to be treated are cultured in liquid medium or on agar plates. Then the bacteria cell concentration in the liquid medium is determined photometrically at $OD_{600\ nm}$ or the colonies on the agar plates are counted, respectively. Now, the bacteria cells in liquid medium or on the plates are treated with a polypeptide according to the present invention exhibiting at least one additional amino acid sequence stretch as defined herein. After incubation the bacteria cell concentration in the liquid medium is determined photometrically at $OD_{600\ nm}$ or the colonies on the agar plates are counted again. If the protein exhibits such outer membrane or LPS disrupting or permeabilising or destabilizing activity, the bacteria cells are lysed due to the treatment with the polypeptide and thus, the bacteria cell concentration in the liquid medium or the number of the bacteria colonies on the agar plate is reduced. Thus, the reduction in bacteria cell concentration or in the number of bacteria colonies after treatment with the protein is indicative for an outer membrane or LPS disrupting or permeabilising or destabilizing activity of the polypeptide.

Especially preferred are cationic and/or polycationic amino acid sequence stretches comprising at least one motive according to SEQ ID NO: 93 (KRKKRK). In particular cationic amino acid sequence stretches comprising at least 2, 3, 4, 5, 6, 7, 8, 9, 10, 11, 12, 13, 14, 15, 16 or 17 motives according to SEQ ID NO: 93 (KRKKRK) are preferred. More preferred are cationic peptide stretches comprising at least one KRK motive (lys-arg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motives.

In another preferred embodiment of the present invention the cationic amino acid sequence stretch comprises beside the positively charged amino acid residues, in particular lysine and/or arginine residues, neutrally charged amino acid residues, in particular glycine and/or serine residues. Preferred are cationic amino acid sequence stretches consisting of about 70% to about 100%, or about 80% to about 95%, or about 85% to about 90% positively charged amino acid residues, in particular lysine, arginine and/or histidine residues, more preferably lysine and/or arginine residues and of about 0% to about 30%, or about 5% to about 20%, or about 10% to about 20% neutrally charged amino acid residues, in particular glycine and/or serine residues. Preferred are amino acid sequence stretches consisting of about 4% to about 8% serine residues, of about 33% to about 36% arginine residues and of about 56% to about 63% lysine residues. Especially preferred are amino acid sequence stretches comprising at least one motive according to SEQ ID NO: 94 (KRXKR), wherein X is any other amino acid than lysine, arginine and histidine. Especially preferred are polypeptide stretches comprising at least one motive according to SEQ ID NO: 95 (KRSKR). More preferred are cationic stretches comprising at least about 2, 3, 4, 5, 6, 7, 8, 9, 10, 11, 12, 13, 14, 15, 16, 17, 18, 19 or at least about 20 motives according to SEQ ID NO: 94 (KRXKR) or SEQ ID NO: 95 (KRSKR).

Also preferred are amino acid sequence stretches consisting of about 9 to about 16% glycine residues, of about 4 to about 11% serine residues, of about 26 to about 32% arginine residues and of about 47 to about 55% lysine residues. Especially preferred are amino acid sequence stretches comprising at least one motive according to SEQ ID NO: 96 (KRGSG). More preferred are cationic stretches comprising at least about 2, 3, 4, 5, 6, 7, 8, 9, 10, 11, 12, 13, 14, 15, 16, 17, 18, 19 or at least bout 20 motives according to SEQ ID NO: 96 (KRGSG).

In another preferred embodiment of the present invention such cationic amino acid sequence stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Preferred are cationic amino acid sequence stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Examples for cationic and polycationic amino acid sequence stretches are listed in the following table:

TABLE 3

| amino acid sequence stretch | length | SEQ ID NO: |
|---|---|---|
| KRKKRK | 6 | 93 |
| KRKKRKKRK | 9 | 97 |
| RRRRRRRRR | 9 | 98 |
| KKKKKKKK | 8 | 99 |
| KRKKRKKRKK | 10 | 100 |
| KRKKRKKRKKRK | 12 | 101 |
| KRKKRKKRKRKKR | 14 | 102 |
| KKKKKKKKKKKKKKKK | 16 | 103 |
| KRKKRKKRKRKRKRKKRK | 18 | 104 |
| KRKKRKKRKKRKRKKRKK | 19 | 105 |
| RRRRRRRRRRRRRRRRRRR | 19 | 106 |
| KKKKKKKKKKKKKKKKKKK | 19 | 107 |
| KRKKRKKRKRSKRKKRKKRK | 20 | 108 |
| KRKKRKKRKRSKRKKRKKRKK | 21 | 109 |

TABLE 3-continued

| amino acid sequence stretch | length | SEQ ID NO: |
|---|---|---|
| KRKKRKKRKKRKKRKKRKKRK | 21 | 110 |
| KRKKRKKRKRGSGKRKKRKKRK | 22 | 111 |
| KRKKRKKRKRGSGSGKRKKRKKRK | 24 | 112 |
| KRKKRKKRKRKRKKRKKRKKRKK | 25 | 113 |
| KRKKRKKRKRSKRKKRKKRKRSKRKKRKKRK | 31 | 114 |
| KRKKRKKRKRGSGSGKRKKRKKRKGSGSGKRKKRKKRK | 38 | 115 |
| KRKKRKKRKKRKKRKKRKKRKRKKRKKRKKRKKRK | 39 | 116 |
| KRKKRKKRKRSKRKKRKKRKRSKRKKRKKRKRSKRKKRKRK | 42 | 117 |

In a further aspect of the present invention at least one of the additional amino acid sequence stretches is an antimicrobial peptide, which comprises a positive net charge and around 50% hydrophobic amino acids. The antimicrobial peptides are amphipathic with a length of about 12 to about 50 amino acid residues. The antimicrobial peptides are naturally occurring in insects, fish, plants, arachnids, vertebrates or mammals. Preferably the antimicrobial peptide may be naturally occurring in radish, silk moth, wolf spider, frog, preferably in *Xenopus laevis*, *Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human.

In another preferred embodiment of the present invention the antimicrobial amino acid sequence stretches consist of about 0% to about 5%, or about 0% to about 35%, or about 10% to about 35% or about 15% to about 45%, or about 20% to about 45% positively charged amino acid residues, in particular lysine and/or arginine residues and of about 50% to about 80%, or about 60% to about 80%, or about 55% to about 75%, or about 70% to about 90% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

In another preferred embodiment of the present invention the antimicrobial amino acid sequence stretches consist of about 4% to about 58% positively charged amino acid residues, in particular lysine and/or arginine residues and of about 33% to about 89% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Examples for antimicrobial amino acid sequences which may be used in carrying out the present invention are listed in the following table.

TABLE 4

| Peptide | Sequence | SEQ ID NO |
|---|---|---|
| LL-37 | LLGDFFRKSKEKIGKEFKRIVQRIKDFLRNLVPRTES | 118 |
| SMAP-29 | RGLRRLGRKIAHGVKKYGPTVLRIIRIAG | 119 |
| Indolicidin | ILPWKWPWWPWRR | 120 |
| Protegrin | RGGRLCYCRRRFCVCVGR | 121 |
| Cecropin P1 | SWLSKTAKKLENSAKKRISEGIAIAIQGGPR | 122 |
| Magainin | GIGKFLHSAKKFGKAFVGEIMNS | 123 |
| Pleurocidin | GWGSFFKKAAHVGKHVGKAALTHYL | 124 |
| Cecropin A (A. aegypti) | GGLKKLGKKLEGAGKRVFNAAEKALPVVAGAKALRK | 125 |
| Cecropin A (D. melanogaster) | GWLKKIGKKIERVGQHTRDATIQGLGIPQQAANVAATARG | 126 |
| Buforin II | TRSSRAGLQFPVGRVHRLLRK | 127 |
| Sarcotoxin IA | GWLKKIGKKIERVGQHTRDATIQGLGIAQQAANVAATAR | 128 |
| Apidaecin | ANRPVYIPPPRPPHPRL | 129 |
| Ascaphine 5 | GIKDWIKGAAKKLIKTVASHIANQ | 130 |
| Nigrocine 2 | GLLSKVLGVGKKVLCGVSGLVC | 131 |
| Pseudin 1 | GLNTLKKVFQGLHEAIKLINNHVQ | 132 |
| Ranalexin | FLGGLIVPAMICAVTKKC | 133 |
| Melittin | GIGAVLKVLTTGLPALISWIKRKRQQ | 134 |
| Lycotoxin 1 | IWLTALKFLGKHAAKKLAKQQLSKL | 135 |
| Parasin 1 | KGRGKQGGKVRAKAKTRSS | 136 |
| Buforin I | AGRGKQGGKVRAKAKTRSSRAGLQFPVGRVHRLLRKGNY | 137 |
| Dermaseptin 1 | ALWKTMLKKLGTMALHAGKAALGAAADTISQGTQ | 138 |
| Bactenecin 1 | RLCRIVVIRVCR | 139 |
| Thanatin | GSKKPVPIIYCNRRTGKCQRM | 140 |
| Brevinin 1T | VNPIILGVLPKVCLITKKC | 141 |
| Ranateurin 1 | SMLSVLKNLGKVGLGFVACKINIKQC | 142 |
| Esculentin 1 | GIFSKLGRKKIKNLLISGLKNVGKEVGMDVVRTGIKIAGCKIKGEC | 143 |
| Tachyplesin | RWCFRVCYRGICYRKCR | 144 |
| Androctonin | RSVCRQIKICRRRGGCYYKCTNRPY | 145 |
| alpha-defensin | DCYCRIPACIAGERRYGTCIYQGRLWAFCC | 146 |
| beta-defensin | NPVSCVRNKGICVPIRCPGSMKQIGTCVGRAVKCCRKK | 147 |
| theta-defensin | GFCRCLCRRGVCRCICTR | 148 |
| defensin (sapecin A) | ATCDLLSGTGINHSACAAHCLLRGNRGGYCNGKAVCVCRN | 149 |
| Thionin (crambin) | TTCCPSIVARSNFNVCRIPGTPEAICATYTGCIIIPGATCPGDYAN | 150 |
| defensin from radish | QKLCQRPSGTWSGVCGNNNACKNQCIRLEKARHGSCNYVFPAHCICYFPC | 151 |
| Drosomycin | DCLSGRYKGPCAVWDNETCRRVCKEEGRSSGHCSPSLKCWCEGC | 152 |
| Hepcidin | DTHFPICIFCCGCCHRSKCGMCCKT | 153 |
| Bac 5 | RFRPPIRRPPIRPPFYPPFRPPIRPPIFPPIRPPFRPPLGRPFP | 154 |
| PR-39 | RRRPRPPYLPRPRPPPFFPPRLPPRIPPGFPPRFPPRFP | 155 |
| Pyrrhocoricin | VDKGSYLPRPTPPRPIYNRN | 156 |
| Histatin 5 | DSHAKRHHGYKRKFHEKHHSHRGY | 157 |
| ECP19 | RPPQFTRAQWFAIQHISLN | 158 |
| MSI-594 | GIGKFLKKAKKGIGAVLKVLTTG | 159 |
| TL-ColM | METLTVHAPSPSTNLPSYGNGAFSLSAPHVPGAGP | 160 |
| SBO | KLKKIAQKIKNFFAKLVA | 161 |

In a further aspect of the present invention at least one of the additional amino acid sequence stretches may be a sushi peptide which is described by Ding J L, Li P, Ho B Cell Mol Life Sci. 2008 April; 65(7-8):1202-19. The Sushi peptides: structural characterization and mode of action against Gram-negative bacteria. Especially preferred is the sushi 1 peptide according to SEQ ID NO: 162.

Preferred sushi peptides are sushi peptides S1 and S3 and multiples thereof; FASEB J. 2000 September; 14(12):1801-13.

In a further aspect of the present invention at least one of the additional amino acid sequence stretches is a hydrophobic peptide, which comprises at least 90% of the hydrophobic amino acid residues of valine, isoleucine, leucine, methionine, phenylalanine, tryptophan, cysteine, alanine, tyrosine, proline and/or glycine. In another preferred embodiment the hydrophobic peptide fused to the protein of the invention consists of about 90% to about 95%, or of about 90% to about 100%, or of about 95% to about 100% of the hydrophobic amino acid residues of valine, isoleucine, leucine, methionine, phenylalanine, tryptophan, cysteine, alanine, tyrosine, proline and/or glycine.

Preferred hydrophobic peptides are Walmagh1 having the amino acid sequence according to SEQ ID NO: 163 and the hydrophobic peptide having the amino acid sequence Phe-Phe-Val-Ala-Pro (SEQ ID NO: 164).

In a further aspect of the present invention at least one of the additional amino acid sequence stretches is an amphipathic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, proline and/or glycine. Side chains of the amino acid residues are oriented in order that cationic and hydrophobic surfaces are clustered at opposite sides of the peptide. Preferably, more than about 30, 40, 50, 60 or 70% of the amino acids in said peptide are positively charged amino acids. Preferably, more than about 30, 40, 50, 60 or 70%, of the amino acid residues in said peptide are hydrophobic amino acid residues. Advantageously, the amphipathic peptide is present at the N-terminal or the C-terminal end of the polypeptide according to the present invention.

In another embodiment of the invention, the amphipathic peptide consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or at least 50 amino acid residues. In a preferred embodiment at least about 30, 40, 50, 60 or 70% of said amino acid residues of the amphipathic peptide are either arginine or lysine residues and/or at least about 30, 40, 50, 60 or 70% of said amino acid residues of the amphipathic peptide are of the hydrophobic amino acids valine, isoleucine, leucine, methionine, phenylalanine, tryptophan, cysteine, alanine, tyrosine, proline and/or glycine.

In another preferred embodiment of the present invention the amphipathic peptide stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. Preferred are amphipathic peptide stretches consisting of about 10% to about 50%, or about 20% to about 50%, or about 30% to about 45% or about 5% to about 30% positively charged amino acid residues, in particular lysine and/or arginine residues and of about 50% to about 85%, or about 50% to about 90%, or about 55% to about 90%, or about 60% to about 90%, or about 65% to about 90% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues. In another preferred embodiment amphipathic peptide stretches consisting of 12% to about 50% positively charged amino acid residues, in particular lysine and/or arginine residues and of about 50% to about 85% hydrophobic amino acid residues, valine, isoleucine, leucine, methionine, phenylalanine, tryptophan, cysteine, alanine, tyrosine, proline and glycine residues, more preferably alanine, valine, leucine, isoleucine, phenylalanine, and/or tryptophan residues.

Preferred amphipathic peptides are α4-helix of T4 lysozyme according to SEQ ID NO: 165 and WLBU2-Variant having the amino acid sequence according to SEQ ID NO: 166 and Walmagh 2 according to SEQ ID NO: 167.

In a preferred embodiment of the present invention the inventive polypeptide comprises two or more amino acid sequence stretches as defined herein. If the polypeptide according to the present invention comprises more than one of these additional amino acid sequence stretches, then it preferably comprises at least two distinct amino acid sequence stretches, preferably selected from the group of amphipathic peptide, cationic peptide, polycationic peptide, hydrophobic peptide, or naturally occurring antimicrobial peptide, like sushi peptide and defensin. The two or more amino acid sequence stretches, e.g. at the N- or C-terminus of the enzyme and/or at the N- or C-terminus of the polypeptide may thus be two or more distinct cationic peptides or two or more distinct polycationic peptides or two or more distinct antimicrobial peptides or two or more distinct amphipathic peptides or two or more distinct hydrophobic peptides. The two or more amino acid sequence stretches may in the alternative also be any combination of two or more peptides selected from different representatives of the group consisting of: cationic peptide, a polycationic peptide, a hydrophobic peptide, an antimicrobial peptide, a sushi peptide, a defensin and an amphipathic peptide. For example, a cationic peptide could be combined with an antimicrobial peptide.

The optional additional amino acid sequence stretches as specified above consist preferably of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred are those additional amino acid sequence stretches consisting of about 5 to about 100 amino acid residues, about 5 to about 50 or about 5 to about 30 amino acid residues. More preferred are peptide stretches consisting of about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

In a preferred embodiment the inventive polypeptide comprises at least one, two or more amino acid sequences stretches selected from the group consisting of KRK and SEQ ID NOs: 93-167. Preferably, the inventive polypeptide comprises at least one, two or more amino acid sequence stretches selected from the group consisting of KRK and SEQ ID NOs: 93-167, and an amino acid sequence selected from any one of SEQ ID NOs: 1 to 92, wherein preferably the amino acid sequence stretches, are fused to the N- and/or C-terminus of the amino acid sequence selected from the group consisting of SEQ ID NOs: 1 to 92.

The additional amino acid sequence stretches of the polypeptide comprised in the composition according to the present invention may be linked to the rest of the enzyme by intervening additional amino acid residues e.g. due to cloning reasons. Alternatively, the additional amino acid sequence stretches may be directly linked to the rest of the enzyme sequence without intervening linker sequences. The additional amino acid sequences, if more than one present in the inventive polypeptide and positioned on the same terminus of the enzyme, may likewise be linked to each other by additional intervening amino acid residues or may be directly joined to each other.

Preferably, said intervening additional amino acid residues may not be recognized and/or cleaved by proteases. Preferably said additional amino acid sequences are linked to each other and/or to the enzyme by at least 1, 2, 3, 4, 5, 6, 7, 8, 9 or 10 additional intervening amino acid residues.

In a preferred embodiment the at least one additional amino acid sequence stretch is linked to the rest of the inventive polypeptide, preferably at the N- or C-terminus of the polypeptide according to the present invention, by the additional intervening amino acid residues glycine, serine and serine (Gly-Ser-Ser), glycine, alanine, glycine and alanine (Gly-Ala-Gly-Ala; SEQ ID NO:168), glycine, alanine, glycine, alanine, glycine, alanine, glycine and alanine (Gly-Ala-Gly-Ala-Gly-Ala-Gly-Ala; SEQ ID NO:169) or glycine, alanine, glycine, alanine, glycine, alanine, glycine, alanine, glycine, alanine, glycine and alanine (Gly-Ala-Gly-Ala-Gly-Ala-Gly-Ala-Gly-Ala-Gly-Ala; SEQ ID NO:170).

In embodiments where there are at least two additional amino acid sequence stretches the first amino acid sequence may be linked to the N-terminus of the enzyme domain (i.e. the sequence providing the peptidoglycan degrading activity) by additional amino acid residues, in particular glycine and serine (Gly-Ser) and the second additional amino acid sequence may be linked to the N-terminus of the first additional amino acid sequence by additional amino acid residues, in particular glycine and serine (Gly-Ser) or glycine, serine and serine (Gly-Ser-Ser). Likewise, the first amino acid sequence stretch may be linked to the C-terminus of the enzyme domain by additional amino acid residues, in particular glycine and serine (Gly-Ser) and the second amino acid sequence stretch is linked to the C-terminus of the first amino acid sequence stretch by additional amino acid residues, in particular glycine and serine (Gly-Ser). In another embodiment the second amino acid sequence stretch is linked to the N- or C-terminus of the first amino acid sequence stretch by additional amino acid residues glycine, serine and serine (Gly-Ser-Ser), glycine, alanine, glycine and alanine (Gly-Ala-Gly-Ala; SEQ ID NO:168), glycine, alanine, glycine, alanine, glycine, alanine, glycine and alanine (Gly-Ala-Gly-Ala-Gly-Ala-Gly-Ala, SEQ ID NO:169) or glycine, alanine, glycine, alanine, glycine, alanine, glycine, alanine, glycine, alanine, glycine and alanine (Gly-Ala-Gly-Ala-Gly-Ala-Gly-Ala-Gly-Ala-Gly-Ala, SEQ ID NO:170).

Aside of the enzymatic domain (i.e. a domain having the activity of degrading the peptidoglycan of Gram-negative bacteria, such as SEQ ID NOs: 1 to 92 and fragments and derivatives thereof), and the optional additional amino acid sequence stretches, as defined herein, the inventive polypeptide may of course also comprise other amino acid sequence elements, e.g. one or more tags, e.g. a His-tag, Strep-tag, Avi-tag, Myc-tag, Gst-tag, JS-tag, cystein-tag, FLAG-tag or other tags known in the art, thioredoxin, maltose binding proteins (MBP) etc.

In this context, the inventive polypeptide, preferably having the ability of degrading the peptidoglycan layer of Gram negative bacteria such as Salmonella or Pseudomonas bacteria, may additional comprise a tag e.g. for purification. Preferred is a His$_6$-tag, preferably at the C-terminus and/or the N-terminus of the polypeptide according to the present invention. Said tag can be linked to the polypeptide by additional amino acid residues e.g. due to cloning reasons. Preferably said tag can be linked to the protein by at least 1, 2, 3, 4, 5, 6, 7, 8, 9 or 10 additional amino acid residues. Preferably said additional amino acid residues may not be recognized and/or cleaved by proteases. In a preferred embodiment the inventive polypeptide comprises a His$_6$-tag at its C-terminus linked to the polypeptide by the additional amino acid residues lysine and glycine (Lys-Gly) or leucine and glutamic acid (Leu-Glu). Preferably, said additional amino acid residues may be not recognized or cleaved by proteases. In another preferred embodiment the inventive polypeptide comprises a His$_6$-tag at its N-terminus linked to the polypeptide by the additional amino acid residues lysine and glycine (Lys-Gly) or leucine and glutamic acid (Leu-Glu). In another preferred embodiment the polypeptide comprises a His$_6$-tag at its N- and C-terminus linked to the polypeptide by the additional amino acid residues lysine and glycine (Lys-Gly) or leucine and glutamic acid (Leu-Glu).

A polypeptide according to the present invention can be produced by standard means known in the art, e.g. by recombinant expression of nucleic acids encoding the respective polypeptide in appropriate host cells. If the inventive polypeptide comprises for example additionally amino acid sequence stretches or tags etc., such fusion proteins may be produced by linking the required individual nucleic acid sequences using standard cloning techniques as described e.g. by Sambrook et al. 2001, Molecular Cloning: A Laboratory Manual. Such a polypeptide may be produced likewise with methods known in the art, e.g., in recombinant DNA expression systems.

It has to be noted that the inventive polypeptides having the activity of degrading the peptidoglycan layer of Gram negative bacteria can be assembled like using a tool box, i.e. any additional amino acid sequence stretch and antimicrobial peptide disclosed above may be included in the polypeptide according to the present invention. Consequently, it is possible to construct a suitable polypeptide for any Gram negative bacteria which should be eliminated. The most preferred genera of bacteria in the context of the present invention, i.e. for at least one of which the mentioned polypeptide has the activity of degrading the peptidoglycan layer are Salmonella, Escherichia, Acinetobacter, Vibrio and Pseudomonas.

In a further aspect the present invention relates to a nucleic acid encoding a polypeptide according to the present invention. The nucleic acid may be RNA or DNA. Examples for such nucleic acids are given in SEQ ID NO: 171-210. Consequently, in a further aspect the present invention also relates to a polypeptide encoded by a nucleic acid according to the present invention, e.g. a polypeptide comprising an amino acid sequence encoded by a nucleic acid selected from the group consisting of SEQ ID NOs: 171-210.

In a further aspect the present invention relates to a vector comprising a nucleic acid according to the present invention.

In a further aspect the present invention relates to a bacteriophage comprising a nucleic acid or polypeptide according to the present invention.

In a further aspect the present invention relates to a host cell comprising a polypeptide according to the present invention, a nucleic acid according to the present invention, and/or a vector according to the present invention. Particularly preferred host cells are yeast cells such as Pichia pastoris.

The present invention relates also to a composition comprising a polypeptide according to the present invention, a nucleic acid according to the present invention, a vector according to the present invention and/or a host cell according to the present invention. Such composition may for example be a pharmaceutical composition comprising a pharmaceutical acceptable diluent, excipient or carrier.

In a further aspect the present invention relates to a polypeptide according to the present invention, a nucleic acid according to the present invention, a vector according to the present invention, a host cell according to the present invention, and/or a composition according to the present invention for use in a method of treatment of the human or animal body by surgery or therapy or in diagnostic methods practiced on the human or animal body. In such scenarios the antibacterial activity of polypeptide of the present invention can be exploited, in particular if the optional at least one additional amino acid sequence stretch is available.

Such method typically comprises administering to a subject an effective amount of an inventive polypeptide, nucleic acid, vector, host cell or a composition. The subject may for example be a human or an animal. In particular, the inventive polypeptide, the inventive nucleic acid, the inventive vector, the inventive host cell, and/or the inventive composition may be used in methods for the treatment or prevention of Gram-negative bacterial infections. The method of treatment may comprise the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis, e.g. caused by Gram-negative bacteria, in particular by the Gram-negative bacteria as mentioned herein.

The dosage and route of administration used in a method of treatment (or prophylaxis) according to the present invention depends on the specific disease/site of infection to be treated. The route of administration may be for example oral, topical, nasopharyngeal, parenteral, intravenous, rectal or any other route of administration.

For application of an inventive polypeptide, nucleic acid, vector, host cell or composition to a site of infection (or site endangered to be infected) a formulation may be used that protects the active compounds from environmental influences such as proteases, oxidation, immune response etc., until it reaches the site of infection. Therefore, the formulation may be capsule, dragee, pill, suppository, injectable solution or any other medical reasonable galenic formulation. Preferably, the galenic formulation may comprise suitable carriers, stabilizers, flavourings, buffers or other suitable reagents. For example, for topical application the formulation may be a lotion or plaster, for nasopharyngeal application the formulation may be saline solution to be applied via a spray to the nose.

Preferably, an inventive polypeptide, nucleic acid, vector, host cell or composition is used for medical treatment, if the infection to be treated (or prevented) is caused by multiresistant bacterial strains, in particular by strains resistant against one or more of the following antibiotics: streptomycin, tetracycline, cephalothin, gentamicin, cefotaxime, cephalosporin, ceftazidime or imipenem. Furthermore, an inventive polypeptide, nucleic acid, vector, host cell or composition can be used in methods of treatment by administering it in combination with conventional antibacterial agents, such as antibiotics, lantibiotics, bacteriocins or endolysins, etc.

The present invention also relates to a pharmaceutical pack comprising one or more compartments, wherein at least one compartment comprises an inventive polypeptide, nucleic acid, vector, host cell or composition.

In another aspect the present invention relates to a process of preparation of a pharmaceutical composition, said process comprising admixing one or more an inventive polypeptide, nucleic acid, vector, host cell or composition with a pharmaceutically acceptable diluent, excipient or carrier.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the inventive polypeptide, nucleic acid, vector, host cell and/or composition in order to degrade already existing or freshly settling pathogenic Gram-negative bacteria.

In a further aspect the present invention relates to the inventive polypeptide, nucleic acid, vector, host cell or composition for use as diagnostic means in medicinal, food or feed or environmental diagnostics, in particular as a diagnostic means for the diagnostic of bacteria infection caused in particular by Gram-negative bacteria. In this respect the inventive polypeptide, nucleic acid, vector, host cell or composition may be used as a tool to specifically degrade the peptidoglycan of pathogenic bacteria, in particular of Gram-negative pathogenic bacteria. The degradation of the bacterial cells by the inventive polypeptide, nucleic acid, vector, host cell or composition can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains).

In a further aspect the present invention relates to the use of the inventive polypeptide, the inventive nucleic acid, the inventive vector, the inventive host cell, and/or the inventive composition, as an antimicrobial in food or feed, or in cosmetics, as disinfecting agent or in the environmental field. They can be used in particular for the treatment or prevention of Gram-negative bacterial contamination of foodstuff, of food processing equipment, of food processing plants, of surfaces coming into contact with foodstuff, feedstuff, of feed processing equipment, of feed processing plants, of surfaces coming into contact with feedstuff (such as shelves and food and feed deposit areas), of medical devices, or of surfaces in hospitals and surgeries.

In particular, an inventive polypeptide, nucleic acid, vector, host cell or composition may be used prophylactically as sanitizing agent. Said sanitizing agent may be used before or after surgery, or for example during hemodialysis. Moreover, premature infants and immunocompromised persons, or those subjects with need for prosthetic devices may be treated with an inventive polypeptide, nucleic acid, vector, host cell or composition. Said treatment may be either prophylactically or during acute infection. In the same context, nosocomial infections, especially by antibiotic resistant strains like *Pseudomonas aeruginosa* (FQRP), *Acinetobacter* species and Enterobacteriaceae such as *E. coli, Salmonella, Shigella, Citrobacter, Edwardsiella, Enterobacter, Hafnia, Klebsiella, Morganella, Proteus, Providencia, Serratia* and *Yersinia* species may be treated prophylactically or during acute phase with an inventive polypeptide, nucleic acid, vector, host cell or composition. Therefore, an inventive polypeptide, nucleic acid, vector, host cell or composition may be used as a disinfectant also in combination with other ingredients useful in a disinfecting solution like detergents, tensids, solvents, antibiotics, lantibiotics, or bacteriocins.

It should be understood that the detailed description and specific examples disclosed herein, indicating particular embodiments of the invention, are given by way of illustration only, since various changes and modifications within the spirit and scope of the invention will become apparent to those skilled in the art from this description.

EXAMPLES

In the following, specific examples illustrating various embodiments and aspects of the invention are presented.

However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1

Enzymatic Activity in the Muralytic Test

1. Cell Preparation

Cells (*E. coli* 018) of an overnight culture were centrifuged at 4500 g for 10 min. The cell pellet was resuspended in $ChCl_3$ buffer (20 mM HEPES, 150 mM NaCl, $ChCl_3$-saturated, pH 7.4) and incubated for 45 min at room temperature. Thereafter the cells were centrifuged again at 4500 g for 10 min, and washed with buffer (20 mM HEPES, 150 mM NaCl, pH 7.4). Next, the cell pellet was resuspended again in buffer (20 mM HEPES, 150 mM NaCl, pH 7.4) in a volume yielding an $OD_{600}$ of approx. 1. The cell suspension was transferred into 1 ml vials and afterwards centrifuged at 4500 g for 10 min. The supernatant was discarded and the pellets were stored at −20° C.

2. Measurement of Enzymatic Activity

Cell pellets were resuspended in 20 mM HEPES, pH 7.4, and transferred into a cuvette. Protein solution in an amount yielding a final concentration of 0.005, 1 or 2 µM was added. The final volume of cell and protein solution was 1 ml. For control measurements without protein solution a respective volume of protein buffer (20 mM HEPES, 500 mM NaCl, pH 7.4) was added. Cells and protein were rapidly mixed and the $OD_{600}$ was measured for 30 min.

3. Measurements

The following measurements were carried out:

TABLE 5

| SEQ ID NO: | Fragment | Protein concentration [µM] |
|---|---|---|
| 50 | 1-115 | 2 |
| 52 | 1-125 | 2 |
| 54 | 1-135 | 2 |
| 56 | 1-145 | 2 |
| 58 | 1-148 | 2 |
| 60 | 1-151 | 1 |
| 62 | 1-161 | 1 |
| 64 | 1-166 | 0.005 |
| 66 | 1-177 | 1 |
| 68 | 1-182 | 0.005 |
| 70 | 5-166 | 2 |
| 90 | 5-187 | 0.005 |
| 72 | 5-177 | 2 |
| 74 | 10-151 | 2 |
| 76 | 10-166 | 2 |
| 78 | 10-177 | 2 |
| 80 | 18-151 | 2 |
| 82 | 42-187 | 2 |
| 84 | 50-187 | 2 |
| 86 | 21-187 | 2 |
| 92 | 1-187 | 0.005 |

For the full length enzyme and larger fragments a very low concentration of protein was used (0.005 µM), smaller fragments were tested at higher protein concentrations (1 or 2 µM). All proteins of table 5 showed enzymatic activity.

Example 2

Enzymatic Activity in the Muralytic Test for *Salmonella*

The same test as mentioned above in Example 1 was also conducted with Chloroform-treated *Salmonella typhimurium* (DSMZ 17058) and the polypeptide of SEQ ID NO: 92. The final concentration of enzyme was 0.005 µM. The enzyme was active.

Example 3

Comparative Test

The same test as mentioned above in Example 1 was also conducted for comparing the activity of the endolysin of the invention (SEQ ID NO: 92) with endolysins from the art in *E. coli* (O157:H7): KZ144 (SEQ ID NO: 226), OBPgpLYS (SEQ ID NO: 227) and PVPSEgp146 (SEQ ID NO: 228). The final concentrations of the enzymes were 2 µM. The polypeptides were active.

Example 4

Enzymatic Activity of Fusion Proteins in Minimal Inhibitory Concentration (MIC) Experiments 1. General Protocol An overnight culture, in eg. LB medium, of the respective bacteria is diluted 1:10 in Mueller-Hinton-broth. Said dilution is incubated at 37° C. up to $OD_{600}$=0.6 (around $10^9$ cfu/ml). The bacteria are mixed in a micro titer plate, optionally with a solution containing EDTA, buffer (20 mM HEPES, 500 mM NaCl, pH 7.4) and the respective fusion protein in different concentrations (determined as µg/ml final concentration in the Mueller-Hinton-broth) yielding a bacterial amount of $2\times10^5$-$8\times10^5$ cfu/ml. The mixture is incubated overnight at 37° C. Bacterial growth is determined photometrically at 600 nm after 18-20 h. The MIC is the concentration of the one tube having the lowest concentration of fusion protein and in parallel showing no bacterial growth.

1. *Escherichia coli*

Fusion proteins composed of the endolysin of the invention, SEQ ID NO: 92, with various peptides where tested. In table 6 the MIC (minimal inhibitory concentration) for such fusions on *Escherichia coli* (O18ab:H14) is shown.

TABLE 6

| Peptide name | SEQ ID NO: Peptide | Peptide position | SEQ ID NO: Fusion protein | MIC O18ab:H14 |
|---|---|---|---|---|
| Buforin II | 127 | N | 211 | 2 |
| SMAP29 | 119 | N | 212 | 2 |
| Melittin | 134 | N | 213 | 6 |
| Pleuricidin | 124 | N | 214 | 1 |
| ECP19 | 158 | N | 215 | 6.5 |
| MSI-594 | 159 | N | 216 | 2 |
| Sarcotoxin IA | 128 | N | 217 | 2 |
| Cecropin A (*A. aeg*) | 125 | N | 218 | 2 |
| TL-ColM | 160 | N | 219 | 4 |
| SBO | 161 | C | 220 | 2 |
| Apidaecin | 129 | C | 221 | 6 |
| Melittin | 134 | C | 222 | 6 |
| Indolicidin | 120 | C | 223 | 2 |
| Pyrrhocoricin | 156 | C | 224 | 8 |

TABLE 6-continued

| Peptide name | SEQ ID NO: Peptide | Peptide position | SEQ ID NO: Fusion protein | MIC O18ab:H14 |
|---|---|---|---|---|
| Controls | | | | |
| w/o fusion | | | 92 | 8 |
| Fusion of SMAP-29 and KZ144 endolysin | | | 225 | 3 |

"Peptide position" indicates presence of the peptide N-terminal of the endolysin (N) or C-terminal thereof (C).

2. Vibrio parahaemolyticus

Fusion proteins composed of the endolysin of the invention, SEQ ID NO: 92, with various peptides where tested. In table 7 the MIC (minimal inhibitory concentration) for such fusions on 5 strains of *Vibrio parahaemolyticus* (Farmer1, 1D, 2HP, 3HP, 5HP) in 2.5 mM EDTA is shown.

TABLE 7

| Peptide name | SEQ ID NO: Fusion protein | MIC Farmer1 | MIC 1D | MIC 2HP | MIC 3HP | MIC 5HP |
|---|---|---|---|---|---|---|
| Buforin II | 211 | <2.5 | 7.5 | 5 | <2.5 | 5 |
| SMAP29 | 212 | 7.3 | 9.7 | 7.3 | 4.8 | 7.3 |
| Melittin | 213 | <2.6 | 7.8 | <2.6 | <2.6 | 7.8 |
| Pleuricidin | 214 | <2.2 | 3.3 | <1.1 | <1.1 | <1.1 |
| ECP19 | 215 | <2.5 | <2.5 | <2.5 | <2.5 | <2.5 |
| MSI-594 | 216 | <2.5 | <2.5 | <2.5 | 5 | 5 |
| Sarcotoxin IA | 217 | 5 | <2.5 | 10 | 12.5 | 5 |
| Cecropin A (A. aeg) | 218 | <2.5 | <2.5 | 5 | 5 | 10 |
| SBO | 220 | 5 | <2.5 | 5 | 5 | 5 |
| Apidaecin | 221 | 12.5 | <2.5 | 5 | <2.5 | 10 |
| Melittin | 222 | 20 | 5 | 5 | 5 | 7.5 |
| Indolicidin | 223 | 25 | <2.5 | 5 | <2.5 | 5 |
| Pyrrhocoricin | 224 | 5 | 5 | 7.5 | 5 | 10 |
| Controls | | | | | | |
| w/o | 92 | 10 | 7.5 | 7.5 | 7.5 | 5 |
| SMAP-29-KZ144 | 225 | 7.5 | <2.5 | 7.5 | 5 | <2.5 |

3. Pseudomonas aeruginosa

Fusion proteins composed of the endolysin of the invention, SEQ ID NO:92, with various peptides where tested. In table 8 the MIC (minimal inhibitory concentration) for such fusions on *Pseudomonas aeruginosa* (PAO1p) in 500 µM EDTA is shown.

TABLE 8

| Peptide name | SEQ ID NO: Fusion protein | MIC PAO1p |
|---|---|---|
| SMAP29 | 212 | 9 |
| Pleuricidin | 214 | >13 |
| MSI-594 | 216 | 12-15 |
| Cecropin A (A. aeg) | 218 | 12 |
| SBO | 220 | 24-28 |
| Control | | |
| SMAP-29-KZ144 | 225 | 2-4 |

4. A. baumannii

Fusion proteins composed of the endolysin of the invention, SEQ ID NO: 92, with various peptides where tested. In table 9 the MIC (minimal inhibitory concentration) for such fusions on *A. baumannii* (S139) is shown.

TABLE 9

| Peptide name | SEQ ID NO: Fusion protein | MIC S139 |
|---|---|---|
| SMAP29 | 212 | 20-22 |
| MSI-594 | 216 | 16 |
| Cecropin A (A. aeg) | 218 | 14-18 |
| Control | | |
| SMAP-29-KZ144 | 225 | 12 |

---

The invention claimed is:

1. A polypeptide comprising an amino sequence selected from the group consisting of:
   a) SEQ ID NO: 1, and
   b) a fragment of a), wherein the fragment is at most 20 amino acids shorter than SEQ ID NO: 1,
wherein the polypeptide further comprises at least one heterologous amino acid sequence selected from the group consisting of amphipathic peptide, cationic peptide, polycationic peptide, hydrophobic peptide, or naturally-occurring antimicrobial peptide.

2. The polypeptide according to claim 1, wherein the polypeptide degrades the peptidoglycan of Gram-negative bacteria.

3. The polypeptide according to claim 1, wherein the fragment comprises a sequence selected from the group consisting of SEQ ID NO: 3, 5 and 7.

4. The polypeptide according to claim 1, wherein the polypeptide comprises a fragment of SEQ ID NO: 1 and is further characterized by a sequence selected from the group consisting of SEQ ID NO: 9, 10, 11 and 12.

5. The polypeptide according to claim 1, wherein the polypeptide comprises a sequence selected from the group of sequences consisting of SEQ ID NO: 13 to 91.

6. The polypeptide according to claim 1, wherein the polypeptide comprises an amino sequence selected from the group consisting of:
   a1) SEQ ID NO: 2,
   b1) SEQ ID NO: 45,
   c1) SEQ ID NO: 46,
   d1) SEQ ID NO: 47,
   e1) SEQ ID NO: 48,
   f1) SEQ ID NO: 63,
   g1) SEQ ID NO: 64,
   h1) SEQ ID NO: 65,
   i1) SEQ ID NO: 66,
   j1) SEQ ID NO: 68,
   k1) SEQ ID NO: 67,
   l1) SEQ ID NO: 85,
   m1) SEQ ID NO: 86,
   n1) SEQ ID NO: 87,
   o1) SEQ ID NO: 88,
   p1) SEQ ID NO: 89,
   q1) SEQ ID NO: 90,
   r1) SEQ ID NO: 91,
   s1) SEQ ID NO: 92, and
   t1) a fragment of any of a1) to s1).

7. The polypeptide according to claim 1, wherein the polypeptide comprises an amino sequence selected from the group consisting:
   a2) SEQ ID NO: 91, and
   b2) a fragment of a2).

8. The polypeptide according to claim 7, wherein the polypeptide degrades the peptidoglycan of Gram-negative bacteria.

9. The polypeptide according to claim 1, wherein the at least one heterologous amino acid sequence is present at the N- or C-terminus of the polypeptide.

10. The polypeptide according to claim 1, wherein the polypeptide comprises at least one heterologous amino acid sequence selected from the group consisting of: KRK and SEQ ID NOs: 93-167.

11. The polypeptide according to claim 1, wherein the polypeptide comprises a methionine residue at the N-terminus and/or a tag.

12. The polypeptide according to claim 1, wherein the polypeptide comprises an amino acid sequence as encoded by a nucleic acid sequence according to any one of SEQ ID NOs: 171-210.

13. A nucleic acid encoding a polypeptide according to claim 1.

14. A vector comprising a nucleic acid according to claim 13.

15. A host cell comprising a nucleic acid according to claim 13.

16. A composition comprising a polypeptide according to claim 1.

17. The composition according to claim 16, wherein the composition is a pharmaceutical composition comprising a pharmaceutical acceptable diluent, excipient or carrier a foodstuff or feed, or a cosmetic.

18. A method of treating a Gram-negative bacterial infection in a subject comprising providing to said subject a polypeptide according to claim 1.

19. A method of disinfecting an environmental field comprising contacting said environmental field with a polypeptide according to claim 1.

20. The polypeptide according to claim 2, wherein the polypeptide degrades the peptidoglycan of *Escherichia, Acinetobacter, Vibrio, Pseudomonas* and/or of *Salmonella* bacteria.

21. The polypeptide according to claim 8, wherein the polypeptide degrades the peptidoglycan of *Escherichia, Acinetobacter, Vibrio, Pseudomonas* and/or of *Salmonella* bacteria.

22. The polypeptide according to claim 1, wherein the naturally-occurring antimicrobial peptide is a sushi peptide or a defensin.

* * * * *

SEQUENCE LISTING

<160> NUMBER OF SEQ ID NOS: 228

<210> SEQ ID NO 1
<211> LENGTH: 84
<212> TYPE: PRT
<213> ORGANISM: Artificial Sequence
<220> FEATURE:
<223> OTHER INFORMATION: peptidoglycan degrading enzyme

<400> SEQUENCE: 1

Ile Leu Tyr Glu Arg His Ile Met Ala Arg Leu Leu Lys Ala Lys Gly
1               5                   10                  15

Val Pro Ile Ala Gly Leu Pro Ser Asp Leu Val Asn Thr Thr Pro Gly
            20                  25                  30

Gly Tyr Gly Lys Phe Ser Glu Gln His Gly Lys Leu Asp Arg Ala Val
        35                  40                  45

Lys Ile Asp Arg Glu Cys Ala Leu Gln Ser Cys Ser Trp Gly Met Phe
    50                  55                  60

Gln Leu Met Gly Phe Asn Tyr Lys Leu Cys Gly Tyr Ala Thr Val Gln
65                  70                  75                  80

Ala Phe Val Asn

```
<210> SEQ ID NO 2
<211> LENGTH: 85
<212> TYPE: PRT
<213> ORGANISM: Artificial Sequence
<220> FEATURE:
<223> OTHER INFORMATION: peptidoglycan degrading enzyme

<400> SEQUENCE: 2

Met Ile Leu Tyr Glu Arg His Ile Met Ala Arg Leu Leu Lys Ala Lys
1               5                   10                  15

Gly Val Pro Ile Ala Gly Leu Pro Ser Asp Leu Val Asn Thr Thr Pro
            20                  25                  30

Gly Gly Tyr Gly Lys Phe Ser Glu Gln His Gly Lys Leu Asp Arg Ala
        35                  40                  45

Val Lys Ile Asp Arg Glu Cys Ala Leu Gln Ser Cys Ser Trp Gly Met
    50                  55                  60

Phe Gln Leu Met Gly Phe Asn Tyr Lys Leu Cys Gly Tyr Ala Thr Val
65                  70                  75                  80

Gln Ala Phe Val Asn
                85

<210> SEQ ID NO 3
<211> LENGTH: 66
<212> TYPE: PRT
<213> ORGANISM: Artificial Sequence
<220> FEATURE:
<223> OTHER INFORMATION: peptidoglycan degrading enzyme

<400> SEQUENCE: 3

Ala Arg Leu Leu Lys Ala Lys Gly Val Pro Ile Ala Gly Leu Pro Ser
1               5                   10                  15

Asp Leu Val Asn Thr Thr Pro Gly Gly Tyr Gly Lys Phe Ser Glu Gln
            20                  25                  30

His Gly Lys Leu Asp Arg Ala Val Lys Ile Asp Arg Glu Cys Ala Leu
        35                  40                  45

Gln Ser Cys Ser Trp Gly Met Phe Gln Leu Met Gly Phe Asn Tyr Lys
    50                  55                  60

Leu Cys
65

<210> SEQ ID NO 4
<211> LENGTH: 67
<212> TYPE: PRT
<213> ORGANISM: Artificial Sequence
<220> FEATURE:
<223> OTHER INFORMATION: peptidoglycan degrading enzyme

<400> SEQUENCE: 4

Met Ala Arg Leu Leu Lys Ala Lys Gly Val Pro Ile Ala Gly Leu Pro
1               5                   10                  15

Ser Asp Leu Val Asn Thr Thr Pro Gly Gly Tyr Gly Lys Phe Ser Glu
            20                  25                  30

Gln His Gly Lys Leu Asp Arg Ala Val Lys Ile Asp Arg Glu Cys Ala
        35                  40                  45

Leu Gln Ser Cys Ser Trp Gly Met Phe Gln Leu Met Gly Phe Asn Tyr
    50                  55                  60

Lys Leu Cys
65

<210> SEQ ID NO 5
```

<211> LENGTH: 76
<212> TYPE: PRT
<213> ORGANISM: Artificial Sequence
<220> FEATURE:
<223> OTHER INFORMATION: peptidoglycan degrading enzyme

<400> SEQUENCE: 5

```
Ala Arg Leu Leu Lys Ala Lys Gly Val Pro Ile Ala Gly Leu Pro Ser
1               5                   10                  15

Asp Leu Val Asn Thr Thr Pro Gly Gly Tyr Gly Lys Phe Ser Glu Gln
            20                  25                  30

His Gly Lys Leu Asp Arg Ala Val Lys Ile Asp Arg Glu Cys Ala Leu
        35                  40                  45

Gln Ser Cys Ser Trp Gly Met Phe Gln Leu Met Gly Phe Asn Tyr Lys
    50                  55                  60

Leu Cys Gly Tyr Ala Thr Val Gln Ala Phe Val Asn
65                  70                  75
```

<210> SEQ ID NO 6
<211> LENGTH: 77
<212> TYPE: PRT
<213> ORGANISM: Artificial Sequence
<220> FEATURE:
<223> OTHER INFORMATION: peptidoglycan degrading enzyme

<400> SEQUENCE: 6

```
Met Ala Arg Leu Leu Lys Ala Lys Gly Val Pro Ile Ala Gly Leu Pro
1               5                   10                  15

Ser Asp Leu Val Asn Thr Thr Pro Gly Gly Tyr Gly Lys Phe Ser Glu
            20                  25                  30

Gln His Gly Lys Leu Asp Arg Ala Val Lys Ile Asp Arg Glu Cys Ala
        35                  40                  45

Leu Gln Ser Cys Ser Trp Gly Met Phe Gln Leu Met Gly Phe Asn Tyr
    50                  55                  60

Lys Leu Cys Gly Tyr Ala Thr Val Gln Ala Phe Val Asn
65                  70                  75
```

<210> SEQ ID NO 7
<211> LENGTH: 74
<212> TYPE: PRT
<213> ORGANISM: Artificial Sequence
<220> FEATURE:
<223> OTHER INFORMATION: peptidoglycan degrading enzyme

<400> SEQUENCE: 7

```
Ile Leu Tyr Glu Arg His Ile Met Ala Arg Leu Leu Lys Ala Lys Gly
1               5                   10                  15

Val Pro Ile Ala Gly Leu Pro Ser Asp Leu Val Asn Thr Thr Pro Gly
            20                  25                  30

Gly Tyr Gly Lys Phe Ser Glu Gln His Gly Lys Leu Asp Arg Ala Val
        35                  40                  45

Lys Ile Asp Arg Glu Cys Ala Leu Gln Ser Cys Ser Trp Gly Met Phe
    50                  55                  60

Gln Leu Met Gly Phe Asn Tyr Lys Leu Cys
65                  70
```

<210> SEQ ID NO 8
<211> LENGTH: 75
<212> TYPE: PRT
<213> ORGANISM: Artificial Sequence
<220> FEATURE:

<223> OTHER INFORMATION: peptidoglycan degrading enzyme

<400> SEQUENCE: 8

Met Ile Leu Tyr Glu Arg His Ile Met Ala Arg Leu Leu Lys Ala Lys
1               5                   10                  15

Gly Val Pro Ile Ala Gly Leu Pro Ser Asp Leu Val Asn Thr Thr Pro
            20                  25                  30

Gly Gly Tyr Gly Lys Phe Ser Glu Gln His Gly Lys Leu Asp Arg Ala
        35                  40                  45

Val Lys Ile Asp Arg Glu Cys Ala Leu Gln Ser Cys Ser Trp Gly Met
    50                  55                  60

Phe Gln Leu Met Gly Phe Asn Tyr Lys Leu Cys
65                  70                  75

<210> SEQ ID NO 9
<211> LENGTH: 86
<212> TYPE: PRT
<213> ORGANISM: Artificial Sequence
<220> FEATURE:
<223> OTHER INFORMATION: peptidoglycan degrading enzyme

<400> SEQUENCE: 9

Ala Arg Leu Leu Lys Ala Lys Gly Val Pro Ile Ala Gly Leu Pro Ser
1               5                   10                  15

Asp Leu Val Asn Thr Thr Pro Gly Gly Tyr Gly Lys Phe Ser Glu Gln
            20                  25                  30

His Gly Lys Leu Asp Arg Ala Val Lys Ile Asp Arg Glu Cys Ala Leu
        35                  40                  45

Gln Ser Cys Ser Trp Gly Met Phe Gln Leu Met Gly Phe Asn Tyr Lys
    50                  55                  60

Leu Cys Gly Tyr Ala Thr Val Gln Ala Phe Val Asn Ala Met Tyr Lys
65                  70                  75                  80

Ser Glu Asp Glu Gln Leu
            85

<210> SEQ ID NO 10
<211> LENGTH: 87
<212> TYPE: PRT
<213> ORGANISM: Artificial Sequence
<220> FEATURE:
<223> OTHER INFORMATION: peptidoglycan degrading enzyme

<400> SEQUENCE: 10

Met Ala Arg Leu Leu Lys Ala Lys Gly Val Pro Ile Ala Gly Leu Pro
1               5                   10                  15

Ser Asp Leu Val Asn Thr Thr Pro Gly Gly Tyr Gly Lys Phe Ser Glu
            20                  25                  30

Gln His Gly Lys Leu Asp Arg Ala Val Lys Ile Asp Arg Glu Cys Ala
        35                  40                  45

Leu Gln Ser Cys Ser Trp Gly Met Phe Gln Leu Met Gly Phe Asn Tyr
    50                  55                  60

Lys Leu Cys Gly Tyr Ala Thr Val Gln Ala Phe Val Asn Ala Met Tyr
65                  70                  75                  80

Lys Ser Glu Asp Glu Gln Leu
            85

<210> SEQ ID NO 11
<211> LENGTH: 95
<212> TYPE: PRT

```
<213> ORGANISM: Artificial Sequence
<220> FEATURE:
<223> OTHER INFORMATION: peptidoglycan degrading enzyme

<400> SEQUENCE: 11

Ile Lys Ala Ile Ala Ser Val Glu Thr Lys Gly Ser Ala Trp Ile Thr
1               5                   10                  15

Pro Gly Val Pro Gln Ile Leu Tyr Glu Arg His Ile Met Ala Arg Leu
            20                  25                  30

Leu Lys Ala Lys Gly Val Pro Ile Ala Gly Leu Pro Ser Asp Leu Val
        35                  40                  45

Asn Thr Thr Pro Gly Gly Tyr Gly Lys Phe Ser Glu Gln His Gly Lys
    50                  55                  60

Leu Asp Arg Ala Val Lys Ile Asp Arg Glu Cys Ala Leu Gln Ser Cys
65                  70                  75                  80

Ser Trp Gly Met Phe Gln Leu Met Gly Phe Asn Tyr Lys Leu Cys
                85                  90                  95

<210> SEQ ID NO 12
<211> LENGTH: 96
<212> TYPE: PRT
<213> ORGANISM: Artificial Sequence
<220> FEATURE:
<223> OTHER INFORMATION: peptidoglycan degrading enzyme

<400> SEQUENCE: 12

Met Ile Lys Ala Ile Ala Ser Val Glu Thr Lys Gly Ser Ala Trp Ile
1               5                   10                  15

Thr Pro Gly Val Pro Gln Ile Leu Tyr Glu Arg His Ile Met Ala Arg
            20                  25                  30

Leu Leu Lys Ala Lys Gly Val Pro Ile Ala Gly Leu Pro Ser Asp Leu
        35                  40                  45

Val Asn Thr Thr Pro Gly Gly Tyr Gly Lys Phe Ser Glu Gln His Gly
    50                  55                  60

Lys Leu Asp Arg Ala Val Lys Ile Asp Arg Glu Cys Ala Leu Gln Ser
65                  70                  75                  80

Cys Ser Trp Gly Met Phe Gln Leu Met Gly Phe Asn Tyr Lys Leu Cys
                85                  90                  95

<210> SEQ ID NO 13
<211> LENGTH: 94
<212> TYPE: PRT
<213> ORGANISM: Artificial Sequence
<220> FEATURE:
<223> OTHER INFORMATION: peptidoglycan degrading enzyme

<400> SEQUENCE: 13

Ile Leu Tyr Glu Arg His Ile Met Ala Arg Leu Leu Lys Ala Lys Gly
1               5                   10                  15

Val Pro Ile Ala Gly Leu Pro Ser Asp Leu Val Asn Thr Thr Pro Gly
            20                  25                  30

Gly Tyr Gly Lys Phe Ser Glu Gln His Gly Lys Leu Asp Arg Ala Val
        35                  40                  45

Lys Ile Asp Arg Glu Cys Ala Leu Gln Ser Cys Ser Trp Gly Met Phe
    50                  55                  60

Gln Leu Met Gly Phe Asn Tyr Lys Leu Cys Gly Tyr Ala Thr Val Gln
65                  70                  75                  80

Ala Phe Val Asn Ala Met Tyr Lys Ser Glu Asp Glu Gln Leu
                85                  90
```

<210> SEQ ID NO 14
<211> LENGTH: 95
<212> TYPE: PRT
<213> ORGANISM: Artificial Sequence
<220> FEATURE:
<223> OTHER INFORMATION: peptidoglycan degrading enzyme

<400> SEQUENCE: 14

Met Ile Leu Tyr Glu Arg His Ile Met Ala Arg Leu Leu Lys Ala Lys
1               5                   10                  15

Gly Val Pro Ile Ala Gly Leu Pro Ser Asp Leu Val Asn Thr Thr Pro
            20                  25                  30

Gly Gly Tyr Gly Lys Phe Ser Glu Gln His Gly Lys Leu Asp Arg Ala
        35                  40                  45

Val Lys Ile Asp Arg Glu Cys Ala Leu Gln Ser Cys Ser Trp Gly Met
50                  55                  60

Phe Gln Leu Met Gly Phe Asn Tyr Lys Leu Cys Gly Tyr Ala Thr Val
65                  70                  75                  80

Gln Ala Phe Val Asn Ala Met Tyr Lys Ser Glu Asp Glu Gln Leu
                85                  90                  95

<210> SEQ ID NO 15
<211> LENGTH: 104
<212> TYPE: PRT
<213> ORGANISM: Artificial Sequence
<220> FEATURE:
<223> OTHER INFORMATION: peptidoglycan degrading enzyme

<400> SEQUENCE: 15

Ile Leu Tyr Glu Arg His Ile Met Ala Arg Leu Leu Lys Ala Lys Gly
1               5                   10                  15

Val Pro Ile Ala Gly Leu Pro Ser Asp Leu Val Asn Thr Thr Pro Gly
            20                  25                  30

Gly Tyr Gly Lys Phe Ser Glu Gln His Gly Lys Leu Asp Arg Ala Val
        35                  40                  45

Lys Ile Asp Arg Glu Cys Ala Leu Gln Ser Cys Ser Trp Gly Met Phe
50                  55                  60

Gln Leu Met Gly Phe Asn Tyr Lys Leu Cys Gly Tyr Ala Thr Val Gln
65                  70                  75                  80

Ala Phe Val Asn Ala Met Tyr Lys Ser Glu Asp Glu Gln Leu Asn Ala
                85                  90                  95

Phe Val Gly Phe Ile Lys Ser Asn
            100

<210> SEQ ID NO 16
<211> LENGTH: 105
<212> TYPE: PRT
<213> ORGANISM: Artificial Sequence
<220> FEATURE:
<223> OTHER INFORMATION: peptidoglycan degrading enzyme

<400> SEQUENCE: 16

Met Ile Leu Tyr Glu Arg His Ile Met Ala Arg Leu Leu Lys Ala Lys
1               5                   10                  15

Gly Val Pro Ile Ala Gly Leu Pro Ser Asp Leu Val Asn Thr Thr Pro
            20                  25                  30

Gly Gly Tyr Gly Lys Phe Ser Glu Gln His Gly Lys Leu Asp Arg Ala
        35                  40                  45

```
Val Lys Ile Asp Arg Glu Cys Ala Leu Gln Ser Cys Ser Trp Gly Met
 50                  55                  60

Phe Gln Leu Met Gly Phe Asn Tyr Lys Leu Cys Gly Tyr Ala Thr Val
 65                  70                  75                  80

Gln Ala Phe Val Asn Ala Met Tyr Lys Ser Glu Asp Glu Gln Leu Asn
                 85                  90                  95

Ala Phe Val Gly Phe Ile Lys Ser Asn
            100                 105
```

<210> SEQ ID NO 17
<211> LENGTH: 107
<212> TYPE: PRT
<213> ORGANISM: Artificial Sequence
<220> FEATURE:
<223> OTHER INFORMATION: peptidoglycan degrading enzyme

<400> SEQUENCE: 17

```
Ile Leu Tyr Glu Arg His Ile Met Ala Arg Leu Leu Lys Ala Lys Gly
 1               5                  10                  15

Val Pro Ile Ala Gly Leu Pro Ser Asp Leu Val Asn Thr Thr Pro Gly
                 20                  25                  30

Gly Tyr Gly Lys Phe Ser Glu Gln His Gly Lys Leu Asp Arg Ala Val
             35                  40                  45

Lys Ile Asp Arg Glu Cys Ala Leu Gln Ser Cys Ser Trp Gly Met Phe
 50                  55                  60

Gln Leu Met Gly Phe Asn Tyr Lys Leu Cys Gly Tyr Ala Thr Val Gln
 65                  70                  75                  80

Ala Phe Val Asn Ala Met Tyr Lys Ser Glu Asp Glu Gln Leu Asn Ala
                 85                  90                  95

Phe Val Gly Phe Ile Lys Ser Asn Leu Gln Leu
            100                 105
```

<210> SEQ ID NO 18
<211> LENGTH: 108
<212> TYPE: PRT
<213> ORGANISM: Artificial Sequence
<220> FEATURE:
<223> OTHER INFORMATION: peptidoglycan degrading enzyme

<400> SEQUENCE: 18

```
Met Ile Leu Tyr Glu Arg His Ile Met Ala Arg Leu Leu Lys Ala Lys
 1               5                  10                  15

Gly Val Pro Ile Ala Gly Leu Pro Ser Asp Leu Val Asn Thr Thr Pro
                 20                  25                  30

Gly Gly Tyr Gly Lys Phe Ser Glu Gln His Gly Lys Leu Asp Arg Ala
             35                  40                  45

Val Lys Ile Asp Arg Glu Cys Ala Leu Gln Ser Cys Ser Trp Gly Met
 50                  55                  60

Phe Gln Leu Met Gly Phe Asn Tyr Lys Leu Cys Gly Tyr Ala Thr Val
 65                  70                  75                  80

Gln Ala Phe Val Asn Ala Met Tyr Lys Ser Glu Asp Glu Gln Leu Asn
                 85                  90                  95

Ala Phe Val Gly Phe Ile Lys Ser Asn Leu Gln Leu
            100                 105
```

<210> SEQ ID NO 19
<211> LENGTH: 110
<212> TYPE: PRT
<213> ORGANISM: Artificial Sequence

```
<220> FEATURE:
<223> OTHER INFORMATION: peptidoglycan degrading enzyme

<400> SEQUENCE: 19

Ile Leu Tyr Glu Arg His Ile Met Ala Arg Leu Leu Lys Ala Lys Gly
1               5                   10                  15

Val Pro Ile Ala Gly Leu Pro Ser Asp Leu Val Asn Thr Thr Pro Gly
            20                  25                  30

Gly Tyr Gly Lys Phe Ser Glu Gln His Gly Lys Leu Asp Arg Ala Val
        35                  40                  45

Lys Ile Asp Arg Glu Cys Ala Leu Gln Ser Cys Ser Trp Gly Met Phe
50                  55                  60

Gln Leu Met Gly Phe Asn Tyr Lys Leu Cys Gly Tyr Ala Thr Val Gln
65                  70                  75                  80

Ala Phe Val Asn Ala Met Tyr Lys Ser Glu Asp Glu Gln Leu Asn Ala
                85                  90                  95

Phe Val Gly Phe Ile Lys Ser Asn Leu Gln Leu Asn Asp Ala
            100                 105                 110

<210> SEQ ID NO 20
<211> LENGTH: 111
<212> TYPE: PRT
<213> ORGANISM: Artificial Sequence
<220> FEATURE:
<223> OTHER INFORMATION: peptidoglycan degrading enzyme

<400> SEQUENCE: 20

Met Ile Leu Tyr Glu Arg His Ile Met Ala Arg Leu Leu Lys Ala Lys
1               5                   10                  15

Gly Val Pro Ile Ala Gly Leu Pro Ser Asp Leu Val Asn Thr Thr Pro
            20                  25                  30

Gly Gly Tyr Gly Lys Phe Ser Glu Gln His Gly Lys Leu Asp Arg Ala
        35                  40                  45

Val Lys Ile Asp Arg Glu Cys Ala Leu Gln Ser Cys Ser Trp Gly Met
50                  55                  60

Phe Gln Leu Met Gly Phe Asn Tyr Lys Leu Cys Gly Tyr Ala Thr Val
65                  70                  75                  80

Gln Ala Phe Val Asn Ala Met Tyr Lys Ser Glu Asp Glu Gln Leu Asn
                85                  90                  95

Ala Phe Val Gly Phe Ile Lys Ser Asn Leu Gln Leu Asn Asp Ala
            100                 105                 110

<210> SEQ ID NO 21
<211> LENGTH: 115
<212> TYPE: PRT
<213> ORGANISM: Artificial Sequence
<220> FEATURE:
<223> OTHER INFORMATION: peptidoglycan degrading enzyme

<400> SEQUENCE: 21

Ile Lys Ala Ile Ala Ser Val Glu Thr Lys Gly Ser Ala Trp Ile Thr
1               5                   10                  15

Pro Gly Val Pro Gln Ile Leu Tyr Glu Arg His Ile Met Ala Arg Leu
            20                  25                  30

Leu Lys Ala Lys Gly Val Pro Ile Ala Gly Leu Pro Ser Asp Leu Val
        35                  40                  45

Asn Thr Thr Pro Gly Gly Tyr Gly Lys Phe Ser Glu Gln His Gly Lys
50                  55                  60
```

```
Leu Asp Arg Ala Val Lys Ile Asp Arg Glu Cys Ala Leu Gln Ser Cys
 65                  70                  75                  80

Ser Trp Gly Met Phe Gln Leu Met Gly Phe Asn Tyr Lys Leu Cys Gly
                 85                  90                  95

Tyr Ala Thr Val Gln Ala Phe Val Asn Ala Met Tyr Lys Ser Glu Asp
            100                 105                 110

Glu Gln Leu
        115

<210> SEQ ID NO 22
<211> LENGTH: 116
<212> TYPE: PRT
<213> ORGANISM: Artificial Sequence
<220> FEATURE:
<223> OTHER INFORMATION: peptidoglycan degrading enzyme

<400> SEQUENCE: 22

Met Ile Lys Ala Ile Ala Ser Val Glu Thr Lys Gly Ser Ala Trp Ile
  1               5                  10                  15

Thr Pro Gly Val Pro Gln Ile Leu Tyr Glu Arg His Ile Met Ala Arg
                 20                  25                  30

Leu Leu Lys Ala Lys Gly Val Pro Ile Ala Gly Leu Pro Ser Asp Leu
             35                  40                  45

Val Asn Thr Thr Pro Gly Gly Tyr Gly Lys Phe Ser Glu Gln His Gly
 50                  55                  60

Lys Leu Asp Arg Ala Val Lys Ile Asp Arg Glu Cys Ala Leu Gln Ser
 65                  70                  75                  80

Cys Ser Trp Gly Met Phe Gln Leu Met Gly Phe Asn Tyr Lys Leu Cys
                 85                  90                  95

Gly Tyr Ala Thr Val Gln Ala Phe Val Asn Ala Met Tyr Lys Ser Glu
            100                 105                 110

Asp Glu Gln Leu
        115

<210> SEQ ID NO 23
<211> LENGTH: 125
<212> TYPE: PRT
<213> ORGANISM: Artificial Sequence
<220> FEATURE:
<223> OTHER INFORMATION: peptidoglycan degrading enzyme

<400> SEQUENCE: 23

Ile Lys Ala Ile Ala Ser Val Glu Thr Lys Gly Ser Ala Trp Ile Thr
  1               5                  10                  15

Pro Gly Val Pro Gln Ile Leu Tyr Glu Arg His Ile Met Ala Arg Leu
                 20                  25                  30

Leu Lys Ala Lys Gly Val Pro Ile Ala Gly Leu Pro Ser Asp Leu Val
             35                  40                  45

Asn Thr Thr Pro Gly Gly Tyr Gly Lys Phe Ser Glu Gln His Gly Lys
 50                  55                  60

Leu Asp Arg Ala Val Lys Ile Asp Arg Glu Cys Ala Leu Gln Ser Cys
 65                  70                  75                  80

Ser Trp Gly Met Phe Gln Leu Met Gly Phe Asn Tyr Lys Leu Cys Gly
                 85                  90                  95

Tyr Ala Thr Val Gln Ala Phe Val Asn Ala Met Tyr Lys Ser Glu Asp
            100                 105                 110

Glu Gln Leu Asn Ala Phe Val Gly Phe Ile Lys Ser Asn
        115                 120                 125
```

<210> SEQ ID NO 24
<211> LENGTH: 126
<212> TYPE: PRT
<213> ORGANISM: Artificial Sequence
<220> FEATURE:
<223> OTHER INFORMATION: peptidoglycan degrading enzyme

<400> SEQUENCE: 24

```
Met Ile Lys Ala Ile Ala Ser Val Glu Thr Lys Gly Ser Ala Trp Ile
1               5                   10                  15

Thr Pro Gly Val Pro Gln Ile Leu Tyr Glu Arg His Ile Met Ala Arg
            20                  25                  30

Leu Leu Lys Ala Lys Gly Val Pro Ile Ala Gly Leu Pro Ser Asp Leu
        35                  40                  45

Val Asn Thr Thr Pro Gly Gly Tyr Gly Lys Phe Ser Glu Gln His Gly
    50                  55                  60

Lys Leu Asp Arg Ala Val Lys Ile Asp Arg Glu Cys Ala Leu Gln Ser
65                  70                  75                  80

Cys Ser Trp Gly Met Phe Gln Leu Met Gly Phe Asn Tyr Lys Leu Cys
                85                  90                  95

Gly Tyr Ala Thr Val Gln Ala Phe Val Asn Ala Met Tyr Lys Ser Glu
            100                 105                 110

Asp Glu Gln Leu Asn Ala Phe Val Gly Phe Ile Lys Ser Asn
        115                 120                 125
```

<210> SEQ ID NO 25
<211> LENGTH: 128
<212> TYPE: PRT
<213> ORGANISM: Artificial Sequence
<220> FEATURE:
<223> OTHER INFORMATION: peptidoglycan degrading enzyme

<400> SEQUENCE: 25

```
Ile Lys Ala Ile Ala Ser Val Glu Thr Lys Gly Ser Ala Trp Ile Thr
1               5                   10                  15

Pro Gly Val Pro Gln Ile Leu Tyr Glu Arg His Ile Met Ala Arg Leu
            20                  25                  30

Leu Lys Ala Lys Gly Val Pro Ile Ala Gly Leu Pro Ser Asp Leu Val
        35                  40                  45

Asn Thr Thr Pro Gly Gly Tyr Gly Lys Phe Ser Glu Gln His Gly Lys
    50                  55                  60

Leu Asp Arg Ala Val Lys Ile Asp Arg Glu Cys Ala Leu Gln Ser Cys
65                  70                  75                  80

Ser Trp Gly Met Phe Gln Leu Met Gly Phe Asn Tyr Lys Leu Cys Gly
                85                  90                  95

Tyr Ala Thr Val Gln Ala Phe Val Asn Ala Met Tyr Lys Ser Glu Asp
            100                 105                 110

Glu Gln Leu Asn Ala Phe Val Gly Phe Ile Lys Ser Asn Leu Gln Leu
        115                 120                 125
```

<210> SEQ ID NO 26
<211> LENGTH: 129
<212> TYPE: PRT
<213> ORGANISM: Artificial Sequence
<220> FEATURE:
<223> OTHER INFORMATION: peptidoglycan degrading enzyme

<400> SEQUENCE: 26

Met Ile Lys Ala Ile Ala Ser Val Glu Thr Lys Gly Ser Ala Trp Ile
1               5                   10                  15

Thr Pro Gly Val Pro Gln Ile Leu Tyr Glu Arg His Ile Met Ala Arg
            20                  25                  30

Leu Leu Lys Ala Lys Gly Val Pro Ile Ala Gly Leu Pro Ser Asp Leu
        35                  40                  45

Val Asn Thr Thr Pro Gly Gly Tyr Gly Lys Phe Ser Glu Gln His Gly
    50                  55                  60

Lys Leu Asp Arg Ala Val Lys Ile Asp Arg Glu Cys Ala Leu Gln Ser
65                  70                  75                  80

Cys Ser Trp Gly Met Phe Gln Leu Met Gly Phe Asn Tyr Lys Leu Cys
                85                  90                  95

Gly Tyr Ala Thr Val Gln Ala Phe Val Asn Ala Met Tyr Lys Ser Glu
            100                 105                 110

Asp Glu Gln Leu Asn Ala Phe Val Gly Phe Ile Lys Ser Asn Leu Gln
            115                 120                 125

Leu

<210> SEQ ID NO 27
<211> LENGTH: 131
<212> TYPE: PRT
<213> ORGANISM: Artificial Sequence
<220> FEATURE:
<223> OTHER INFORMATION: peptidoglycan degrading enzyme

<400> SEQUENCE: 27

Ile Lys Ala Ile Ala Ser Val Glu Thr Lys Gly Ser Ala Trp Ile Thr
1               5                   10                  15

Pro Gly Val Pro Gln Ile Leu Tyr Glu Arg His Ile Met Ala Arg Leu
            20                  25                  30

Leu Lys Ala Lys Gly Val Pro Ile Ala Gly Leu Pro Ser Asp Leu Val
        35                  40                  45

Asn Thr Thr Pro Gly Gly Tyr Gly Lys Phe Ser Glu Gln His Gly Lys
    50                  55                  60

Leu Asp Arg Ala Val Lys Ile Asp Arg Glu Cys Ala Leu Gln Ser Cys
65                  70                  75                  80

Ser Trp Gly Met Phe Gln Leu Met Gly Phe Asn Tyr Lys Leu Cys Gly
                85                  90                  95

Tyr Ala Thr Val Gln Ala Phe Val Asn Ala Met Tyr Lys Ser Glu Asp
            100                 105                 110

Glu Gln Leu Asn Ala Phe Val Gly Phe Ile Lys Ser Asn Leu Gln Leu
            115                 120                 125

Asn Asp Ala
    130

<210> SEQ ID NO 28
<211> LENGTH: 132
<212> TYPE: PRT
<213> ORGANISM: Artificial Sequence
<220> FEATURE:
<223> OTHER INFORMATION: peptidoglycan degrading enzyme

<400> SEQUENCE: 28

Met Ile Lys Ala Ile Ala Ser Val Glu Thr Lys Gly Ser Ala Trp Ile
1               5                   10                  15

Thr Pro Gly Val Pro Gln Ile Leu Tyr Glu Arg His Ile Met Ala Arg
            20                  25                  30

```
Leu Leu Lys Ala Lys Gly Val Pro Ile Ala Gly Leu Pro Ser Asp Leu
            35                  40                  45

Val Asn Thr Thr Pro Gly Gly Tyr Gly Lys Phe Ser Glu Gln His Gly
 50                  55                  60

Lys Leu Asp Arg Ala Val Lys Ile Asp Arg Glu Cys Ala Leu Gln Ser
 65                  70                  75                  80

Cys Ser Trp Gly Met Phe Gln Leu Met Gly Phe Asn Tyr Lys Leu Cys
                 85                  90                  95

Gly Tyr Ala Thr Val Gln Ala Phe Val Asn Ala Met Tyr Lys Ser Glu
                100                 105                 110

Asp Glu Gln Leu Asn Ala Phe Val Gly Phe Ile Lys Ser Asn Leu Gln
                115                 120                 125

Leu Asn Asp Ala
        130
```

<210> SEQ ID NO 29
<211> LENGTH: 105
<212> TYPE: PRT
<213> ORGANISM: Artificial Sequence
<220> FEATURE:
<223> OTHER INFORMATION: peptidoglycan degrading enzyme

<400> SEQUENCE: 29

```
Ile Lys Ala Ile Ala Ser Val Glu Thr Lys Gly Ser Ala Trp Ile Thr
 1               5                  10                  15

Pro Gly Val Pro Gln Ile Leu Tyr Glu Arg His Ile Met Ala Arg Leu
                20                  25                  30

Leu Lys Ala Lys Gly Val Pro Ile Ala Gly Leu Pro Ser Asp Leu Val
            35                  40                  45

Asn Thr Thr Pro Gly Gly Tyr Gly Lys Phe Ser Glu Gln His Gly Lys
 50                  55                  60

Leu Asp Arg Ala Val Lys Ile Asp Arg Glu Cys Ala Leu Gln Ser Cys
 65                  70                  75                  80

Ser Trp Gly Met Phe Gln Leu Met Gly Phe Asn Tyr Lys Leu Cys Gly
                 85                  90                  95

Tyr Ala Thr Val Gln Ala Phe Val Asn
                100                 105
```

<210> SEQ ID NO 30
<211> LENGTH: 106
<212> TYPE: PRT
<213> ORGANISM: Artificial Sequence
<220> FEATURE:
<223> OTHER INFORMATION: peptidoglycan degrading enzyme

<400> SEQUENCE: 30

```
Met Ile Lys Ala Ile Ala Ser Val Glu Thr Lys Gly Ser Ala Trp Ile
 1               5                  10                  15

Thr Pro Gly Val Pro Gln Ile Leu Tyr Glu Arg His Ile Met Ala Arg
                20                  25                  30

Leu Leu Lys Ala Lys Gly Val Pro Ile Ala Gly Leu Pro Ser Asp Leu
            35                  40                  45

Val Asn Thr Thr Pro Gly Gly Tyr Gly Lys Phe Ser Glu Gln His Gly
 50                  55                  60

Lys Leu Asp Arg Ala Val Lys Ile Asp Arg Glu Cys Ala Leu Gln Ser
 65                  70                  75                  80

Cys Ser Trp Gly Met Phe Gln Leu Met Gly Phe Asn Tyr Lys Leu Cys
                 85                  90                  95
```

Gly Tyr Ala Thr Val Gln Ala Phe Val Asn
            100                 105

<210> SEQ ID NO 31
<211> LENGTH: 108
<212> TYPE: PRT
<213> ORGANISM: Artificial Sequence
<220> FEATURE:
<223> OTHER INFORMATION: peptidoglycan degrading enzyme

<400> SEQUENCE: 31

Val Ala Ala Ile Lys Ala Ile Ala Ser Val Glu Thr Lys Gly Ser Ala
1               5                   10                  15

Trp Ile Thr Pro Gly Val Pro Gln Ile Leu Tyr Glu Arg His Ile Met
            20                  25                  30

Ala Arg Leu Leu Lys Ala Lys Gly Val Pro Ile Ala Gly Leu Pro Ser
        35                  40                  45

Asp Leu Val Asn Thr Thr Pro Gly Gly Tyr Gly Lys Phe Ser Glu Gln
    50                  55                  60

His Gly Lys Leu Asp Arg Ala Val Lys Ile Asp Arg Glu Cys Ala Leu
65                  70                  75                  80

Gln Ser Cys Ser Trp Gly Met Phe Gln Leu Met Gly Phe Asn Tyr Lys
                85                  90                  95

Leu Cys Gly Tyr Ala Thr Val Gln Ala Phe Val Asn
            100                 105

<210> SEQ ID NO 32
<211> LENGTH: 109
<212> TYPE: PRT
<213> ORGANISM: Artificial Sequence
<220> FEATURE:
<223> OTHER INFORMATION: peptidoglycan degrading enzyme

<400> SEQUENCE: 32

Met Val Ala Ala Ile Lys Ala Ile Ala Ser Val Glu Thr Lys Gly Ser
1               5                   10                  15

Ala Trp Ile Thr Pro Gly Val Pro Gln Ile Leu Tyr Glu Arg His Ile
            20                  25                  30

Met Ala Arg Leu Leu Lys Ala Lys Gly Val Pro Ile Ala Gly Leu Pro
        35                  40                  45

Ser Asp Leu Val Asn Thr Thr Pro Gly Gly Tyr Gly Lys Phe Ser Glu
    50                  55                  60

Gln His Gly Lys Leu Asp Arg Ala Val Lys Ile Asp Arg Glu Cys Ala
65                  70                  75                  80

Leu Gln Ser Cys Ser Trp Gly Met Phe Gln Leu Met Gly Phe Asn Tyr
                85                  90                  95

Lys Leu Cys Gly Tyr Ala Thr Val Gln Ala Phe Val Asn
            100                 105

<210> SEQ ID NO 33
<211> LENGTH: 116
<212> TYPE: PRT
<213> ORGANISM: Artificial Sequence
<220> FEATURE:
<223> OTHER INFORMATION: peptidoglycan degrading enzyme

<400> SEQUENCE: 33

Ala Ala Ala Ser Leu Gly Cys Glu Val Ala Ala Ile Lys Ala Ile Ala
1               5                   10                  15

Ser Val Glu Thr Lys Gly Ser Ala Trp Ile Thr Pro Gly Val Pro Gln
            20                  25                  30

Ile Leu Tyr Glu Arg His Ile Met Ala Arg Leu Leu Lys Ala Lys Gly
        35                  40                  45

Val Pro Ile Ala Gly Leu Pro Ser Asp Leu Val Asn Thr Thr Pro Gly
    50                  55                  60

Gly Tyr Gly Lys Phe Ser Glu Gln His Gly Lys Leu Asp Arg Ala Val
65                  70                  75                  80

Lys Ile Asp Arg Glu Cys Ala Leu Gln Ser Cys Ser Trp Gly Met Phe
                85                  90                  95

Gln Leu Met Gly Phe Asn Tyr Lys Leu Cys Gly Tyr Ala Thr Val Gln
            100                 105                 110

Ala Phe Val Asn
        115

<210> SEQ ID NO 34
<211> LENGTH: 117
<212> TYPE: PRT
<213> ORGANISM: Artificial Sequence
<220> FEATURE:
<223> OTHER INFORMATION: peptidoglycan degrading enzyme

<400> SEQUENCE: 34

Met Ala Ala Ala Ser Leu Gly Cys Glu Val Ala Ala Ile Lys Ala Ile
1               5                   10                  15

Ala Ser Val Glu Thr Lys Gly Ser Ala Trp Ile Thr Pro Gly Val Pro
            20                  25                  30

Gln Ile Leu Tyr Glu Arg His Ile Met Ala Arg Leu Leu Lys Ala Lys
        35                  40                  45

Gly Val Pro Ile Ala Gly Leu Pro Ser Asp Leu Val Asn Thr Thr Pro
    50                  55                  60

Gly Gly Tyr Gly Lys Phe Ser Glu Gln His Gly Lys Leu Asp Arg Ala
65                  70                  75                  80

Val Lys Ile Asp Arg Glu Cys Ala Leu Gln Ser Cys Ser Trp Gly Met
                85                  90                  95

Phe Gln Leu Met Gly Phe Asn Tyr Lys Leu Cys Gly Tyr Ala Thr Val
            100                 105                 110

Gln Ala Phe Val Asn
        115

<210> SEQ ID NO 35
<211> LENGTH: 121
<212> TYPE: PRT
<213> ORGANISM: Artificial Sequence
<220> FEATURE:
<223> OTHER INFORMATION: peptidoglycan degrading enzyme

<400> SEQUENCE: 35

Lys Ser Phe Val Glu Ala Ala Ser Leu Gly Cys Glu Val Ala Ala
1               5                   10                  15

Ile Lys Ala Ile Ala Ser Val Glu Thr Lys Gly Ser Ala Trp Ile Thr
            20                  25                  30

Pro Gly Val Pro Gln Ile Leu Tyr Glu Arg His Ile Met Ala Arg Leu
        35                  40                  45

Leu Lys Ala Lys Gly Val Pro Ile Ala Gly Leu Pro Ser Asp Leu Val
    50                  55                  60

Asn Thr Thr Pro Gly Gly Tyr Gly Lys Phe Ser Glu Gln His Gly Lys
65                  70                  75                  80

Leu Asp Arg Ala Val Lys Ile Asp Arg Glu Cys Ala Leu Gln Ser Cys
                85                  90                  95

Ser Trp Gly Met Phe Gln Leu Met Gly Phe Asn Tyr Lys Leu Cys Gly
            100                 105                 110

Tyr Ala Thr Val Gln Ala Phe Val Asn
        115                 120

<210> SEQ ID NO 36
<211> LENGTH: 122
<212> TYPE: PRT
<213> ORGANISM: Artificial Sequence
<220> FEATURE:
<223> OTHER INFORMATION: peptidoglycan degrading enzyme

<400> SEQUENCE: 36

Met Lys Ser Phe Val Glu Ala Ala Ser Leu Gly Cys Glu Val Ala
1               5                   10                  15

Ala Ile Lys Ala Ile Ala Ser Val Glu Thr Lys Gly Ser Ala Trp Ile
            20                  25                  30

Thr Pro Gly Val Pro Gln Ile Leu Tyr Glu Arg His Ile Met Ala Arg
        35                  40                  45

Leu Leu Lys Ala Lys Gly Val Pro Ile Ala Gly Leu Pro Ser Asp Leu
    50                  55                  60

Val Asn Thr Thr Pro Gly Gly Tyr Gly Lys Phe Ser Glu Gln His Gly
65                  70                  75                  80

Lys Leu Asp Arg Ala Val Lys Ile Asp Arg Glu Cys Ala Leu Gln Ser
                85                  90                  95

Cys Ser Trp Gly Met Phe Gln Leu Met Gly Phe Asn Tyr Lys Leu Cys
            100                 105                 110

Gly Tyr Ala Thr Val Gln Ala Phe Val Asn
        115                 120

<210> SEQ ID NO 37
<211> LENGTH: 104
<212> TYPE: PRT
<213> ORGANISM: Artificial Sequence
<220> FEATURE:
<223> OTHER INFORMATION: peptidoglycan degrading enzyme

<400> SEQUENCE: 37

Ser Ala Trp Ile Thr Pro Gly Val Pro Gln Ile Leu Tyr Glu Arg His
1               5                   10                  15

Ile Met Ala Arg Leu Leu Lys Ala Lys Gly Val Pro Ile Ala Gly Leu
            20                  25                  30

Pro Ser Asp Leu Val Asn Thr Thr Pro Gly Gly Tyr Gly Lys Phe Ser
        35                  40                  45

Glu Gln His Gly Lys Leu Asp Arg Ala Val Lys Ile Asp Arg Glu Cys
    50                  55                  60

Ala Leu Gln Ser Cys Ser Trp Gly Met Phe Gln Leu Met Gly Phe Asn
65                  70                  75                  80

Tyr Lys Leu Cys Gly Tyr Ala Thr Val Gln Ala Phe Val Asn Ala Met
                85                  90                  95

Tyr Lys Ser Glu Asp Glu Gln Leu
            100

<210> SEQ ID NO 38
<211> LENGTH: 105
<212> TYPE: PRT

```
<213> ORGANISM: Artificial Sequence
<220> FEATURE:
<223> OTHER INFORMATION: peptidoglycan degrading enzyme

<400> SEQUENCE: 38

Met Ser Ala Trp Ile Thr Pro Gly Val Pro Gln Ile Leu Tyr Glu Arg
1               5                   10                  15

His Ile Met Ala Arg Leu Leu Lys Ala Lys Gly Val Pro Ile Ala Gly
            20                  25                  30

Leu Pro Ser Asp Leu Val Asn Thr Thr Pro Gly Gly Tyr Gly Lys Phe
        35                  40                  45

Ser Glu Gln His Gly Lys Leu Asp Arg Ala Val Lys Ile Asp Arg Glu
50                  55                  60

Cys Ala Leu Gln Ser Cys Ser Trp Gly Met Phe Gln Leu Met Gly Phe
65                  70                  75                  80

Asn Tyr Lys Leu Cys Gly Tyr Ala Thr Val Gln Ala Phe Val Asn Ala
                85                  90                  95

Met Tyr Lys Ser Glu Asp Glu Gln Leu
            100                 105

<210> SEQ ID NO 39
<211> LENGTH: 118
<212> TYPE: PRT
<213> ORGANISM: Artificial Sequence
<220> FEATURE:
<223> OTHER INFORMATION: peptidoglycan degrading enzyme

<400> SEQUENCE: 39

Val Ala Ala Ile Lys Ala Ile Ala Ser Val Glu Thr Lys Gly Ser Ala
1               5                   10                  15

Trp Ile Thr Pro Gly Val Pro Gln Ile Leu Tyr Glu Arg His Ile Met
            20                  25                  30

Ala Arg Leu Leu Lys Ala Lys Gly Val Pro Ile Ala Gly Leu Pro Ser
        35                  40                  45

Asp Leu Val Asn Thr Thr Pro Gly Gly Tyr Gly Lys Phe Ser Glu Gln
50                  55                  60

His Gly Lys Leu Asp Arg Ala Val Lys Ile Asp Arg Glu Cys Ala Leu
65                  70                  75                  80

Gln Ser Cys Ser Trp Gly Met Phe Gln Leu Met Gly Phe Asn Tyr Lys
                85                  90                  95

Leu Cys Gly Tyr Ala Thr Val Gln Ala Phe Val Asn Ala Met Tyr Lys
            100                 105                 110

Ser Glu Asp Glu Gln Leu
        115

<210> SEQ ID NO 40
<211> LENGTH: 119
<212> TYPE: PRT
<213> ORGANISM: Artificial Sequence
<220> FEATURE:
<223> OTHER INFORMATION: peptidoglycan degrading enzyme

<400> SEQUENCE: 40

Met Val Ala Ala Ile Lys Ala Ile Ala Ser Val Glu Thr Lys Gly Ser
1               5                   10                  15

Ala Trp Ile Thr Pro Gly Val Pro Gln Ile Leu Tyr Glu Arg His Ile
            20                  25                  30

Met Ala Arg Leu Leu Lys Ala Lys Gly Val Pro Ile Ala Gly Leu Pro
        35                  40                  45
```

Ser Asp Leu Val Asn Thr Thr Pro Gly Gly Tyr Gly Lys Phe Ser Glu
 50                  55                  60

Gln His Gly Lys Leu Asp Arg Ala Val Lys Ile Asp Arg Glu Cys Ala
 65                  70                  75                  80

Leu Gln Ser Cys Ser Trp Gly Met Phe Gln Leu Met Gly Phe Asn Tyr
                 85                  90                  95

Lys Leu Cys Gly Tyr Ala Thr Val Gln Ala Phe Val Asn Ala Met Tyr
            100                 105                 110

Lys Ser Glu Asp Glu Gln Leu
            115

<210> SEQ ID NO 41
<211> LENGTH: 126
<212> TYPE: PRT
<213> ORGANISM: Artificial Sequence
<220> FEATURE:
<223> OTHER INFORMATION: peptidoglycan degrading enzyme

<400> SEQUENCE: 41

Ala Ala Ala Ser Leu Gly Cys Glu Val Ala Ala Ile Lys Ala Ile Ala
 1               5                  10                  15

Ser Val Glu Thr Lys Gly Ser Ala Trp Ile Thr Pro Gly Val Pro Gln
             20                  25                  30

Ile Leu Tyr Glu Arg His Ile Met Ala Arg Leu Leu Lys Ala Lys Gly
         35                  40                  45

Val Pro Ile Ala Gly Leu Pro Ser Asp Leu Val Asn Thr Thr Pro Gly
     50                  55                  60

Gly Tyr Gly Lys Phe Ser Glu Gln His Gly Lys Leu Asp Arg Ala Val
 65                  70                  75                  80

Lys Ile Asp Arg Glu Cys Ala Leu Gln Ser Cys Ser Trp Gly Met Phe
                 85                  90                  95

Gln Leu Met Gly Phe Asn Tyr Lys Leu Cys Gly Tyr Ala Thr Val Gln
            100                 105                 110

Ala Phe Val Asn Ala Met Tyr Lys Ser Glu Asp Glu Gln Leu
            115                 120                 125

<210> SEQ ID NO 42
<211> LENGTH: 127
<212> TYPE: PRT
<213> ORGANISM: Artificial Sequence
<220> FEATURE:
<223> OTHER INFORMATION: peptidoglycan degrading enzyme

<400> SEQUENCE: 42

Met Ala Ala Ala Ser Leu Gly Cys Glu Val Ala Ala Ile Lys Ala Ile
 1               5                  10                  15

Ala Ser Val Glu Thr Lys Gly Ser Ala Trp Ile Thr Pro Gly Val Pro
             20                  25                  30

Gln Ile Leu Tyr Glu Arg His Ile Met Ala Arg Leu Leu Lys Ala Lys
         35                  40                  45

Gly Val Pro Ile Ala Gly Leu Pro Ser Asp Leu Val Asn Thr Thr Pro
     50                  55                  60

Gly Gly Tyr Gly Lys Phe Ser Glu Gln His Gly Lys Leu Asp Arg Ala
 65                  70                  75                  80

Val Lys Ile Asp Arg Glu Cys Ala Leu Gln Ser Cys Ser Trp Gly Met
                 85                  90                  95

Phe Gln Leu Met Gly Phe Asn Tyr Lys Leu Cys Gly Tyr Ala Thr Val

```
            100                 105                 110

Gln Ala Phe Val Asn Ala Met Tyr Lys Ser Glu Asp Glu Gln Leu
        115                 120                 125

<210> SEQ ID NO 43
<211> LENGTH: 131
<212> TYPE: PRT
<213> ORGANISM: Artificial Sequence
<220> FEATURE:
<223> OTHER INFORMATION: peptidoglycan degrading enzyme

<400> SEQUENCE: 43

Lys Ser Phe Val Glu Ala Ala Ser Leu Gly Cys Glu Val Ala Ala
1               5                   10                  15

Ile Lys Ala Ile Ala Ser Val Glu Thr Lys Gly Ser Ala Trp Ile Thr
            20                  25                  30

Pro Gly Val Pro Gln Ile Leu Tyr Glu Arg His Ile Met Ala Arg Leu
        35                  40                  45

Leu Lys Ala Lys Gly Val Pro Ile Ala Gly Leu Pro Ser Asp Leu Val
    50                  55                  60

Asn Thr Thr Pro Gly Gly Tyr Gly Lys Phe Ser Glu Gln His Gly Lys
65                  70                  75                  80

Leu Asp Arg Ala Val Lys Ile Asp Arg Glu Cys Ala Leu Gln Ser Cys
                85                  90                  95

Ser Trp Gly Met Phe Gln Leu Met Gly Phe Asn Tyr Lys Leu Cys Gly
            100                 105                 110

Tyr Ala Thr Val Gln Ala Phe Val Asn Ala Met Tyr Lys Ser Glu Asp
        115                 120                 125

Glu Gln Leu
    130

<210> SEQ ID NO 44
<211> LENGTH: 132
<212> TYPE: PRT
<213> ORGANISM: Artificial Sequence
<220> FEATURE:
<223> OTHER INFORMATION: peptidoglycan degrading enzyme

<400> SEQUENCE: 44

Met Lys Ser Phe Val Glu Ala Ala Ala Ser Leu Gly Cys Glu Val Ala
1               5                   10                  15

Ala Ile Lys Ala Ile Ala Ser Val Glu Thr Lys Gly Ser Ala Trp Ile
            20                  25                  30

Thr Pro Gly Val Pro Gln Ile Leu Tyr Glu Arg His Ile Met Ala Arg
        35                  40                  45

Leu Leu Lys Ala Lys Gly Val Pro Ile Ala Gly Leu Pro Ser Asp Leu
    50                  55                  60

Val Asn Thr Thr Pro Gly Gly Tyr Gly Lys Phe Ser Glu Gln His Gly
65                  70                  75                  80

Lys Leu Asp Arg Ala Val Lys Ile Asp Arg Glu Cys Ala Leu Gln Ser
                85                  90                  95

Cys Ser Trp Gly Met Phe Gln Leu Met Gly Phe Asn Tyr Lys Leu Cys
            100                 105                 110

Gly Tyr Ala Thr Val Gln Ala Phe Val Asn Ala Met Tyr Lys Ser Glu
        115                 120                 125

Asp Glu Gln Leu
    130
```

```
<210> SEQ ID NO 45
<211> LENGTH: 171
<212> TYPE: PRT
<213> ORGANISM: Artificial Sequence
<220> FEATURE:
<223> OTHER INFORMATION: peptidoglycan degrading enzyme

<400> SEQUENCE: 45

Cys Glu Val Ala Ala Ile Lys Ala Ile Ala Ser Val Glu Thr Lys Gly
1               5                   10                  15

Ser Ala Trp Ile Thr Pro Gly Val Pro Gln Ile Leu Tyr Glu Arg His
            20                  25                  30

Ile Met Ala Arg Leu Leu Lys Ala Lys Gly Val Pro Ile Ala Gly Leu
        35                  40                  45

Pro Ser Asp Leu Val Asn Thr Thr Pro Gly Gly Tyr Gly Lys Phe Ser
    50                  55                  60

Glu Gln His Gly Lys Leu Asp Arg Ala Val Lys Ile Asp Arg Glu Cys
65                  70                  75                  80

Ala Leu Gln Ser Cys Ser Trp Gly Met Phe Gln Leu Met Gly Phe Asn
                85                  90                  95

Tyr Lys Leu Cys Gly Tyr Ala Thr Val Gln Ala Phe Val Asn Ala Met
            100                 105                 110

Tyr Lys Ser Glu Asp Glu Gln Leu Asn Ala Phe Val Gly Phe Ile Lys
        115                 120                 125

Ser Asn Leu Gln Leu Asn Asp Ala Leu Lys Ser Lys Asp Trp Ala Thr
    130                 135                 140

Val Ala Arg Leu Tyr Asn Gly Ala Asp Tyr Lys Ile Asn Ser Tyr Asp
145                 150                 155                 160

Gln Lys Leu Ala Val Ala Tyr Glu Ser Asn Lys
                165                 170

<210> SEQ ID NO 46
<211> LENGTH: 172
<212> TYPE: PRT
<213> ORGANISM: Artificial Sequence
<220> FEATURE:
<223> OTHER INFORMATION: peptidoglycan degrading enzyme

<400> SEQUENCE: 46

Met Cys Glu Val Ala Ala Ile Lys Ala Ile Ala Ser Val Glu Thr Lys
1               5                   10                  15

Gly Ser Ala Trp Ile Thr Pro Gly Val Pro Gln Ile Leu Tyr Glu Arg
            20                  25                  30

His Ile Met Ala Arg Leu Leu Lys Ala Lys Gly Val Pro Ile Ala Gly
        35                  40                  45

Leu Pro Ser Asp Leu Val Asn Thr Thr Pro Gly Gly Tyr Gly Lys Phe
    50                  55                  60

Ser Glu Gln His Gly Lys Leu Asp Arg Ala Val Lys Ile Asp Arg Glu
65                  70                  75                  80

Cys Ala Leu Gln Ser Cys Ser Trp Gly Met Phe Gln Leu Met Gly Phe
                85                  90                  95

Asn Tyr Lys Leu Cys Gly Tyr Ala Thr Val Gln Ala Phe Val Asn Ala
            100                 105                 110

Met Tyr Lys Ser Glu Asp Glu Gln Leu Asn Ala Phe Val Gly Phe Ile
        115                 120                 125

Lys Ser Asn Leu Gln Leu Asn Asp Ala Leu Lys Ser Lys Asp Trp Ala
    130                 135                 140
```

```
Thr Val Ala Arg Leu Tyr Asn Gly Ala Asp Tyr Lys Ile Asn Ser Tyr
145                 150                 155                 160

Asp Gln Lys Leu Ala Val Ala Tyr Glu Ser Asn Lys
                165                 170
```

<210> SEQ ID NO 47
<211> LENGTH: 184
<212> TYPE: PRT
<213> ORGANISM: Artificial Sequence
<220> FEATURE:
<223> OTHER INFORMATION: peptidoglycan degrading enzyme

<400> SEQUENCE: 47

```
Glu Lys Ser Phe Val Glu Ala Ala Ser Leu Gly Cys Glu Val Ala
1                   5                  10                  15

Ala Ile Lys Ala Ile Ala Ser Val Glu Thr Lys Gly Ser Ala Trp Ile
                20                  25                  30

Thr Pro Gly Val Pro Gln Ile Leu Tyr Glu Arg His Ile Met Ala Arg
            35                  40                  45

Leu Leu Lys Ala Lys Gly Val Pro Ile Ala Gly Leu Pro Ser Asp Leu
        50                  55                  60

Val Asn Thr Thr Pro Gly Gly Tyr Gly Lys Phe Ser Glu Gln His Gly
65                  70                  75                  80

Lys Leu Asp Arg Ala Val Lys Ile Asp Arg Glu Cys Ala Leu Gln Ser
                85                  90                  95

Cys Ser Trp Gly Met Phe Gln Leu Met Gly Phe Asn Tyr Lys Leu Cys
            100                 105                 110

Gly Tyr Ala Thr Val Gln Ala Phe Val Asn Ala Met Tyr Lys Ser Glu
        115                 120                 125

Asp Glu Gln Leu Asn Ala Phe Val Gly Phe Ile Lys Ser Asn Leu Gln
    130                 135                 140

Leu Asn Asp Ala Leu Lys Ser Lys Asp Trp Ala Thr Val Ala Arg Leu
145                 150                 155                 160

Tyr Asn Gly Ala Asp Tyr Lys Ile Asn Ser Tyr Asp Gln Lys Leu Ala
                165                 170                 175

Val Ala Tyr Glu Ser Asn Lys Arg
            180
```

<210> SEQ ID NO 48
<211> LENGTH: 185
<212> TYPE: PRT
<213> ORGANISM: Artificial Sequence
<220> FEATURE:
<223> OTHER INFORMATION: peptidoglycan degrading enzyme

<400> SEQUENCE: 48

```
Met Glu Lys Ser Phe Val Glu Ala Ala Ser Leu Gly Cys Glu Val
1                   5                  10                  15

Ala Ala Ile Lys Ala Ile Ala Ser Val Glu Thr Lys Gly Ser Ala Trp
                20                  25                  30

Ile Thr Pro Gly Val Pro Gln Ile Leu Tyr Glu Arg His Ile Met Ala
            35                  40                  45

Arg Leu Leu Lys Ala Lys Gly Val Pro Ile Ala Gly Leu Pro Ser Asp
        50                  55                  60

Leu Val Asn Thr Thr Pro Gly Gly Tyr Gly Lys Phe Ser Glu Gln His
65                  70                  75                  80

Gly Lys Leu Asp Arg Ala Val Lys Ile Asp Arg Glu Cys Ala Leu Gln
```

```
                    85                  90                  95
Ser Cys Ser Trp Gly Met Phe Gln Leu Met Gly Phe Asn Tyr Lys Leu
                100                 105                 110

Cys Gly Tyr Ala Thr Val Gln Ala Phe Val Asn Ala Met Tyr Lys Ser
            115                 120                 125

Glu Asp Glu Gln Leu Asn Ala Phe Val Gly Phe Ile Lys Ser Asn Leu
        130                 135                 140

Gln Leu Asn Asp Ala Leu Lys Ser Lys Asp Trp Ala Thr Val Ala Arg
145                 150                 155                 160

Leu Tyr Asn Gly Ala Asp Tyr Lys Ile Asn Ser Tyr Asp Gln Lys Leu
                165                 170                 175

Ala Val Ala Tyr Glu Ser Asn Lys Arg
                180                 185

<210> SEQ ID NO 49
<211> LENGTH: 114
<212> TYPE: PRT
<213> ORGANISM: Artificial Sequence
<220> FEATURE:
<223> OTHER INFORMATION: peptidoglycan degrading enzyme

<400> SEQUENCE: 49

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
                20                  25                  30

Trp Ile Thr Pro Gly Val Pro Gln Ile Leu Tyr Glu Arg His Ile Met
            35                  40                  45

Ala Arg Leu Leu Lys Ala Lys Gly Val Pro Ile Ala Gly Leu Pro Ser
        50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
                100                 105                 110

Leu Cys

<210> SEQ ID NO 50
<211> LENGTH: 115
<212> TYPE: PRT
<213> ORGANISM: Artificial Sequence
<220> FEATURE:
<223> OTHER INFORMATION: peptidoglycan degrading enzyme

<400> SEQUENCE: 50

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
                20                  25                  30

Ala Trp Ile Thr Pro Gly Val Pro Gln Ile Leu Tyr Glu Arg His Ile
            35                  40                  45

Met Ala Arg Leu Leu Lys Ala Lys Gly Val Pro Ile Ala Gly Leu Pro
        50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
```

85                  90                  95

Leu Gln Ser Cys Ser Trp Gly Met Phe Gln Leu Met Gly Phe Asn Tyr
                 100                 105                 110

Lys Leu Cys
        115

<210> SEQ ID NO 51
<211> LENGTH: 124
<212> TYPE: PRT
<213> ORGANISM: Artificial Sequence
<220> FEATURE:
<223> OTHER INFORMATION: peptidoglycan degrading enzyme

<400> SEQUENCE: 51

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
                20                  25                  30

Trp Ile Thr Pro Gly Val Pro Gln Ile Leu Tyr Glu Arg His Ile Met
            35                  40                  45

Ala Arg Leu Leu Lys Ala Lys Gly Val Pro Ile Ala Gly Leu Pro Ser
50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
                100                 105                 110

Leu Cys Gly Tyr Ala Thr Val Gln Ala Phe Val Asn
            115                 120

<210> SEQ ID NO 52
<211> LENGTH: 125
<212> TYPE: PRT
<213> ORGANISM: Artificial Sequence
<220> FEATURE:
<223> OTHER INFORMATION: peptidoglycan degrading enzyme

<400> SEQUENCE: 52

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
                20                  25                  30

Ala Trp Ile Thr Pro Gly Val Pro Gln Ile Leu Tyr Glu Arg His Ile
            35                  40                  45

Met Ala Arg Leu Leu Lys Ala Lys Gly Val Pro Ile Ala Gly Leu Pro
50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
                100                 105                 110

Lys Leu Cys Gly Tyr Ala Thr Val Gln Ala Phe Val Asn
            115                 120                 125

<210> SEQ ID NO 53
<211> LENGTH: 134

```
<212> TYPE: PRT
<213> ORGANISM: Artificial Sequence
<220> FEATURE:
<223> OTHER INFORMATION: peptidoglycan degrading enzyme

<400> SEQUENCE: 53

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
            20                  25                  30

Trp Ile Thr Pro Gly Val Pro Gln Ile Leu Tyr Glu Arg His Ile Met
        35                  40                  45

Ala Arg Leu Leu Lys Ala Lys Gly Val Pro Ile Ala Gly Leu Pro Ser
    50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
            100                 105                 110

Leu Cys Gly Tyr Ala Thr Val Gln Ala Phe Val Asn Ala Met Tyr Lys
        115                 120                 125

Ser Glu Asp Glu Gln Leu
    130

<210> SEQ ID NO 54
<211> LENGTH: 135
<212> TYPE: PRT
<213> ORGANISM: Artificial Sequence
<220> FEATURE:
<223> OTHER INFORMATION: peptidoglycan degrading enzyme

<400> SEQUENCE: 54

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
            20                  25                  30

Ala Trp Ile Thr Pro Gly Val Pro Gln Ile Leu Tyr Glu Arg His Ile
        35                  40                  45

Met Ala Arg Leu Leu Lys Ala Lys Gly Val Pro Ile Ala Gly Leu Pro
    50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
        115                 120                 125

Lys Ser Glu Asp Glu Gln Leu
    130                 135

<210> SEQ ID NO 55
<211> LENGTH: 144
<212> TYPE: PRT
<213> ORGANISM: Artificial Sequence
<220> FEATURE:
<223> OTHER INFORMATION: peptidoglycan degrading enzyme
```

<400> SEQUENCE: 55

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
            20                  25                  30

Trp Ile Thr Pro Gly Val Pro Gln Ile Leu Tyr Glu Arg His Ile Met
        35                  40                  45

Ala Arg Leu Leu Lys Ala Lys Gly Val Pro Ile Ala Gly Leu Pro Ser
50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
            100                 105                 110

Leu Cys Gly Tyr Ala Thr Val Gln Ala Phe Val Asn Ala Met Tyr Lys
        115                 120                 125

Ser Glu Asp Glu Gln Leu Asn Ala Phe Val Gly Phe Ile Lys Ser Asn
    130                 135                 140

<210> SEQ ID NO 56
<211> LENGTH: 145
<212> TYPE: PRT
<213> ORGANISM: Artificial Sequence
<220> FEATURE:
<223> OTHER INFORMATION: peptidoglycan degrading enzyme

<400> SEQUENCE: 56

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
            20                  25                  30

Ala Trp Ile Thr Pro Gly Val Pro Gln Ile Leu Tyr Glu Arg His Ile
        35                  40                  45

Met Ala Arg Leu Leu Lys Ala Lys Gly Val Pro Ile Ala Gly Leu Pro
50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
        115                 120                 125

Lys Ser Glu Asp Glu Gln Leu Asn Ala Phe Val Gly Phe Ile Lys Ser
    130                 135                 140

Asn
145

<210> SEQ ID NO 57
<211> LENGTH: 147
<212> TYPE: PRT
<213> ORGANISM: Artificial Sequence
<220> FEATURE:
<223> OTHER INFORMATION: peptidoglycan degrading enzyme

<400> SEQUENCE: 57

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
            20                  25                  30

Trp Ile Thr Pro Gly Val Pro Gln Ile Leu Tyr Glu Arg His Ile Met
            35                  40                  45

Ala Arg Leu Leu Lys Ala Lys Gly Val Pro Ile Ala Gly Leu Pro Ser
        50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
            100                 105                 110

Leu Cys Gly Tyr Ala Thr Val Gln Ala Phe Val Asn Ala Met Tyr Lys
            115                 120                 125

Ser Glu Asp Glu Gln Leu Asn Ala Phe Val Gly Phe Ile Lys Ser Asn
            130                 135                 140

Leu Gln Leu
145

<210> SEQ ID NO 58
<211> LENGTH: 148
<212> TYPE: PRT
<213> ORGANISM: Artificial Sequence
<220> FEATURE:
<223> OTHER INFORMATION: peptidoglycan degrading enzyme

<400> SEQUENCE: 58

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
            20                  25                  30

Ala Trp Ile Thr Pro Gly Val Pro Gln Ile Leu Tyr Glu Arg His Ile
        35                  40                  45

Met Ala Arg Leu Leu Lys Ala Lys Gly Val Pro Ile Ala Gly Leu Pro
    50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
            115                 120                 125

Lys Ser Glu Asp Glu Gln Leu Asn Ala Phe Val Gly Phe Ile Lys Ser
            130                 135                 140

Asn Leu Gln Leu
145

<210> SEQ ID NO 59
<211> LENGTH: 150
<212> TYPE: PRT
<213> ORGANISM: Artificial Sequence
<220> FEATURE:
<223> OTHER INFORMATION: peptidoglycan degrading enzyme

<400> SEQUENCE: 59

```
Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
            20                  25                  30

Trp Ile Thr Pro Gly Val Pro Gln Ile Leu Tyr Glu Arg His Ile Met
            35                  40                  45

Ala Arg Leu Leu Lys Ala Lys Gly Val Pro Ile Ala Gly Leu Pro Ser
    50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
                100                 105                 110

Leu Cys Gly Tyr Ala Thr Val Gln Ala Phe Val Asn Ala Met Tyr Lys
            115                 120                 125

Ser Glu Asp Glu Gln Leu Asn Ala Phe Val Gly Phe Ile Lys Ser Asn
130                 135                 140

Leu Gln Leu Asn Asp Ala
145                 150

<210> SEQ ID NO 60
<211> LENGTH: 151
<212> TYPE: PRT
<213> ORGANISM: Artificial Sequence
<220> FEATURE:
<223> OTHER INFORMATION: peptidoglycan degrading enzyme

<400> SEQUENCE: 60

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
                20                  25                  30

Ala Trp Ile Thr Pro Gly Val Pro Gln Ile Leu Tyr Glu Arg His Ile
            35                  40                  45

Met Ala Arg Leu Leu Lys Ala Lys Gly Val Pro Ile Ala Gly Leu Pro
    50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
        115                 120                 125

Lys Ser Glu Asp Glu Gln Leu Asn Ala Phe Val Gly Phe Ile Lys Ser
130                 135                 140

Asn Leu Gln Leu Asn Asp Ala
145                 150

<210> SEQ ID NO 61
<211> LENGTH: 160
<212> TYPE: PRT
<213> ORGANISM: Artificial Sequence
<220> FEATURE:
<223> OTHER INFORMATION: peptidoglycan degrading enzyme
```

```
<400> SEQUENCE: 61

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
            20                  25                  30

Trp Ile Thr Pro Gly Val Pro Gln Ile Leu Tyr Glu Arg His Ile Met
            35                  40                  45

Ala Arg Leu Leu Lys Ala Lys Gly Val Pro Ile Ala Gly Leu Pro Ser
        50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
            100                 105                 110

Leu Cys Gly Tyr Ala Thr Val Gln Ala Phe Val Asn Ala Met Tyr Lys
            115                 120                 125

Ser Glu Asp Glu Gln Leu Asn Ala Phe Val Gly Phe Ile Lys Ser Asn
        130                 135                 140

Leu Gln Leu Asn Asp Ala Leu Lys Ser Lys Asp Trp Ala Thr Val Ala
145                 150                 155                 160

<210> SEQ ID NO 62
<211> LENGTH: 161
<212> TYPE: PRT
<213> ORGANISM: Artificial Sequence
<220> FEATURE:
<223> OTHER INFORMATION: peptidoglycan degrading enzyme

<400> SEQUENCE: 62

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
            20                  25                  30

Ala Trp Ile Thr Pro Gly Val Pro Gln Ile Leu Tyr Glu Arg His Ile
            35                  40                  45

Met Ala Arg Leu Leu Lys Ala Lys Gly Val Pro Ile Ala Gly Leu Pro
        50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
            115                 120                 125

Lys Ser Glu Asp Glu Gln Leu Asn Ala Phe Val Gly Phe Ile Lys Ser
        130                 135                 140

Asn Leu Gln Leu Asn Asp Ala Leu Lys Ser Lys Asp Trp Ala Thr Val
145                 150                 155                 160

Ala

<210> SEQ ID NO 63
<211> LENGTH: 165
<212> TYPE: PRT
<213> ORGANISM: Artificial Sequence
```

```
<220> FEATURE:
<223> OTHER INFORMATION: peptidoglycan degrading enzyme

<400> SEQUENCE: 63

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
            20                  25                  30

Trp Ile Thr Pro Gly Val Pro Gln Ile Leu Tyr Glu Arg His Ile Met
            35                  40                  45

Ala Arg Leu Leu Lys Ala Lys Gly Val Pro Ile Ala Gly Leu Pro Ser
        50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
            100                 105                 110

Leu Cys Gly Tyr Ala Thr Val Gln Ala Phe Val Asn Ala Met Tyr Lys
        115                 120                 125

Ser Glu Asp Glu Gln Leu Asn Ala Phe Val Gly Phe Ile Lys Ser Asn
    130                 135                 140

Leu Gln Leu Asn Asp Ala Leu Lys Ser Lys Asp Trp Ala Thr Val Ala
145                 150                 155                 160

Arg Leu Tyr Asn Gly
                165

<210> SEQ ID NO 64
<211> LENGTH: 166
<212> TYPE: PRT
<213> ORGANISM: Artificial Sequence
<220> FEATURE:
<223> OTHER INFORMATION: peptidoglycan degrading enzyme

<400> SEQUENCE: 64

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
            20                  25                  30

Ala Trp Ile Thr Pro Gly Val Pro Gln Ile Leu Tyr Glu Arg His Ile
            35                  40                  45

Met Ala Arg Leu Leu Lys Ala Lys Gly Val Pro Ile Ala Gly Leu Pro
        50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
        115                 120                 125

Lys Ser Glu Asp Glu Gln Leu Asn Ala Phe Val Gly Phe Ile Lys Ser
    130                 135                 140

Asn Leu Gln Leu Asn Asp Ala Leu Lys Ser Lys Asp Trp Ala Thr Val
145                 150                 155                 160

Ala Arg Leu Tyr Asn Gly
```

<210> SEQ ID NO 65
<211> LENGTH: 176
<212> TYPE: PRT
<213> ORGANISM: Artificial Sequence
<220> FEATURE:
<223> OTHER INFORMATION: peptidoglycan degrading enzyme

<400> SEQUENCE: 65

```
Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
                20                  25                  30

Trp Ile Thr Pro Gly Val Pro Gln Ile Leu Tyr Glu Arg His Ile Met
            35                  40                  45

Ala Arg Leu Leu Lys Ala Lys Gly Val Pro Ile Ala Gly Leu Pro Ser
        50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
            100                 105                 110

Leu Cys Gly Tyr Ala Thr Val Gln Ala Phe Val Asn Ala Met Tyr Lys
        115                 120                 125

Ser Glu Asp Glu Gln Leu Asn Ala Phe Val Gly Phe Ile Lys Ser Asn
    130                 135                 140

Leu Gln Leu Asn Asp Ala Leu Lys Ser Lys Asp Trp Ala Thr Val Ala
145                 150                 155                 160

Arg Leu Tyr Asn Gly Ala Asp Tyr Lys Ile Asn Ser Tyr Asp Gln Lys
                165                 170                 175
```

<210> SEQ ID NO 66
<211> LENGTH: 177
<212> TYPE: PRT
<213> ORGANISM: Artificial Sequence
<220> FEATURE:
<223> OTHER INFORMATION: peptidoglycan degrading enzyme

<400> SEQUENCE: 66

```
Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
                20                  25                  30

Ala Trp Ile Thr Pro Gly Val Pro Gln Ile Leu Tyr Glu Arg His Ile
            35                  40                  45

Met Ala Arg Leu Leu Lys Ala Lys Gly Val Pro Ile Ala Gly Leu Pro
        50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
        115                 120                 125
```

Lys Ser Glu Asp Glu Gln Leu Asn Ala Phe Val Gly Phe Ile Lys Ser
           130                 135                 140

Asn Leu Gln Leu Asn Asp Ala Leu Lys Ser Lys Asp Trp Ala Thr Val
145                 150                 155                 160

Ala Arg Leu Tyr Asn Gly Ala Asp Tyr Lys Ile Asn Ser Tyr Asp Gln
                165                 170                 175

Lys

<210> SEQ ID NO 67
<211> LENGTH: 181
<212> TYPE: PRT
<213> ORGANISM: Artificial Sequence
<220> FEATURE:
<223> OTHER INFORMATION: peptidoglycan degrading enzyme

<400> SEQUENCE: 67

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
                20                  25                  30

Trp Ile Thr Pro Gly Val Pro Gln Ile Leu Tyr Glu Arg His Ile Met
            35                  40                  45

Ala Arg Leu Leu Lys Ala Lys Gly Val Pro Ile Ala Gly Leu Pro Ser
        50                  55                  60

Asp Leu Val Asn Thr Thr Pro Gly Gly Tyr Gly Lys Phe Ser Glu Gln
65                  70                  75                  80

His Gly Lys Leu Asp Arg Ala Val Lys Ile Asp Arg Glu Cys Ala Leu
                85                  90                  95

Gln Ser Cys Ser Trp Gly Met Phe Gln Leu Met Gly Phe Asn Tyr Lys
            100                 105                 110

Leu Cys Gly Tyr Ala Thr Val Gln Ala Phe Val Asn Ala Met Tyr Lys
        115                 120                 125

Ser Glu Asp Glu Gln Leu Asn Ala Phe Val Gly Phe Ile Lys Ser Asn
    130                 135                 140

Leu Gln Leu Asn Asp Ala Leu Lys Ser Lys Asp Trp Ala Thr Val Ala
145                 150                 155                 160

Arg Leu Tyr Asn Gly Ala Asp Tyr Lys Ile Asn Ser Tyr Asp Gln Lys
                165                 170                 175

Leu Ala Val Ala Tyr
            180

<210> SEQ ID NO 68
<211> LENGTH: 182
<212> TYPE: PRT
<213> ORGANISM: Artificial Sequence
<220> FEATURE:
<223> OTHER INFORMATION: peptidoglycan degrading enzyme

<400> SEQUENCE: 68

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
                20                  25                  30

Ala Trp Ile Thr Pro Gly Val Pro Gln Ile Leu Tyr Glu Arg His Ile
            35                  40                  45

Met Ala Arg Leu Leu Lys Ala Lys Gly Val Pro Ile Ala Gly Leu Pro
        50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
        115                 120                 125

Lys Ser Glu Asp Glu Gln Leu Asn Ala Phe Val Gly Phe Ile Lys Ser
    130                 135                 140

Asn Leu Gln Leu Asn Asp Ala Leu Lys Ser Lys Asp Trp Ala Thr Val
145                 150                 155                 160

Ala Arg Leu Tyr Asn Gly Ala Asp Tyr Lys Ile Asn Ser Tyr Asp Gln
                165                 170                 175

Lys Leu Ala Val Ala Tyr
            180

<210> SEQ ID NO 69
<211> LENGTH: 162
<212> TYPE: PRT
<213> ORGANISM: Artificial Sequence
<220> FEATURE:
<223> OTHER INFORMATION: peptidoglycan degrading enzyme

<400> SEQUENCE: 69

Lys Ser Phe Val Glu Ala Ala Ser Leu Gly Cys Glu Val Ala Ala
1               5                   10                  15

Ile Lys Ala Ile Ala Ser Val Glu Thr Lys Gly Ser Ala Trp Ile Thr
                20                  25                  30

Pro Gly Val Pro Gln Ile Leu Tyr Glu Arg His Ile Met Ala Arg Leu
            35                  40                  45

Leu Lys Ala Lys Gly Val Pro Ile Ala Gly Leu Pro Ser Asp Leu Val
        50                  55                  60

Asn Thr Thr Pro Gly Gly Tyr Gly Lys Phe Ser Glu Gln His Gly Lys
65                  70                  75                  80

Leu Asp Arg Ala Val Lys Ile Asp Arg Glu Cys Ala Leu Gln Ser Cys
                85                  90                  95

Ser Trp Gly Met Phe Gln Leu Met Gly Phe Asn Tyr Lys Leu Cys Gly
            100                 105                 110

Tyr Ala Thr Val Gln Ala Phe Val Asn Ala Met Tyr Lys Ser Glu Asp
        115                 120                 125

Glu Gln Leu Asn Ala Phe Val Gly Phe Ile Lys Ser Asn Leu Gln Leu
    130                 135                 140

Asn Asp Ala Leu Lys Ser Lys Asp Trp Ala Thr Val Ala Arg Leu Tyr
145                 150                 155                 160

Asn Gly

<210> SEQ ID NO 70
<211> LENGTH: 163
<212> TYPE: PRT
<213> ORGANISM: Artificial Sequence
<220> FEATURE:
<223> OTHER INFORMATION: peptidoglycan degrading enzyme

<400> SEQUENCE: 70

Met Lys Ser Phe Val Glu Ala Ala Ser Leu Gly Cys Glu Val Ala
1               5                   10                  15

```
Ala Ile Lys Ala Ile Ala Ser Val Glu Thr Lys Gly Ser Ala Trp Ile
             20                  25                  30

Thr Pro Gly Val Pro Gln Ile Leu Tyr Glu Arg His Ile Met Ala Arg
         35                  40                  45

Leu Leu Lys Ala Lys Gly Val Pro Ile Ala Gly Leu Pro Ser Asp Leu
 50                  55                  60

Val Asn Thr Thr Pro Gly Gly Tyr Gly Lys Phe Ser Glu Gln His Gly
 65                  70                  75                  80

Lys Leu Asp Arg Ala Val Lys Ile Asp Arg Glu Cys Ala Leu Gln Ser
                 85                  90                  95

Cys Ser Trp Gly Met Phe Gln Leu Met Gly Phe Asn Tyr Lys Leu Cys
                100                 105                 110

Gly Tyr Ala Thr Val Gln Ala Phe Val Asn Ala Met Tyr Lys Ser Glu
                115                 120                 125

Asp Glu Gln Leu Asn Ala Phe Val Gly Phe Ile Lys Ser Asn Leu Gln
            130                 135                 140

Leu Asn Asp Ala Leu Lys Ser Lys Asp Trp Ala Thr Val Ala Arg Leu
145                 150                 155                 160

Tyr Asn Gly

<210> SEQ ID NO 71
<211> LENGTH: 173
<212> TYPE: PRT
<213> ORGANISM: Artificial Sequence
<220> FEATURE:
<223> OTHER INFORMATION: peptidoglycan degrading enzyme

<400> SEQUENCE: 71

Lys Ser Phe Val Glu Ala Ala Ser Leu Gly Cys Glu Val Ala Ala
  1               5                  10                  15

Ile Lys Ala Ile Ala Ser Val Glu Thr Lys Gly Ser Ala Trp Ile Thr
             20                  25                  30

Pro Gly Val Pro Gln Ile Leu Tyr Glu Arg His Ile Met Ala Arg Leu
         35                  40                  45

Leu Lys Ala Lys Gly Val Pro Ile Ala Gly Leu Pro Ser Asp Leu Val
 50                  55                  60

Asn Thr Thr Pro Gly Gly Tyr Gly Lys Phe Ser Glu Gln His Gly Lys
 65                  70                  75                  80

Leu Asp Arg Ala Val Lys Ile Asp Arg Glu Cys Ala Leu Gln Ser Cys
                 85                  90                  95

Ser Trp Gly Met Phe Gln Leu Met Gly Phe Asn Tyr Lys Leu Cys Gly
                100                 105                 110

Tyr Ala Thr Val Gln Ala Phe Val Asn Ala Met Tyr Lys Ser Glu Asp
            115                 120                 125

Glu Gln Leu Asn Ala Phe Val Gly Phe Ile Lys Ser Asn Leu Gln Leu
        130                 135                 140

Asn Asp Ala Leu Lys Ser Lys Asp Trp Ala Thr Val Ala Arg Leu Tyr
145                 150                 155                 160

Asn Gly Ala Asp Tyr Lys Ile Asn Ser Tyr Asp Gln Lys
                165                 170

<210> SEQ ID NO 72
<211> LENGTH: 174
<212> TYPE: PRT
<213> ORGANISM: Artificial Sequence
<220> FEATURE:
<223> OTHER INFORMATION: peptidoglycan degrading enzyme
```

<400> SEQUENCE: 72

Met Lys Ser Phe Val Glu Ala Ala Ser Leu Gly Cys Glu Val Ala
1               5                   10                  15

Ala Ile Lys Ala Ile Ala Ser Val Glu Thr Lys Gly Ser Ala Trp Ile
            20                  25                  30

Thr Pro Gly Val Pro Gln Ile Leu Tyr Glu Arg His Ile Met Ala Arg
            35                  40                  45

Leu Leu Lys Ala Lys Gly Val Pro Ile Ala Gly Leu Pro Ser Asp Leu
50                  55                  60

Val Asn Thr Thr Pro Gly Gly Tyr Gly Lys Phe Ser Glu Gln His Gly
65                  70                  75                  80

Lys Leu Asp Arg Ala Val Lys Ile Asp Arg Glu Cys Ala Leu Gln Ser
                85                  90                  95

Cys Ser Trp Gly Met Phe Gln Leu Met Gly Phe Asn Tyr Lys Leu Cys
            100                 105                 110

Gly Tyr Ala Thr Val Gln Ala Phe Val Asn Ala Met Tyr Lys Ser Glu
            115                 120                 125

Asp Glu Gln Leu Asn Ala Phe Val Gly Phe Ile Lys Ser Asn Leu Gln
130                 135                 140

Leu Asn Asp Ala Leu Lys Ser Lys Asp Trp Ala Thr Val Ala Arg Leu
145                 150                 155                 160

Tyr Asn Gly Ala Asp Tyr Lys Ile Asn Ser Tyr Asp Gln Lys
                165                 170

<210> SEQ ID NO 73
<211> LENGTH: 142
<212> TYPE: PRT
<213> ORGANISM: Artificial Sequence
<220> FEATURE:
<223> OTHER INFORMATION: peptidoglycan degrading enzyme

<400> SEQUENCE: 73

Ala Ala Ala Ser Leu Gly Cys Glu Val Ala Ala Ile Lys Ala Ile Ala
1               5                   10                  15

Ser Val Glu Thr Lys Gly Ser Ala Trp Ile Thr Pro Gly Val Pro Gln
            20                  25                  30

Ile Leu Tyr Glu Arg His Ile Met Ala Arg Leu Leu Lys Ala Lys Gly
            35                  40                  45

Val Pro Ile Ala Gly Leu Pro Ser Asp Leu Val Asn Thr Thr Pro Gly
50                  55                  60

Gly Tyr Gly Lys Phe Ser Glu Gln His Gly Lys Leu Asp Arg Ala Val
65                  70                  75                  80

Lys Ile Asp Arg Glu Cys Ala Leu Gln Ser Cys Ser Trp Gly Met Phe
                85                  90                  95

Gln Leu Met Gly Phe Asn Tyr Lys Leu Cys Gly Tyr Ala Thr Val Gln
            100                 105                 110

Ala Phe Val Asn Ala Met Tyr Lys Ser Glu Asp Glu Gln Leu Asn Ala
            115                 120                 125

Phe Val Gly Phe Ile Lys Ser Asn Leu Gln Leu Asn Asp Ala
130                 135                 140

<210> SEQ ID NO 74
<211> LENGTH: 143
<212> TYPE: PRT
<213> ORGANISM: Artificial Sequence
<220> FEATURE:

<223> OTHER INFORMATION: peptidoglycan degrading enzyme

<400> SEQUENCE: 74

Met Ala Ala Ala Ser Leu Gly Cys Glu Val Ala Ala Ile Lys Ala Ile
1               5                   10                  15

Ala Ser Val Glu Thr Lys Gly Ser Ala Trp Ile Thr Pro Gly Val Pro
            20                  25                  30

Gln Ile Leu Tyr Glu Arg His Ile Met Ala Arg Leu Leu Lys Ala Lys
        35                  40                  45

Gly Val Pro Ile Ala Gly Leu Pro Ser Asp Leu Val Asn Thr Thr Pro
50                  55                  60

Gly Gly Tyr Gly Lys Phe Ser Glu Gln His Gly Lys Leu Asp Arg Ala
65                  70                  75                  80

Val Lys Ile Asp Arg Glu Cys Ala Leu Gln Ser Cys Ser Trp Gly Met
                85                  90                  95

Phe Gln Leu Met Gly Phe Asn Tyr Lys Leu Cys Gly Tyr Ala Thr Val
            100                 105                 110

Gln Ala Phe Val Asn Ala Met Tyr Lys Ser Glu Asp Glu Gln Leu Asn
        115                 120                 125

Ala Phe Val Gly Phe Ile Lys Ser Asn Leu Gln Leu Asn Asp Ala
    130                 135                 140

<210> SEQ ID NO 75
<211> LENGTH: 157
<212> TYPE: PRT
<213> ORGANISM: Artificial Sequence
<220> FEATURE:
<223> OTHER INFORMATION: peptidoglycan degrading enzyme

<400> SEQUENCE: 75

Ala Ala Ala Ser Leu Gly Cys Glu Val Ala Ala Ile Lys Ala Ile Ala
1               5                   10                  15

Ser Val Glu Thr Lys Gly Ser Ala Trp Ile Thr Pro Gly Val Pro Gln
            20                  25                  30

Ile Leu Tyr Glu Arg His Ile Met Ala Arg Leu Leu Lys Ala Lys Gly
        35                  40                  45

Val Pro Ile Ala Gly Leu Pro Ser Asp Leu Val Asn Thr Thr Pro Gly
50                  55                  60

Gly Tyr Gly Lys Phe Ser Glu Gln His Gly Lys Leu Asp Arg Ala Val
65                  70                  75                  80

Lys Ile Asp Arg Glu Cys Ala Leu Gln Ser Cys Ser Trp Gly Met Phe
                85                  90                  95

Gln Leu Met Gly Phe Asn Tyr Lys Leu Cys Gly Tyr Ala Thr Val Gln
            100                 105                 110

Ala Phe Val Asn Ala Met Tyr Lys Ser Glu Asp Glu Gln Leu Asn Ala
        115                 120                 125

Phe Val Gly Phe Ile Lys Ser Asn Leu Gln Leu Asn Asp Ala Leu Lys
    130                 135                 140

Ser Lys Asp Trp Ala Thr Val Ala Arg Leu Tyr Asn Gly
145                 150                 155

<210> SEQ ID NO 76
<211> LENGTH: 158
<212> TYPE: PRT
<213> ORGANISM: Artificial Sequence
<220> FEATURE:
<223> OTHER INFORMATION: peptidoglycan degrading enzyme

<400> SEQUENCE: 76

Met Ala Ala Ala Ser Leu Gly Cys Glu Val Ala Ala Ile Lys Ala Ile
1               5                   10                  15

Ala Ser Val Glu Thr Lys Gly Ser Ala Trp Ile Thr Pro Gly Val Pro
            20                  25                  30

Gln Ile Leu Tyr Glu Arg His Ile Met Ala Arg Leu Leu Lys Ala Lys
        35                  40                  45

Gly Val Pro Ile Ala Gly Leu Pro Ser Asp Leu Val Asn Thr Thr Pro
50                  55                  60

Gly Gly Tyr Gly Lys Phe Ser Glu Gln His Gly Lys Leu Asp Arg Ala
65                  70                  75                  80

Val Lys Ile Asp Arg Glu Cys Ala Leu Gln Ser Cys Ser Trp Gly Met
                85                  90                  95

Phe Gln Leu Met Gly Phe Asn Tyr Lys Leu Cys Gly Tyr Ala Thr Val
            100                 105                 110

Gln Ala Phe Val Asn Ala Met Tyr Lys Ser Glu Asp Glu Gln Leu Asn
        115                 120                 125

Ala Phe Val Gly Phe Ile Lys Ser Asn Leu Gln Leu Asn Asp Ala Leu
    130                 135                 140

Lys Ser Lys Asp Trp Ala Thr Val Ala Arg Leu Tyr Asn Gly
145                 150                 155

<210> SEQ ID NO 77
<211> LENGTH: 168
<212> TYPE: PRT
<213> ORGANISM: Artificial Sequence
<220> FEATURE:
<223> OTHER INFORMATION: peptidoglycan degrading enzyme

<400> SEQUENCE: 77

Ala Ala Ala Ser Leu Gly Cys Glu Val Ala Ala Ile Lys Ala Ile Ala
1               5                   10                  15

Ser Val Glu Thr Lys Gly Ser Ala Trp Ile Thr Pro Gly Val Pro Gln
            20                  25                  30

Ile Leu Tyr Glu Arg His Ile Met Ala Arg Leu Leu Lys Ala Lys Gly
        35                  40                  45

Val Pro Ile Ala Gly Leu Pro Ser Asp Leu Val Asn Thr Thr Pro Gly
50                  55                  60

Gly Tyr Gly Lys Phe Ser Glu Gln His Gly Lys Leu Asp Arg Ala Val
65                  70                  75                  80

Lys Ile Asp Arg Glu Cys Ala Leu Gln Ser Cys Ser Trp Gly Met Phe
                85                  90                  95

Gln Leu Met Gly Phe Asn Tyr Lys Leu Cys Gly Tyr Ala Thr Val Gln
            100                 105                 110

Ala Phe Val Asn Ala Met Tyr Lys Ser Glu Asp Glu Gln Leu Asn Ala
        115                 120                 125

Phe Val Gly Phe Ile Lys Ser Asn Leu Gln Leu Asn Asp Ala Leu Lys
    130                 135                 140

Ser Lys Asp Trp Ala Thr Val Ala Arg Leu Tyr Asn Gly Ala Asp Tyr
145                 150                 155                 160

Lys Ile Asn Ser Tyr Asp Gln Lys
                165

<210> SEQ ID NO 78
<211> LENGTH: 169
<212> TYPE: PRT

```
<213> ORGANISM: Artificial Sequence
<220> FEATURE:
<223> OTHER INFORMATION: peptidoglycan degrading enzyme

<400> SEQUENCE: 78

Met Ala Ala Ala Ser Leu Gly Cys Glu Val Ala Ile Lys Ala Ile
1               5                   10                  15

Ala Ser Val Glu Thr Lys Gly Ser Ala Trp Ile Thr Pro Gly Val Pro
            20                  25                  30

Gln Ile Leu Tyr Glu Arg His Ile Met Ala Arg Leu Leu Lys Ala Lys
        35                  40                  45

Gly Val Pro Ile Ala Gly Leu Pro Ser Asp Leu Val Asn Thr Thr Pro
50                  55                  60

Gly Gly Tyr Gly Lys Phe Ser Glu Gln His Gly Lys Leu Asp Arg Ala
65                  70                  75                  80

Val Lys Ile Asp Arg Glu Cys Ala Leu Gln Ser Cys Ser Trp Gly Met
                85                  90                  95

Phe Gln Leu Met Gly Phe Asn Tyr Lys Leu Cys Gly Tyr Ala Thr Val
            100                 105                 110

Gln Ala Phe Val Asn Ala Met Tyr Lys Ser Glu Asp Glu Gln Leu Asn
        115                 120                 125

Ala Phe Val Gly Phe Ile Lys Ser Asn Leu Gln Leu Asn Asp Ala Leu
130                 135                 140

Lys Ser Lys Asp Trp Ala Thr Val Ala Arg Leu Tyr Asn Gly Ala Asp
145                 150                 155                 160

Tyr Lys Ile Asn Ser Tyr Asp Gln Lys
                165

<210> SEQ ID NO 79
<211> LENGTH: 134
<212> TYPE: PRT
<213> ORGANISM: Artificial Sequence
<220> FEATURE:
<223> OTHER INFORMATION: peptidoglycan degrading enzyme

<400> SEQUENCE: 79

Val Ala Ala Ile Lys Ala Ile Ala Ser Val Glu Thr Lys Gly Ser Ala
1               5                   10                  15

Trp Ile Thr Pro Gly Val Pro Gln Ile Leu Tyr Glu Arg His Ile Met
            20                  25                  30

Ala Arg Leu Leu Lys Ala Lys Gly Val Pro Ile Ala Gly Leu Pro Ser
        35                  40                  45

Asp Leu Val Asn Thr Thr Pro Gly Gly Tyr Gly Lys Phe Ser Glu Gln
    50                  55                  60

His Gly Lys Leu Asp Arg Ala Val Lys Ile Asp Arg Glu Cys Ala Leu
65                  70                  75                  80

Gln Ser Cys Ser Trp Gly Met Phe Gln Leu Met Gly Phe Asn Tyr Lys
                85                  90                  95

Leu Cys Gly Tyr Ala Thr Val Gln Ala Phe Val Asn Ala Met Tyr Lys
            100                 105                 110

Ser Glu Asp Glu Gln Leu Asn Ala Phe Val Gly Phe Ile Lys Ser Asn
        115                 120                 125

Leu Gln Leu Asn Asp Ala
    130

<210> SEQ ID NO 80
<211> LENGTH: 135
```

```
<212> TYPE: PRT
<213> ORGANISM: Artificial Sequence
<220> FEATURE:
<223> OTHER INFORMATION: peptidoglycan degrading enzyme

<400> SEQUENCE: 80

Met Val Ala Ala Ile Lys Ala Ile Ala Ser Val Glu Thr Lys Gly Ser
1               5                   10                  15

Ala Trp Ile Thr Pro Gly Val Pro Gln Ile Leu Tyr Glu Arg His Ile
            20                  25                  30

Met Ala Arg Leu Leu Lys Ala Lys Gly Val Pro Ile Ala Gly Leu Pro
        35                  40                  45

Ser Asp Leu Val Asn Thr Thr Pro Gly Gly Tyr Gly Lys Phe Ser Glu
    50                  55                  60

Gln His Gly Lys Leu Asp Arg Ala Val Lys Ile Asp Arg Glu Cys Ala
65                  70                  75                  80

Leu Gln Ser Cys Ser Trp Gly Met Phe Gln Leu Met Gly Phe Asn Tyr
                85                  90                  95

Lys Leu Cys Gly Tyr Ala Thr Val Gln Ala Phe Val Asn Ala Met Tyr
            100                 105                 110

Lys Ser Glu Asp Glu Gln Leu Asn Ala Phe Val Gly Phe Ile Lys Ser
        115                 120                 125

Asn Leu Gln Leu Asn Asp Ala
    130                 135

<210> SEQ ID NO 81
<211> LENGTH: 146
<212> TYPE: PRT
<213> ORGANISM: Artificial Sequence
<220> FEATURE:
<223> OTHER INFORMATION: peptidoglycan degrading enzyme

<400> SEQUENCE: 81

Ile Leu Tyr Glu Arg His Ile Met Ala Arg Leu Leu Lys Ala Lys Gly
1               5                   10                  15

Val Pro Ile Ala Gly Leu Pro Ser Asp Leu Val Asn Thr Thr Pro Gly
            20                  25                  30

Gly Tyr Gly Lys Phe Ser Glu Gln His Gly Lys Leu Asp Arg Ala Val
        35                  40                  45

Lys Ile Asp Arg Glu Cys Ala Leu Gln Ser Cys Ser Trp Gly Met Phe
    50                  55                  60

Gln Leu Met Gly Phe Asn Tyr Lys Leu Cys Gly Tyr Ala Thr Val Gln
65                  70                  75                  80

Ala Phe Val Asn Ala Met Tyr Lys Ser Glu Asp Glu Gln Leu Asn Ala
                85                  90                  95

Phe Val Gly Phe Ile Lys Ser Asn Leu Gln Leu Asn Asp Ala Leu Lys
            100                 105                 110

Ser Lys Asp Trp Ala Thr Val Ala Arg Leu Tyr Asn Gly Ala Asp Tyr
        115                 120                 125

Lys Ile Asn Ser Tyr Asp Gln Lys Leu Ala Val Ala Tyr Glu Ser Asn
    130                 135                 140

Lys Arg
145

<210> SEQ ID NO 82
<211> LENGTH: 147
<212> TYPE: PRT
<213> ORGANISM: Artificial Sequence
```

<220> FEATURE:
<223> OTHER INFORMATION: peptidoglycan degrading enzyme

<400> SEQUENCE: 82

```
Met Ile Leu Tyr Glu Arg His Ile Met Ala Arg Leu Leu Lys Ala Lys
1               5                  10                  15
Gly Val Pro Ile Ala Gly Leu Pro Ser Asp Leu Val Asn Thr Thr Pro
            20                  25                  30
Gly Gly Tyr Gly Lys Phe Ser Glu Gln His Gly Lys Leu Asp Arg Ala
        35                  40                  45
Val Lys Ile Asp Arg Glu Cys Ala Leu Gln Ser Cys Ser Trp Gly Met
    50                  55                  60
Phe Gln Leu Met Gly Phe Asn Tyr Lys Leu Cys Gly Tyr Ala Thr Val
65                  70                  75                  80
Gln Ala Phe Val Asn Ala Met Tyr Lys Ser Glu Asp Glu Gln Leu Asn
                85                  90                  95
Ala Phe Val Gly Phe Ile Lys Ser Asn Leu Gln Leu Asn Asp Ala Leu
            100                 105                 110
Lys Ser Lys Asp Trp Ala Thr Val Ala Arg Leu Tyr Asn Gly Ala Asp
        115                 120                 125
Tyr Lys Ile Asn Ser Tyr Asp Gln Lys Leu Ala Val Ala Tyr Glu Ser
    130                 135                 140
Asn Lys Arg
145
```

<210> SEQ ID NO 83
<211> LENGTH: 138
<212> TYPE: PRT
<213> ORGANISM: Artificial Sequence
<220> FEATURE:
<223> OTHER INFORMATION: peptidoglycan degrading enzyme

<400> SEQUENCE: 83

```
Ala Arg Leu Leu Lys Ala Lys Gly Val Pro Ile Ala Gly Leu Pro Ser
1               5                  10                  15
Asp Leu Val Asn Thr Thr Pro Gly Gly Tyr Gly Lys Phe Ser Glu Gln
            20                  25                  30
His Gly Lys Leu Asp Arg Ala Val Lys Ile Asp Arg Glu Cys Ala Leu
        35                  40                  45
Gln Ser Cys Ser Trp Gly Met Phe Gln Leu Met Gly Phe Asn Tyr Lys
    50                  55                  60
Leu Cys Gly Tyr Ala Thr Val Gln Ala Phe Val Asn Ala Met Tyr Lys
65                  70                  75                  80
Ser Glu Asp Glu Gln Leu Asn Ala Phe Val Gly Phe Ile Lys Ser Asn
                85                  90                  95
Leu Gln Leu Asn Asp Ala Leu Lys Ser Lys Asp Trp Ala Thr Val Ala
            100                 105                 110
Arg Leu Tyr Asn Gly Ala Asp Tyr Lys Ile Asn Ser Tyr Asp Gln Lys
        115                 120                 125
Leu Ala Val Ala Tyr Glu Ser Asn Lys Arg
    130                 135
```

<210> SEQ ID NO 84
<211> LENGTH: 139
<212> TYPE: PRT
<213> ORGANISM: Artificial Sequence
<220> FEATURE:
<223> OTHER INFORMATION: peptidoglycan degrading enzyme

<400> SEQUENCE: 84

Met Ala Arg Leu Leu Lys Ala Lys Gly Val Pro Ile Ala Gly Leu Pro
1               5                   10                  15

Ser Asp Leu Val Asn Thr Thr Pro Gly Gly Tyr Gly Lys Phe Ser Glu
            20                  25                  30

Gln His Gly Lys Leu Asp Arg Ala Val Lys Ile Asp Arg Glu Cys Ala
        35                  40                  45

Leu Gln Ser Cys Ser Trp Gly Met Phe Gln Leu Met Gly Phe Asn Tyr
    50                  55                  60

Lys Leu Cys Gly Tyr Ala Thr Val Gln Ala Phe Val Asn Ala Met Tyr
65                  70                  75                  80

Lys Ser Glu Asp Glu Gln Leu Asn Ala Phe Val Gly Phe Ile Lys Ser
                85                  90                  95

Asn Leu Gln Leu Asn Asp Ala Leu Lys Ser Lys Asp Trp Ala Thr Val
            100                 105                 110

Ala Arg Leu Tyr Asn Gly Ala Asp Tyr Lys Ile Asn Ser Tyr Asp Gln
        115                 120                 125

Lys Leu Ala Val Ala Tyr Glu Ser Asn Lys Arg
    130                 135

<210> SEQ ID NO 85
<211> LENGTH: 167
<212> TYPE: PRT
<213> ORGANISM: Artificial Sequence
<220> FEATURE:
<223> OTHER INFORMATION: peptidoglycan degrading enzyme

<400> SEQUENCE: 85

Ile Lys Ala Ile Ala Ser Val Glu Thr Lys Gly Ser Ala Trp Ile Thr
1               5                   10                  15

Pro Gly Val Pro Gln Ile Leu Tyr Glu Arg His Ile Met Ala Arg Leu
            20                  25                  30

Leu Lys Ala Lys Gly Val Pro Ile Ala Gly Leu Pro Ser Asp Leu Val
        35                  40                  45

Asn Thr Thr Pro Gly Gly Tyr Gly Lys Phe Ser Glu Gln His Gly Lys
    50                  55                  60

Leu Asp Arg Ala Val Lys Ile Asp Arg Glu Cys Ala Leu Gln Ser Cys
65                  70                  75                  80

Ser Trp Gly Met Phe Gln Leu Met Gly Phe Asn Tyr Lys Leu Cys Gly
                85                  90                  95

Tyr Ala Thr Val Gln Ala Phe Val Asn Ala Met Tyr Lys Ser Glu Asp
            100                 105                 110

Glu Gln Leu Asn Ala Phe Val Gly Phe Ile Lys Ser Asn Leu Gln Leu
        115                 120                 125

Asn Asp Ala Leu Lys Ser Lys Asp Trp Ala Thr Val Ala Arg Leu Tyr
    130                 135                 140

Asn Gly Ala Asp Tyr Lys Ile Asn Ser Tyr Asp Gln Lys Leu Ala Val
145                 150                 155                 160

Ala Tyr Glu Ser Asn Lys Arg
                165

<210> SEQ ID NO 86
<211> LENGTH: 168
<212> TYPE: PRT
<213> ORGANISM: Artificial Sequence
<220> FEATURE:

<223> OTHER INFORMATION: peptidoglycan degrading enzyme

<400> SEQUENCE: 86

Met Ile Lys Ala Ile Ala Ser Val Glu Thr Lys Gly Ser Ala Trp Ile
1               5                   10                  15

Thr Pro Gly Val Pro Gln Ile Leu Tyr Glu Arg His Ile Met Ala Arg
            20                  25                  30

Leu Leu Lys Ala Lys Gly Val Pro Ile Ala Gly Leu Pro Ser Asp Leu
        35                  40                  45

Val Asn Thr Thr Pro Gly Gly Tyr Gly Lys Phe Ser Glu Gln His Gly
50                  55                  60

Lys Leu Asp Arg Ala Val Lys Ile Asp Arg Glu Cys Ala Leu Gln Ser
65                  70                  75                  80

Cys Ser Trp Gly Met Phe Gln Leu Met Gly Phe Asn Tyr Lys Leu Cys
                85                  90                  95

Gly Tyr Ala Thr Val Gln Ala Phe Val Asn Ala Met Tyr Lys Ser Glu
            100                 105                 110

Asp Glu Gln Leu Asn Ala Phe Val Gly Phe Ile Lys Ser Asn Leu Gln
        115                 120                 125

Leu Asn Asp Ala Leu Lys Ser Lys Asp Trp Ala Thr Val Ala Arg Leu
130                 135                 140

Tyr Asn Gly Ala Asp Tyr Lys Ile Asn Ser Tyr Asp Gln Lys Leu Ala
145                 150                 155                 160

Val Ala Tyr Glu Ser Asn Lys Arg
                165

<210> SEQ ID NO 87
<211> LENGTH: 178
<212> TYPE: PRT
<213> ORGANISM: Artificial Sequence
<220> FEATURE:
<223> OTHER INFORMATION: peptidoglycan degrading enzyme

<400> SEQUENCE: 87

Ala Ala Ala Ser Leu Gly Cys Glu Val Ala Ala Ile Lys Ala Ile Ala
1               5                   10                  15

Ser Val Glu Thr Lys Gly Ser Ala Trp Ile Thr Pro Gly Val Pro Gln
            20                  25                  30

Ile Leu Tyr Glu Arg His Ile Met Ala Arg Leu Leu Lys Ala Lys Gly
        35                  40                  45

Val Pro Ile Ala Gly Leu Pro Ser Asp Leu Val Asn Thr Thr Pro Gly
50                  55                  60

Gly Tyr Gly Lys Phe Ser Glu Gln His Gly Lys Leu Asp Arg Ala Val
65                  70                  75                  80

Lys Ile Asp Arg Glu Cys Ala Leu Gln Ser Cys Ser Trp Gly Met Phe
                85                  90                  95

Gln Leu Met Gly Phe Asn Tyr Lys Leu Cys Gly Tyr Ala Thr Val Gln
            100                 105                 110

Ala Phe Val Asn Ala Met Tyr Lys Ser Glu Asp Glu Gln Leu Asn Ala
        115                 120                 125

Phe Val Gly Phe Ile Lys Ser Asn Leu Gln Leu Asn Asp Ala Leu Lys
130                 135                 140

Ser Lys Asp Trp Ala Thr Val Ala Arg Leu Tyr Asn Gly Ala Asp Tyr
145                 150                 155                 160

Lys Ile Asn Ser Tyr Asp Gln Lys Leu Ala Val Ala Tyr Glu Ser Asn
                165                 170                 175

Lys Arg

<210> SEQ ID NO 88
<211> LENGTH: 179
<212> TYPE: PRT
<213> ORGANISM: artificial
<220> FEATURE:
<223> OTHER INFORMATION: peptidoglycan degrading enzyme

<400> SEQUENCE: 88

```
Met Ala Ala Ala Ser Leu Gly Cys Glu Val Ala Ala Ile Lys Ala Ile
1               5                   10                  15

Ala Ser Val Glu Thr Lys Gly Ser Ala Trp Ile Thr Pro Gly Val Pro
            20                  25                  30

Gln Ile Leu Tyr Glu Arg His Ile Met Ala Arg Leu Leu Lys Ala Lys
        35                  40                  45

Gly Val Pro Ile Ala Gly Leu Pro Ser Asp Leu Val Asn Thr Thr Pro
    50                  55                  60

Gly Gly Tyr Gly Lys Phe Ser Glu Gln His Gly Lys Leu Asp Arg Ala
65                  70                  75                  80

Val Lys Ile Asp Arg Glu Cys Ala Leu Gln Ser Cys Ser Trp Gly Met
                85                  90                  95

Phe Gln Leu Met Gly Phe Asn Tyr Lys Leu Cys Gly Tyr Ala Thr Val
            100                 105                 110

Gln Ala Phe Val Asn Ala Met Tyr Lys Ser Glu Asp Glu Gln Leu Asn
        115                 120                 125

Ala Phe Val Gly Phe Ile Lys Ser Asn Leu Gln Leu Asn Asp Ala Leu
    130                 135                 140

Lys Ser Lys Asp Trp Ala Thr Val Ala Arg Leu Tyr Asn Gly Ala Asp
145                 150                 155                 160

Tyr Lys Ile Asn Ser Tyr Asp Gln Lys Leu Ala Val Ala Tyr Glu Ser
                165                 170                 175

Asn Lys Arg
```

<210> SEQ ID NO 89
<211> LENGTH: 183
<212> TYPE: PRT
<213> ORGANISM: artificial
<220> FEATURE:
<223> OTHER INFORMATION: peptidoglycan degrading enzyme

<400> SEQUENCE: 89

```
Lys Ser Phe Val Glu Ala Ala Ser Leu Gly Cys Glu Val Ala Ala
1               5                   10                  15

Ile Lys Ala Ile Ala Ser Val Glu Thr Lys Gly Ser Ala Trp Ile Thr
            20                  25                  30

Pro Gly Val Pro Gln Ile Leu Tyr Glu Arg His Ile Met Ala Arg Leu
        35                  40                  45

Leu Lys Ala Lys Gly Val Pro Ile Ala Gly Leu Pro Ser Asp Leu Val
    50                  55                  60

Asn Thr Thr Pro Gly Gly Tyr Gly Lys Phe Ser Glu Gln His Gly Lys
65                  70                  75                  80

Leu Asp Arg Ala Val Lys Ile Asp Arg Glu Cys Ala Leu Gln Ser Cys
                85                  90                  95

Ser Trp Gly Met Phe Gln Leu Met Gly Phe Asn Tyr Lys Leu Cys Gly
            100                 105                 110
```

```
Tyr Ala Thr Val Gln Ala Phe Val Asn Ala Met Tyr Lys Ser Glu Asp
            115                 120                 125

Glu Gln Leu Asn Ala Phe Val Gly Phe Ile Lys Ser Asn Leu Gln Leu
    130                 135                 140

Asn Asp Ala Leu Lys Ser Lys Asp Trp Ala Thr Val Ala Arg Leu Tyr
145                 150                 155                 160

Asn Gly Ala Asp Tyr Lys Ile Asn Ser Tyr Asp Gln Lys Leu Ala Val
                165                 170                 175

Ala Tyr Glu Ser Asn Lys Arg
            180

<210> SEQ ID NO 90
<211> LENGTH: 184
<212> TYPE: PRT
<213> ORGANISM: artificial
<220> FEATURE:
<223> OTHER INFORMATION: peptidoglycan degrading enzyme

<400> SEQUENCE: 90

Met Lys Ser Phe Val Glu Ala Ala Ser Leu Gly Cys Glu Val Ala
1               5                   10                  15

Ala Ile Lys Ala Ile Ala Ser Val Glu Thr Lys Gly Ser Ala Trp Ile
            20                  25                  30

Thr Pro Gly Val Pro Gln Ile Leu Tyr Glu Arg His Ile Met Ala Arg
        35                  40                  45

Leu Leu Lys Ala Lys Gly Val Pro Ile Ala Gly Leu Pro Ser Asp Leu
    50                  55                  60

Val Asn Thr Thr Pro Gly Gly Tyr Gly Lys Phe Ser Glu Gln His Gly
65                  70                  75                  80

Lys Leu Asp Arg Ala Val Lys Ile Asp Arg Glu Cys Ala Leu Gln Ser
                85                  90                  95

Cys Ser Trp Gly Met Phe Gln Leu Met Gly Phe Asn Tyr Lys Leu Cys
            100                 105                 110

Gly Tyr Ala Thr Val Gln Ala Phe Val Asn Ala Met Tyr Lys Ser Glu
        115                 120                 125

Asp Glu Gln Leu Asn Ala Phe Val Gly Phe Ile Lys Ser Asn Leu Gln
    130                 135                 140

Leu Asn Asp Ala Leu Lys Ser Lys Asp Trp Ala Thr Val Ala Arg Leu
145                 150                 155                 160

Tyr Asn Gly Ala Asp Tyr Lys Ile Asn Ser Tyr Asp Gln Lys Leu Ala
                165                 170                 175

Val Ala Tyr Glu Ser Asn Lys Arg
            180

<210> SEQ ID NO 91
<211> LENGTH: 186
<212> TYPE: PRT
<213> ORGANISM: Artificial Sequence
<220> FEATURE:
<223> OTHER INFORMATION: peptidoglycan degrading enzyme

<400> SEQUENCE: 91

Leu Ser Glu Lys Ser Phe Val Glu Ala Ala Ser Leu Gly Cys Glu
1               5                   10                  15

Val Ala Ala Ile Lys Ala Ile Ala Ser Val Glu Thr Lys Gly Ser Ala
            20                  25                  30

Trp Ile Thr Pro Gly Val Pro Gln Ile Leu Tyr Glu Arg His Ile Met
        35                  40                  45
```

```
Ala Arg Leu Leu Lys Ala Lys Gly Val Pro Ile Ala Gly Leu Pro Ser
        50                  55                  60

Asp Leu Val Asn Thr Thr Pro Gly Gly Tyr Gly Lys Phe Ser Glu Gln
 65                  70                  75                  80

His Gly Lys Leu Asp Arg Ala Val Lys Ile Asp Arg Glu Cys Ala Leu
                 85                  90                  95

Gln Ser Cys Ser Trp Gly Met Phe Gln Leu Met Gly Phe Asn Tyr Lys
                100                 105                 110

Leu Cys Gly Tyr Ala Thr Val Gln Ala Phe Val Asn Ala Met Tyr Lys
                115                 120                 125

Ser Glu Asp Glu Gln Leu Asn Ala Phe Val Gly Phe Ile Lys Ser Asn
                130                 135                 140

Leu Gln Leu Asn Asp Ala Leu Lys Ser Lys Asp Trp Ala Thr Val Ala
145                 150                 155                 160

Arg Leu Tyr Asn Gly Ala Asp Tyr Lys Ile Asn Ser Tyr Asp Gln Lys
                165                 170                 175

Leu Ala Val Ala Tyr Glu Ser Asn Lys Arg
                180                 185
```

<210> SEQ ID NO 92
<211> LENGTH: 187
<212> TYPE: PRT
<213> ORGANISM: unknown
<220> FEATURE:
<223> OTHER INFORMATION: peptidoglycan degrading enzyme

<400> SEQUENCE: 92

```
Met Leu Ser Glu Lys Ser Phe Val Glu Ala Ala Ser Leu Gly Cys
 1               5                  10                  15

Glu Val Ala Ala Ile Lys Ala Ile Ala Ser Val Glu Thr Lys Gly Ser
                 20                  25                  30

Ala Trp Ile Thr Pro Gly Val Pro Gln Ile Leu Tyr Glu Arg His Ile
                 35                  40                  45

Met Ala Arg Leu Leu Lys Ala Lys Gly Val Pro Ile Ala Gly Leu Pro
         50                  55                  60

Ser Asp Leu Val Asn Thr Thr Pro Gly Gly Tyr Gly Lys Phe Ser Glu
 65                  70                  75                  80

Gln His Gly Lys Leu Asp Arg Ala Val Lys Ile Asp Arg Glu Cys Ala
                 85                  90                  95

Leu Gln Ser Cys Ser Trp Gly Met Phe Gln Leu Met Gly Phe Asn Tyr
                100                 105                 110

Lys Leu Cys Gly Tyr Ala Thr Val Gln Ala Phe Val Asn Ala Met Tyr
                115                 120                 125

Lys Ser Glu Asp Glu Gln Leu Asn Ala Phe Val Gly Phe Ile Lys Ser
                130                 135                 140

Asn Leu Gln Leu Asn Asp Ala Leu Lys Ser Lys Asp Trp Ala Thr Val
145                 150                 155                 160

Ala Arg Leu Tyr Asn Gly Ala Asp Tyr Lys Ile Asn Ser Tyr Asp Gln
                165                 170                 175

Lys Leu Ala Val Ala Tyr Glu Ser Asn Lys Arg
                180                 185
```

<210> SEQ ID NO 93
<211> LENGTH: 6
<212> TYPE: PRT
<213> ORGANISM: artificial

```
<220> FEATURE:
<223> OTHER INFORMATION: synthetic sequence

<400> SEQUENCE: 93

Lys Arg Lys Lys Arg Lys
1               5

<210> SEQ ID NO 94
<211> LENGTH: 5
<212> TYPE: PRT
<213> ORGANISM: artificial
<220> FEATURE:
<223> OTHER INFORMATION: synethtic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 94

Lys Arg Xaa Lys Arg
1               5

<210> SEQ ID NO 95
<211> LENGTH: 5
<212> TYPE: PRT
<213> ORGANISM: artificial
<220> FEATURE:
<223> OTHER INFORMATION: synthetic sequence

<400> SEQUENCE: 95

Lys Arg Ser Lys Arg
1               5

<210> SEQ ID NO 96
<211> LENGTH: 5
<212> TYPE: PRT
<213> ORGANISM: artificial
<220> FEATURE:
<223> OTHER INFORMATION: synthetic sequence

<400> SEQUENCE: 96

Lys Arg Gly Ser Gly
1               5

<210> SEQ ID NO 97
<211> LENGTH: 9
<212> TYPE: PRT
<213> ORGANISM: artificial
<220> FEATURE:
<223> OTHER INFORMATION: synthetic sequence

<400> SEQUENCE: 97

Lys Arg Lys Lys Arg Lys Lys Arg Lys
1               5

<210> SEQ ID NO 98
<211> LENGTH: 9
<212> TYPE: PRT
<213> ORGANISM: artificial
<220> FEATURE:
<223> OTHER INFORMATION: synthetic sequence

<400> SEQUENCE: 98

Arg Arg Arg Arg Arg Arg Arg Arg
1               5

<210> SEQ ID NO 99
```

```
<211> LENGTH: 8
<212> TYPE: PRT
<213> ORGANISM: artificial
<220> FEATURE:
<223> OTHER INFORMATION: synthetic sequence

<400> SEQUENCE: 99

Lys Lys Lys Lys Lys Lys Lys Lys
1               5

<210> SEQ ID NO 100
<211> LENGTH: 10
<212> TYPE: PRT
<213> ORGANISM: artificial
<220> FEATURE:
<223> OTHER INFORMATION: synthetic sequence

<400> SEQUENCE: 100

Lys Arg Lys Lys Arg Lys Lys Arg Lys Lys
1               5                   10

<210> SEQ ID NO 101
<211> LENGTH: 12
<212> TYPE: PRT
<213> ORGANISM: artificial
<220> FEATURE:
<223> OTHER INFORMATION: synthetic sequence

<400> SEQUENCE: 101

Lys Arg Lys Lys Arg Lys Lys Arg Lys Lys Arg Lys
1               5                   10

<210> SEQ ID NO 102
<211> LENGTH: 14
<212> TYPE: PRT
<213> ORGANISM: artificial
<220> FEATURE:
<223> OTHER INFORMATION: synthetic sequence

<400> SEQUENCE: 102

Lys Arg Lys Lys Arg Lys Lys Arg Lys Lys Arg Lys Lys Arg
1               5                   10

<210> SEQ ID NO 103
<211> LENGTH: 16
<212> TYPE: PRT
<213> ORGANISM: artificial
<220> FEATURE:
<223> OTHER INFORMATION: synthetic sequence

<400> SEQUENCE: 103

Lys Lys Lys Lys Lys Lys Lys Lys Lys Lys Lys Lys Lys Lys Lys Lys
1               5                   10                  15

<210> SEQ ID NO 104
<211> LENGTH: 18
<212> TYPE: PRT
<213> ORGANISM: artificial
<220> FEATURE:
<223> OTHER INFORMATION: synthetic sequence

<400> SEQUENCE: 104

Lys Arg Lys Lys Arg Lys Lys Arg Lys Lys Arg Lys Lys Arg Lys Lys
1               5                   10                  15

Arg Lys
```

<210> SEQ ID NO 105
<211> LENGTH: 19
<212> TYPE: PRT
<213> ORGANISM: artificial
<220> FEATURE:
<223> OTHER INFORMATION: synthetic sequence

<400> SEQUENCE: 105

Lys Arg Lys Lys Arg Lys Lys Arg Lys Lys Arg Lys Lys Arg Lys Lys
1               5                   10                  15

Arg Lys Lys

<210> SEQ ID NO 106
<211> LENGTH: 19
<212> TYPE: PRT
<213> ORGANISM: artificial
<220> FEATURE:
<223> OTHER INFORMATION: synthetic sequence

<400> SEQUENCE: 106

Arg Arg Arg Arg Arg Arg Arg Arg Arg Arg Arg Arg Arg Arg Arg Arg
1               5                   10                  15

Arg Arg Arg

<210> SEQ ID NO 107
<211> LENGTH: 19
<212> TYPE: PRT
<213> ORGANISM: artificial
<220> FEATURE:
<223> OTHER INFORMATION: synthetic sequence

<400> SEQUENCE: 107

Lys Lys Lys Lys Lys Lys Lys Lys Lys Lys Lys Lys Lys Lys Lys Lys
1               5                   10                  15

Lys Lys Lys

<210> SEQ ID NO 108
<211> LENGTH: 20
<212> TYPE: PRT
<213> ORGANISM: artificial
<220> FEATURE:
<223> OTHER INFORMATION: synthetic sequence

<400> SEQUENCE: 108

Lys Arg Lys Lys Arg Lys Lys Arg Lys Arg Ser Lys Arg Lys Lys Arg
1               5                   10                  15

Lys Lys Arg Lys
            20

<210> SEQ ID NO 109
<211> LENGTH: 21
<212> TYPE: PRT
<213> ORGANISM: artificial
<220> FEATURE:
<223> OTHER INFORMATION: synthetic sequence

<400> SEQUENCE: 109

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 110
<211> LENGTH: 21

```
<212> TYPE: PRT
<213> ORGANISM: artificial
<220> FEATURE:
<223> OTHER INFORMATION: synthetic sequence

<400> SEQUENCE: 110

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 111
<211> LENGTH: 22
<212> TYPE: PRT
<213> ORGANISM: artificial
<220> FEATURE:
<223> OTHER INFORMATION: synthetic sequence

<400> SEQUENCE: 111

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 112
<211> LENGTH: 24
<212> TYPE: PRT
<213> ORGANISM: artificial
<220> FEATURE:
<223> OTHER INFORMATION: synthetic sequence

<400> SEQUENCE: 112

Lys Arg Lys Lys Arg Lys Lys Arg Lys Arg Gly Ser Gly Ser Gly Lys
1               5                   10                  15

Arg Lys Lys Arg Lys Lys Arg Lys
            20

<210> SEQ ID NO 113
<211> LENGTH: 25
<212> TYPE: PRT
<213> ORGANISM: artificial
<220> FEATURE:
<223> OTHER INFORMATION: synthetic sequence

<400> SEQUENCE: 113

Lys Arg Lys Lys Arg Lys Lys Arg Lys Lys Arg Lys Lys Arg Lys Lys
1               5                   10                  15

Arg Lys Lys Arg Lys Lys Arg Lys Lys
            20                  25

<210> SEQ ID NO 114
<211> LENGTH: 31
<212> TYPE: PRT
<213> ORGANISM: artificial
<220> FEATURE:
<223> OTHER INFORMATION: synthetic sequence

<400> SEQUENCE: 114

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30

<210> SEQ ID NO 115
```

```
<211> LENGTH: 38
<212> TYPE: PRT
<213> ORGANISM: artificial
<220> FEATURE:
<223> OTHER INFORMATION: synthetic sequence

<400> SEQUENCE: 115
```

Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
                20                  25                  30

Lys Arg Lys Lys Arg Lys
        35

```
<210> SEQ ID NO 116
<211> LENGTH: 39
<212> TYPE: PRT
<213> ORGANISM: artificial
<220> FEATURE:
<223> OTHER INFORMATION: synthetic sequence

<400> SEQUENCE: 116
```

Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
                20                  25                  30

Lys Lys Arg Lys Lys Arg Lys
        35

```
<210> SEQ ID NO 117
<211> LENGTH: 42
<212> TYPE: PRT
<213> ORGANISM: artificial
<220> FEATURE:
<223> OTHER INFORMATION: synthetic sequence

<400> SEQUENCE: 117
```

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys Arg
                20                  25                  30

Ser Lys Arg Lys Lys Arg Lys Lys Arg Lys
        35                  40

```
<210> SEQ ID NO 118
<211> LENGTH: 37
<212> TYPE: PRT
<213> ORGANISM: Homo sapiens

<400> SEQUENCE: 118
```

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
        35

```
<210> SEQ ID NO 119
<211> LENGTH: 29
<212> TYPE: PRT
<213> ORGANISM: unknown
<220> FEATURE:
<223> OTHER INFORMATION: SMAP-29 sheep
```

<400> SEQUENCE: 119

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 120
<211> LENGTH: 13
<212> TYPE: PRT
<213> ORGANISM: unknown
<220> FEATURE:
<223> OTHER INFORMATION: Indolicidine bovine

<400> SEQUENCE: 120

Ile Leu Pro Trp Lys Trp Pro Trp Trp Pro Trp Arg Arg
1               5                   10

<210> SEQ ID NO 121
<211> LENGTH: 18
<212> TYPE: PRT
<213> ORGANISM: unknown
<220> FEATURE:
<223> OTHER INFORMATION: Protegrin Porcine

<400> SEQUENCE: 121

Arg Gly Gly Arg Leu Cys Tyr Cys Arg Arg Arg Phe Cys Val Cys Val
1               5                   10                  15

Gly Arg

<210> SEQ ID NO 122
<211> LENGTH: 31
<212> TYPE: PRT
<213> ORGANISM: unknown
<220> FEATURE:
<223> OTHER INFORMATION: Cecropin P1 Mammal (pig)

<400> SEQUENCE: 122

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 123
<211> LENGTH: 23
<212> TYPE: PRT
<213> ORGANISM: unknown
<220> FEATURE:
<223> OTHER INFORMATION: Magainin frog

<400> SEQUENCE: 123

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 124
<211> LENGTH: 25
<212> TYPE: PRT
<213> ORGANISM: unknown
<220> FEATURE:
<223> OTHER INFORMATION: Pleurocidin fish

<400> SEQUENCE: 124

```
Gly Trp Gly Ser Phe Phe Lys Ala Ala His Val Gly Lys His Val
1               5                   10                  15

Gly Lys Ala Ala Leu Thr His Tyr Leu
            20                  25

<210> SEQ ID NO 125
<211> LENGTH: 36
<212> TYPE: PRT
<213> ORGANISM: Aedes aegypti

<400> SEQUENCE: 125

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
            35

<210> SEQ ID NO 126
<211> LENGTH: 40
<212> TYPE: PRT
<213> ORGANISM: Drosophila melanogaster

<400> SEQUENCE: 126

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
            35                  40

<210> SEQ ID NO 127
<211> LENGTH: 21
<212> TYPE: PRT
<213> ORGANISM: unknown
<220> FEATURE:
<223> OTHER INFORMATION: Buforin II vertebrate

<400> SEQUENCE: 127

Thr Arg Ser Ser Arg Ala Gly Leu Gln Phe Pro Val Gly Arg Val His
1               5                   10                  15

Arg Leu Leu Arg Lys
            20

<210> SEQ ID NO 128
<211> LENGTH: 39
<212> TYPE: PRT
<213> ORGANISM: unknown
<220> FEATURE:
<223> OTHER INFORMATION: Sarcotoxin IA Fly

<400> SEQUENCE: 128

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
            35

<210> SEQ ID NO 129
<211> LENGTH: 17
<212> TYPE: PRT
```

<213> ORGANISM: Apis mellifera

<400> SEQUENCE: 129

Ala Asn Arg Pro Val Tyr Ile Pro Pro Pro Arg Pro Pro His Pro Arg
1               5                   10                  15

Leu

<210> SEQ ID NO 130
<211> LENGTH: 24
<212> TYPE: PRT
<213> ORGANISM: unknown
<220> FEATURE:
<223> OTHER INFORMATION: Ascaphine 5 Frog

<400> SEQUENCE: 130

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 131
<211> LENGTH: 22
<212> TYPE: PRT
<213> ORGANISM: unknown
<220> FEATURE:
<223> OTHER INFORMATION: Nigrocine 2 Frog

<400> SEQUENCE: 131

Gly Leu Leu Ser Lys Val Leu Gly Val Gly Lys Lys Val Leu Cys Gly
1               5                   10                  15

Val Ser Gly Leu Val Cys
            20

<210> SEQ ID NO 132
<211> LENGTH: 24
<212> TYPE: PRT
<213> ORGANISM: unknown
<220> FEATURE:
<223> OTHER INFORMATION: Pseudin 1 Rana Frog

<400> SEQUENCE: 132

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 133
<211> LENGTH: 18
<212> TYPE: PRT
<213> ORGANISM: unknown
<220> FEATURE:
<223> OTHER INFORMATION: Ranalexin Frog

<400> SEQUENCE: 133

Phe Leu Gly Gly Leu Ile Val Pro Ala Met Ile Cys Ala Val Thr Lys
1               5                   10                  15

Lys Cys

<210> SEQ ID NO 134
<211> LENGTH: 26
<212> TYPE: PRT
<213> ORGANISM: unknown
<220> FEATURE:
<223> OTHER INFORMATION: Melittin bee

<400> SEQUENCE: 134

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 135
<211> LENGTH: 25
<212> TYPE: PRT
<213> ORGANISM: unknown
<220> FEATURE:
<223> OTHER INFORMATION: Lycotoxin 1 Spider

<400> SEQUENCE: 135

Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25

<210> SEQ ID NO 136
<211> LENGTH: 19
<212> TYPE: PRT
<213> ORGANISM: unknown
<220> FEATURE:
<223> OTHER INFORMATION: Parasin 1 Fish

<400> SEQUENCE: 136

Lys Gly Arg Gly Lys Gln Gly Gly Lys Val Arg Ala Lys Ala Lys Thr
1               5                   10                  15

Arg Ser Ser

<210> SEQ ID NO 137
<211> LENGTH: 39
<212> TYPE: PRT
<213> ORGANISM: unknown
<220> FEATURE:
<223> OTHER INFORMATION: Buforin I Toad

<400> SEQUENCE: 137

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 138
<211> LENGTH: 34
<212> TYPE: PRT
<213> ORGANISM: unknown
<220> FEATURE:
<223> OTHER INFORMATION: Dermaseptin 1 Frog

<400> SEQUENCE: 138

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 139

```
<211> LENGTH: 12
<212> TYPE: PRT
<213> ORGANISM: unknown
<220> FEATURE:
<223> OTHER INFORMATION: Bactenecin 1 Cow

<400> SEQUENCE: 139

Arg Leu Cys Arg Ile Val Val Ile Arg Val Cys Arg
1               5                   10

<210> SEQ ID NO 140
<211> LENGTH: 21
<212> TYPE: PRT
<213> ORGANISM: unknown
<220> FEATURE:
<223> OTHER INFORMATION: Thanatin Insect

<400> SEQUENCE: 140

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 141
<211> LENGTH: 19
<212> TYPE: PRT
<213> ORGANISM: unknown
<220> FEATURE:
<223> OTHER INFORMATION: Brevinin 1T Rana frogs

<400> SEQUENCE: 141

Val Asn Pro Ile Ile Leu Gly Val Leu Pro Lys Val Cys Leu Ile Thr
1               5                   10                  15

Lys Lys Cys

<210> SEQ ID NO 142
<211> LENGTH: 26
<212> TYPE: PRT
<213> ORGANISM: unknown
<220> FEATURE:
<223> OTHER INFORMATION: Ranateurin 1 Rana frog

<400> SEQUENCE: 142

Ser Met Leu Ser Val Leu Lys Asn Leu Gly Lys Val Gly Leu Gly Phe
1               5                   10                  15

Val Ala Cys Lys Ile Asn Ile Lys Gln Cys
            20                  25

<210> SEQ ID NO 143
<211> LENGTH: 46
<212> TYPE: PRT
<213> ORGANISM: unknown
<220> FEATURE:
<223> OTHER INFORMATION: Esculentin 1 Rana frogs

<400> SEQUENCE: 143

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Lys Ile Ala Gly Cys Lys Ile Lys Gly Glu Cys
        35                  40                  45

<210> SEQ ID NO 144
```

```
<211> LENGTH: 17
<212> TYPE: PRT
<213> ORGANISM: Limulus polyphemus

<400> SEQUENCE: 144

Arg Trp Cys Phe Arg Val Cys Tyr Arg Gly Ile Cys Tyr Arg Lys Cys
1               5                   10                  15

Arg

<210> SEQ ID NO 145
<211> LENGTH: 25
<212> TYPE: PRT
<213> ORGANISM: unknown
<220> FEATURE:
<223> OTHER INFORMATION: Androctonin Scorpion

<400> SEQUENCE: 145

Arg Ser Val Cys Arg Gln Ile Lys Ile Cys Arg Arg Arg Gly Gly Cys
1               5                   10                  15

Tyr Tyr Lys Cys Thr Asn Arg Pro Tyr
            20                  25

<210> SEQ ID NO 146
<211> LENGTH: 30
<212> TYPE: PRT
<213> ORGANISM: Homo sapiens

<400> SEQUENCE: 146

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 147
<211> LENGTH: 38
<212> TYPE: PRT
<213> ORGANISM: unknown
<220> FEATURE:
<223> OTHER INFORMATION: beta-defensin cow

<400> SEQUENCE: 147

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35

<210> SEQ ID NO 148
<211> LENGTH: 18
<212> TYPE: PRT
<213> ORGANISM: unknown
<220> FEATURE:
<223> OTHER INFORMATION: theta-defensin monkey

<400> SEQUENCE: 148

Gly Phe Cys Arg Cys Leu Cys Arg Arg Gly Val Cys Arg Cys Ile Cys
1               5                   10                  15

Thr Arg

<210> SEQ ID NO 149
<211> LENGTH: 40
<212> TYPE: PRT
```

```
<213> ORGANISM: unknown
<220> FEATURE:
<223> OTHER INFORMATION: defensin (sapecin A) insect

<400> SEQUENCE: 149

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
        35                  40

<210> SEQ ID NO 150
<211> LENGTH: 46
<212> TYPE: PRT
<213> ORGANISM: unknown
<220> FEATURE:
<223> OTHER INFORMATION: Thionin (crambin) plant

<400> SEQUENCE: 150

Thr Thr Cys Cys Pro Ser Ile Val Ala Arg Ser Asn Phe Asn Val Cys
1               5                   10                  15

Arg Ile Pro Gly Thr Pro Glu Ala Ile Cys Ala Thr Tyr Thr Gly Cys
            20                  25                  30

Ile Ile Ile Pro Gly Ala Thr Cys Pro Gly Asp Tyr Ala Asn
            35                  40                  45

<210> SEQ ID NO 151
<211> LENGTH: 50
<212> TYPE: PRT
<213> ORGANISM: unknown
<220> FEATURE:
<223> OTHER INFORMATION: defensin from radish

<400> SEQUENCE: 151

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Cys Ile Cys Tyr Phe
            35                  40                  45

Pro Cys
    50

<210> SEQ ID NO 152
<211> LENGTH: 44
<212> TYPE: PRT
<213> ORGANISM: Drosophila melanogaster

<400> SEQUENCE: 152

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
            20                  25                  30

Cys Ser Pro Ser Leu Lys Cys Trp Cys Glu Gly Cys
            35                  40

<210> SEQ ID NO 153
<211> LENGTH: 25
<212> TYPE: PRT
<213> ORGANISM: Homo sapiens
```

<400> SEQUENCE: 153

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 154
<211> LENGTH: 44
<212> TYPE: PRT
<213> ORGANISM: unknown
<220> FEATURE:
<223> OTHER INFORMATION: Bac 5 Cow

<400> SEQUENCE: 154

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
                20                  25                  30

Pro Pro Phe Arg Pro Pro Leu Gly Arg Pro Phe Pro
            35                  40

<210> SEQ ID NO 155
<211> LENGTH: 39
<212> TYPE: PRT
<213> ORGANISM: unknown
<220> FEATURE:
<223> OTHER INFORMATION: PR-39 Pig

<400> SEQUENCE: 155

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
                20                  25                  30

Arg Phe Pro Pro Arg Phe Pro
            35

<210> SEQ ID NO 156
<211> LENGTH: 20
<212> TYPE: PRT
<213> ORGANISM: unknown
<220> FEATURE:
<223> OTHER INFORMATION: Pyrrhocoricin Insect

<400> SEQUENCE: 156

Val Asp Lys Gly Ser Tyr Leu Pro Arg Pro Thr Pro Pro Arg Pro Ile
1               5                   10                  15

Tyr Asn Arg Asn
            20

<210> SEQ ID NO 157
<211> LENGTH: 24
<212> TYPE: PRT
<213> ORGANISM: Homo sapiens

<400> SEQUENCE: 157

Asp Ser His Ala Lys Arg His His Gly Tyr Lys Arg Lys Phe His Glu
1               5                   10                  15

Lys His His Ser His Arg Gly Tyr
            20

<210> SEQ ID NO 158
<211> LENGTH: 19

```
<212> TYPE: PRT
<213> ORGANISM: Unknown
<220> FEATURE:
<223> OTHER INFORMATION: ECP19

<400> SEQUENCE: 158

Arg Pro Pro Gln Phe Thr Arg Ala Gln Trp Phe Ala Ile Gln His Ile
1               5                   10                  15

Ser Leu Asn

<210> SEQ ID NO 159
<211> LENGTH: 23
<212> TYPE: PRT
<213> ORGANISM: Unknown
<220> FEATURE:
<223> OTHER INFORMATION: MSI-594

<400> SEQUENCE: 159

Gly Ile Gly Lys Phe Leu Lys Lys Ala Lys Lys Gly Ile Gly Ala Val
1               5                   10                  15

Leu Lys Val Leu Thr Thr Gly
            20

<210> SEQ ID NO 160
<211> LENGTH: 35
<212> TYPE: PRT
<213> ORGANISM: Unknown
<220> FEATURE:
<223> OTHER INFORMATION: TL-ColM

<400> SEQUENCE: 160

Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro
        35

<210> SEQ ID NO 161
<211> LENGTH: 18
<212> TYPE: PRT
<213> ORGANISM: Unknown
<220> FEATURE:
<223> OTHER INFORMATION: SBO

<400> SEQUENCE: 161

Lys Leu Lys Lys Ile Ala Gln Lys Ile Lys Asn Phe Phe Ala Lys Leu
1               5                   10                  15

Val Ala

<210> SEQ ID NO 162
<211> LENGTH: 34
<212> TYPE: PRT
<213> ORGANISM: Limulus polyphemus

<400> SEQUENCE: 162

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser
```

```
<210> SEQ ID NO 163
<211> LENGTH: 18
<212> TYPE: PRT
<213> ORGANISM: artificial
<220> FEATURE:
<223> OTHER INFORMATION: synthetic sequence

<400> SEQUENCE: 163

Gly Phe Phe Ile Pro Ala Val Ile Leu Pro Ser Ile Ala Phe Leu Ile
1               5                   10                  15

Val Pro

<210> SEQ ID NO 164
<211> LENGTH: 5
<212> TYPE: PRT
<213> ORGANISM: artificial
<220> FEATURE:
<223> OTHER INFORMATION: synthetic sequence

<400> SEQUENCE: 164

Phe Phe Val Ala Pro
1               5

<210> SEQ ID NO 165
<211> LENGTH: 13
<212> TYPE: PRT
<213> ORGANISM: unknown
<220> FEATURE:
<223> OTHER INFORMATION: alpha4-helix of T4 lysozyme

<400> SEQUENCE: 165

Pro Asn Arg Ala Lys Arg Val Ile Thr Thr Phe Arg Thr
1               5                   10

<210> SEQ ID NO 166
<211> LENGTH: 27
<212> TYPE: PRT
<213> ORGANISM: artificial
<220> FEATURE:
<223> OTHER INFORMATION: synthetic sequence

<400> SEQUENCE: 166

Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 167
<211> LENGTH: 25
<212> TYPE: PRT
<213> ORGANISM: artificial
<220> FEATURE:
<223> OTHER INFORMATION: synthetic sequence

<400> SEQUENCE: 167

Gly Lys Pro Gly Trp Leu Ile Lys Val Ala Leu Lys Phe Lys Lys Leu
1               5                   10                  15

Ile Arg Arg Pro Leu Lys Arg Leu Ala
            20                  25

<210> SEQ ID NO 168
<211> LENGTH: 4
<212> TYPE: PRT
<213> ORGANISM: artificial
<220> FEATURE:
<223> OTHER INFORMATION: linker
```

<400> SEQUENCE: 168

Gly Ala Gly Ala
1

<210> SEQ ID NO 169
<211> LENGTH: 8
<212> TYPE: PRT
<213> ORGANISM: artificial
<220> FEATURE:
<223> OTHER INFORMATION: linker

<400> SEQUENCE: 169

Gly Ala Gly Ala Gly Ala Gly Ala
1               5

<210> SEQ ID NO 170
<211> LENGTH: 12
<212> TYPE: PRT
<213> ORGANISM: artificial
<220> FEATURE:
<223> OTHER INFORMATION: linker

<400> SEQUENCE: 170

Gly Ala Gly Ala Gly Ala Gly Ala Gly Ala Gly Ala
1               5                   10

<210> SEQ ID NO 171
<211> LENGTH: 252
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 171
atcctctatg aacgtcacat catggctagg ctactcaagg ctaagggtgt gcccattgcg      60
ggcctcccaa gcgatctggt gaacaccacg ccgggggggtt atggtaaatt ctcggagcaa    120
catggaaagc tggacagagc tgtgaagatt gacagggaat gtgctttgca gtcttgttct    180
tgggggatgt tccagctgat gggattcaac tataagttgt gtgggtacgc cacagttcaa    240
gcatttgtaa at                                                         252

<210> SEQ ID NO 172
<211> LENGTH: 255
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 172
atcctctatg aacgtcacat catggctagg ctactcaagg ctaagggtgt gcccattgcg      60
ggcctcccaa gcgatctggt gaacaccacg ccgggggggtt atggtaaatt ctcggagcaa    120
catggaaagc tggacagagc tgtgaagatt gacagggaat gtgctttgca gtcttgttct    180
tgggggatgt tccagctgat gggattcaac tataagttgt gtgggtacgc cacagttcaa    240
gcatttgtaa attaa                                                      255

<210> SEQ ID NO 173
<211> LENGTH: 255
<212> TYPE: DNA
<213> ORGANISM: Artificial Sequence

```
<220> FEATURE:
<223> OTHER INFORMATION: nucleic acid encoding peptidoglycan degrading
      enzyme

<400> SEQUENCE: 173
atgatcctct atgaacgtca catcatggct aggctactca aggctaaggg tgtgcccatt      60
gcgggcctcc caagcgatct ggtgaacacc acgccggggg gttatggtaa attctcggag     120
caacatggaa agctggacag agctgtgaag attgacaggg aatgtgcttt gcagtcttgt     180
tcttggggga tgttccagct gatgggattc aactataagt tgtgtgggta cgccacagtt     240
caagcatttg taaat                                                      255

<210> SEQ ID NO 174
<211> LENGTH: 258
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 174
atgatcctct atgaacgtca catcatggct aggctactca aggctaaggg tgtgcccatt      60
gcgggcctcc caagcgatct ggtgaacacc acgccggggg gttatggtaa attctcggag     120
caacatggaa agctggacag agctgtgaag attgacaggg aatgtgcttt gcagtcttgt     180
tcttggggga tgttccagct gatgggattc aactataagt tgtgtgggta cgccacagtt     240
caagcatttg taaattaa                                                   258

<210> SEQ ID NO 175
<211> LENGTH: 513
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 175
tgcgaagtgg cagctatcaa ggcaattgcc tctgtcgaga ctaagggcag tgcatggatc      60 accccggag tccccagat cctctatgaa cgtcacatca tggctaggct actcaaggct      120
aagggtgtgc ccattgcggg cctcccaagc gatctggtga acaccacgcc ggggggttat     180
ggtaaattct cggagcaaca tggaaagctg gacagagctg tgaagattga cagggaatgt     240
gctttgcagt cttgttcttg ggggatgttc cagctgatgg gattcaacta taagttgtgt     300
gggtacgcca cagttcaagc atttgtaaat gctatgtaca aaagtgaaga cgaacagtta     360
aatgcttttg taggtttcat taagagtaat ctacaactta atgatgcatt gaaatctaaa     420
gactgggcaa ctgttgccag actttacaat ggtgctgatt ataagataaa cagctacgac     480
cagaagctgg cagtggctta cgaatccaac aag                                  513

<210> SEQ ID NO 176
<211> LENGTH: 516
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 176
tgcgaagtgg cagctatcaa ggcaattgcc tctgtcgaga ctaagggcag tgcatggatc      60
```

```
acccccggag tcccccagat cctctatgaa cgtcacatca tggctaggct actcaaggct    120
aagggtgtgc ccattgcggg cctcccaagc gatctggtga acaccacgcc ggggggttat    180
ggtaaattct cggagcaaca tggaaagctg acagagctg tgaagattga cagggaatgt     240
gctttgcagt cttgttcttg ggggatgttc cagctgatgg gattcaacta taagttgtgt    300
gggtacgcca cagttcaagc atttgtaaat gctatgtaca aaagtgaaga cgaacagtta    360
aatgcttttg taggtttcat taagagtaat ctacaactta atgatgcatt gaaatctaaa    420
gactgggcaa ctgttgccag actttacaat ggtgctgatt ataagataaa cagctacgac    480
cagaagctgg cagtggctta cgaatccaac aagtaa                              516
```

<210> SEQ ID NO 177
<211> LENGTH: 516
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 177

```
atgtgcgaag tggcagctat caaggcaatt gcctctgtcg agactaaggg cagtgcatgg     60 atcaccccg gagtccccca gatcctctat gaacgtcaca tcatggctag ctactcaag    120 gctaagggtg tgcccattgc gggcctccca agcgatctgg tgaacaccac gccgggggt    180 tatggtaaat tctcggagca acatggaaag ctggacagag ctgtgaagat tgacagggaa    240
tgtgctttgc agtcttgttc ttgggggatg ttccagctga tgggattcaa ctataagttg    300
tgtgggtacg ccacagttca agcatttgta atgctatgt acaaaagtga agacgaacag    360
ttaaatgctt ttgtaggttt cattaagagt aatctacaac ttaatgatgc attgaaatct    420
aaagactggg caactgttgc cagactttac aatggtgctg attataagat aaacagctac    480
gaccagaagc tggcagtggc ttacgaatcc aacaag                              516
```

<210> SEQ ID NO 178
<211> LENGTH: 519
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 178

```
atgtgcgaag tggcagctat caaggcaatt gcctctgtcg agactaaggg cagtgcatgg     60 atcaccccg gagtccccca gatcctctat gaacgtcaca tcatggctag ctactcaag    120 gctaagggtg tgcccattgc gggcctccca agcgatctgg tgaacaccac gccgggggt    180 tatggtaaat tctcggagca acatggaaag ctggacagag ctgtgaagat tgacagggaa    240
tgtgctttgc agtcttgttc ttgggggatg ttccagctga tgggattcaa ctataagttg    300
tgtgggtacg ccacagttca agcatttgta atgctatgt acaaaagtga agacgaacag    360
ttaaatgctt ttgtaggttt cattaagagt aatctacaac ttaatgatgc attgaaatct    420
aaagactggg caactgttgc cagactttac aatggtgctg attataagat aaacagctac    480
gaccagaagc tggcagtggc ttacgaatcc aacaagtaa                           519
```

<210> SEQ ID NO 179
<211> LENGTH: 552
<212> TYPE: DNA
<213> ORGANISM: Artificial Sequence

```
<220> FEATURE:
<223> OTHER INFORMATION: nucleic acid encoding peptidoglycan degrading
      enzyme

<400> SEQUENCE: 179
gaaaaatctt tgtggaggc agctgctagt cttggctgcg aagtggcagc tatcaaggca      60
attgcctctg tcgagactaa gggcagtgca tggatcaccc ccggagtccc ccagatcctc    120
tatgaacgtc acatcatggc taggctactc aaggctaagg gtgtgcccat tgcgggcctc    180
ccaagcgatc tggtgaacac cacgccgggg ggttatggta aattctcgga gcaacatgga    240
aagctggaca gagctgtgaa gattgacagg gaatgtgctt tgcagtcttg ttcttggggg    300
atgttccagc tgatgggatt caactataag ttgtgtgggt acgccacagt tcaagcattt    360
gtaaatgcta tgtacaaaag tgaagacgaa cagttaaatg cttttgtagg tttcattaag    420
agtaatctac aacttaatga tgcattgaaa tctaaagact gggcaactgt tgccagactt    480
tacaatggtg ctgattataa gataaacagc tacgaccaga agctggcagt ggcttacgaa    540
tccaacaagc ga                                                        552

<210> SEQ ID NO 180
<211> LENGTH: 555
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 180
gaaaaatctt tgtggaggc agctgctagt cttggctgcg aagtggcagc tatcaaggca      60
attgcctctg tcgagactaa gggcagtgca tggatcaccc ccggagtccc ccagatcctc    120
tatgaacgtc acatcatggc taggctactc aaggctaagg gtgtgcccat tgcgggcctc    180
ccaagcgatc tggtgaacac cacgccgggg ggttatggta aattctcgga gcaacatgga    240
aagctggaca gagctgtgaa gattgacagg gaatgtgctt tgcagtcttg ttcttggggg    300
atgttccagc tgatgggatt caactataag ttgtgtgggt acgccacagt tcaagcattt    360
gtaaatgcta tgtacaaaag tgaagacgaa cagttaaatg cttttgtagg tttcattaag    420
agtaatctac aacttaatga tgcattgaaa tctaaagact gggcaactgt tgccagactt    480
tacaatggtg ctgattataa gataaacagc tacgaccaga agctggcagt ggcttacgaa    540
tccaacaagc gataa                                                    555

<210> SEQ ID NO 181
<211> LENGTH: 555
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 181
atggaaaaat cttttgtgga ggcagctgct agtcttggct gcgaagtggc agctatcaag     60
gcaattgcct ctgtcgagac taagggcagt gcatggatca ccccggagt cccccagatc    120 ctctatgaac gtcacatcat ggctaggcta ctcaaggcta agggtgtgcc cattgcgggc    180
ctcccaagcg atctggtgaa caccacgccg ggggttatg gtaaattctc ggagcaacat    240
ggaaagctgg acagagctgt gaagattgac agggaatgtc tttgcagtc ttgttcttgg    300 gggatgttcc agctgatggg attcaactat aagttgtgtg gtacgccac agttcaagca    360
```

```
tttgtaaatg ctatgtacaa aagtgaagac gaacagttaa atgcttttgt aggtttcatt    420
aagagtaatc tacaacttaa tgatgcattg aaatctaaag actgggcaac tgttgccaga    480
ctttacaatg gtgctgatta taagataaac agctacgacc agaagctggc agtggcttac    540
gaatccaaca agcga                                                    555
```

<210> SEQ ID NO 182
<211> LENGTH: 558
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 182

```
atggaaaaat cttttgtgga ggcagctgct agtcttggct gcgaagtggc agctatcaag     60
gcaattgcct ctgtcgagac taagggcagt gcatggatca ccccggagt ccccagatc     120 ctctatgaac gtcacatcat ggctaggcta ctcaaggcta agggtgtgcc cattgcgggc    180
ctcccaagcg atctggtgaa caccacgccg gggggttatg gtaaattctc ggagcaacat    240
ggaaagctgg acagagctgt gaagattgac agggaatgtg ctttgcagtc ttgttcttgg    300
gggatgttcc agctgatggg attcaactat aagttgtgtg gtacgccac agttcaagca    360 tttgtaaatg ctatgtacaa aagtgaagac gaacagttaa atgcttttgt aggtttcatt    420
aagagtaatc tacaacttaa tgatgcattg aaatctaaag actgggcaac tgttgccaga    480
ctttacaatg gtgctgatta taagataaac agctacgacc agaagctggc agtggcttac    540
gaatccaaca agcgataa                                                 558
```

<210> SEQ ID NO 183
<211> LENGTH: 495
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 183

```
ttaagtgaaa aatcttttgt ggaggcagct gctagtcttg gctgcgaagt ggcagctatc     60
aaggcaattg cctctgtcga gactaagggc agtgcatgga tcaccccggg agtccccag    120 atcctctatg aacgtcacat catggctagg ctactcaagg ctaagggtgt gcccattgcg    180
ggcctcccaa gcgatctggt gaacaccacg ccggggggtt atggtaaatt ctcggagcaa    240
catggaaagc tggacagagc tgtgaagatt gacagggaat gtctttgca gtcttgttct    300 tggggatgt tccagctgat gggattcaac tataagttgt gtgggtacgc cacagttcaa    360
gcatttgtaa atgctatgta caaaagtgaa gacgaacagt taaatgcttt tgtaggtttc    420
attaagagta atctacaact taatgatgca ttgaaatcta aagactgggc aactgttgcc    480
agactttaca atggt                                                    495
```

<210> SEQ ID NO 184
<211> LENGTH: 498
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 184

```
ttaagtgaaa aatcttttgt ggaggcagct gctagtcttg gctgcgaagt ggcagctatc        60
aaggcaattg cctctgtcga gactaagggc agtgcatgga tcaccccgg agtcccccag        120 atcctctatg aacgtcacat catggctagg ctactcaagg ctaagggtgt gcccattgcg       180
ggcctcccaa gcgatctggt gaacaccacg ccgggggggtt atggtaaatt ctcggagcaa      240
catggaaagc tggacagagc tgtgaagatt gacagggaat gtgctttgca gtcttgttct      300
tgggggatgt tccagctgat gggattcaac tataagttgt gtgggtacgc cacagttcaa     360
gcatttgtaa atgctatgta caaaagtgaa gacgaacagt taaatgcttt tgtaggtttc    420
attaagagta atctacaact taatgatgca ttgaaatcta agactgggc aactgttgcc      480 agactttaca atggttaa                                                 498

<210> SEQ ID NO 185
<211> LENGTH: 498
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 185
atgttaagtg aaaaatcttt tgtggaggca gctgctagtc ttggctgcga agtggcagct       60
atcaaggcaa ttgcctctgt cgagactaag ggcagtgcat ggatcacccc cggagtcccc      120
cagatcctct atgaacgtca catcatggct aggctactca aggctaaggg tgtgcccatt       180
gcgggcctcc caagcgatct ggtgaacacc acgccggggg gttatggtaa attctcggag       240
caacatggaa agctggacag agctgtgaag attgacaggg aatgtgcttt gcagtcttgt      300
tcttggggga tgttccagct gatgggattc aactataagt tgtgtgggta cgccacagtt       360
caagcatttg taaatgctat gtacaaaagt gaagacgaac agttaaatgc ttttgtaggt     420
ttcattaaga gtaatctaca acttaatgat gcattgaaat ctaaagactg gcaactgtt      480 gccagacttt acaatggt                                                 498

<210> SEQ ID NO 186
<211> LENGTH: 501
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 186
atgttaagtg aaaaatcttt tgtggaggca gctgctagtc ttggctgcga agtggcagct       60
atcaaggcaa ttgcctctgt cgagactaag ggcagtgcat ggatcacccc cggagtcccc      120
cagatcctct atgaacgtca catcatggct aggctactca aggctaaggg tgtgcccatt       180
gcgggcctcc caagcgatct ggtgaacacc acgccggggg gttatggtaa attctcggag       240
caacatggaa agctggacag agctgtgaag attgacaggg aatgtgcttt gcagtcttgt      300
tcttggggga tgttccagct gatgggattc aactataagt tgtgtgggta cgccacagtt       360
caagcatttg taaatgctat gtacaaaagt gaagacgaac agttaaatgc ttttgtaggt     420
ttcattaaga gtaatctaca acttaatgat gcattgaaat ctaaagactg gcaactgtt      480 gccagacttt acaatggtta a                                             501

<210> SEQ ID NO 187
```

```
<211> LENGTH: 528
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 187
ttaagtgaaa aatcttttgt ggaggcagct gctagtcttg gctgcgaagt ggcagctatc      60
aaggcaattg cctctgtcga gactaagggc agtgcatgga tcaccccgg agtcccccag     120 atcctctatg aacgtcacat catggctagg ctactcaagg ctaagggtgt gcccattgcg    180
ggcctcccaa gcgatctggt gaacaccacg ccggggggtt atggtaaatt ctcggagcaa    240
catggaaagc tggacagagc tgtgaagatt gacagggaat gtgctttgca gtcttgttct    300
tgggggatgt tccagctgat gggattcaac tataagttgt gtgggtacgc cacagttcaa    360
gcatttgtaa atgctatgta caaaagtgaa gacgaacagt taaatgcttt tgtaggtttc    420
attaagagta atctcacaact taatgatgca ttgaaatcta aagactgggc aactgttgcc    480
agactttaca atggtgctga ttataagata aacagctacg accagaag               528

<210> SEQ ID NO 188
<211> LENGTH: 531
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 188
ttaagtgaaa aatcttttgt ggaggcagct gctagtcttg gctgcgaagt ggcagctatc      60
aaggcaattg cctctgtcga gactaagggc agtgcatgga tcaccccgg agtcccccag     120 atcctctatg aacgtcacat catggctagg ctactcaagg ctaagggtgt gcccattgcg    180
ggcctcccaa gcgatctggt gaacaccacg ccggggggtt atggtaaatt ctcggagcaa    240
catggaaagc tggacagagc tgtgaagatt gacagggaat gtgctttgca gtcttgttct    300
tgggggatgt tccagctgat gggattcaac tataagttgt gtgggtacgc cacagttcaa    360
gcatttgtaa atgctatgta caaaagtgaa gacgaacagt taaatgcttt tgtaggtttc    420
attaagagta atctcacaact taatgatgca ttgaaatcta aagactgggc aactgttgcc    480
agactttaca atggtgctga ttataagata aacagctacg accagaagta a            531

<210> SEQ ID NO 189
<211> LENGTH: 531
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 189
atgttaagtg aaaaatcttt tgtggaggca gctgctagtc ttggctgcga agtggcagct      60
atcaaggcaa ttgcctctgt cgagactaag ggcagtgcat ggatcacccc cggagtcccc    120
cagatcctct atgaacgtca catcatggct aggctactca aggctaaggg tgtgcccatt    180
gcgggcctcc caagcgatct ggtgaacacc acgccggggg gttatggtaa attctcggag    240
caacatggaa agctggacag agctgtgaag attgacaggg aatgtgcttt gcagtcttgt    300
tcttggggga tgttccagct gatgggattc aactataagt tgtgtgggta cgccacagtt    360
```

```
caagcatttg taaatgctat gtacaaaagt gaagacgaac agttaaatgc ttttgtaggt    420
ttcattaaga gtaatctaca acttaatgat gcattgaaat ctaaagactg ggcaactgtt    480
gccagacttt acaatggtgc tgattataag ataaacagct acgaccagaa g             531
```

<210> SEQ ID NO 190
<211> LENGTH: 534
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 190

```
atgttaagtg aaaaatcttt tgtggaggca gctgctagtc ttggctgcga agtggcagct     60
atcaaggcaa ttgcctctgt cgagactaag ggcagtgcat ggatcacccc cggagtcccc    120
cagatcctct atgaacgtca catcatggct aggctactca aggctaaggg tgtgcccatt    180
gcgggcctcc caagcgatct ggtgaacacc acgccggggg ttatggtaa attctcggag     240 caacatggaa agctggacag agctgtgaag attgacaggg aatgtgcttt gcagtcttgt    300
tcttggggga tgttccagct gatgggattc aactataagt tgtgtgggta cgccacagtt    360
caagcatttg taaatgctat gtacaaaagt gaagacgaac agttaaatgc ttttgtaggt    420
ttcattaaga gtaatctaca acttaatgat gcattgaaat ctaaagactg ggcaactgtt    480
gccagacttt acaatggtgc tgattataag ataaacagct acgaccagaa gtaa          534
```

<210> SEQ ID NO 191
<211> LENGTH: 543
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 191

```
ttaagtgaaa atcttttgt ggaggcagct gctagtcttg gctgcgaagt ggcagctatc      60
aaggcaattg cctctgtcga gactaagggc agtgcatgga tccccccgg agtccccccag    120 atcctctatg aacgtcacat catggctagg ctactcaagg ctaagggtgt gcccattgcg    180
ggcctcccaa gcgatctggt gaacaccacg ccggggggtt atggtaaatt ctcggagcaa    240
catggaaagc tggacagagc tgtgaagatt gacagggaat gtgctttgca gtcttgttct    300 gggggatgt tccagctgat gggattcaac tataagttgt gtgggtacgc cacagttcaa     360
gcatttgtaa atgctatgta caaaagtgaa gacgaacagt taaatgcttt gtaggtttc     420 attaagagta atctacaact taatgatgca ttgaaatcta aagactgggc aactgttgcc    480
agactttaca atggtgctga ttataagata aacagctacg accagaagct ggcagtggct    540
tac                                                                  543
```

<210> SEQ ID NO 192
<211> LENGTH: 546
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 192

```
ttaagtgaaa atcttttgt ggaggcagct gctagtcttg gctgcgaagt ggcagctatc      60
```

```
aaggcaattg cctctgtcga gactaagggc agtgcatgga tcaccccgg  agtccccag    120 atcctctatg aacgtcacat catggctagg ctactcaagg ctaagggtgt gcccattgcg    180
ggcctcccaa gcgatctggt gaacaccacg ccgggggtt  atggtaaatt ctcggagcaa    240 catgaaagc  tggacagagc tgtgaagatt gacagggaat gtgctttgca gtcttgttct    300
tgggggatgt tccagctgat gggattcaac tataagttgt gtgggtacgc cacagttcaa    360
gcatttgtaa atgctatgta caaaagtgaa gacgaacagt taaatgcttt tgtaggtttc    420
attaagagta atctacaact taatgatgca ttgaaatcta aagactgggc aactgttgcc    480
agactttaca atggtgctga ttataagata aacagctacg accagaagct ggcagtggct    540
tactaa                                                               546

<210> SEQ ID NO 193
<211> LENGTH: 546
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 193
atgttaagtg aaaaatcttt tgtggaggca gctgctagtc ttggctgcga agtggcagct     60
atcaaggcaa ttgcctctgt cgagactaag ggcagtgcat ggatcacccc cggagtcccc   120
cagatcctct atgaacgtca catcatggct aggctactca aggctaaggg tgtgcccatt   180
gcgggcctcc caagcgatct ggtgaacacc acgccggggg gttatggtaa attctcggag   240
caacatggaa agctggacag agctgtgaag attgacaggg aatgtgcttt gcagtcttgt   300
tcttggggga tgttccagct gatgggattc aactataagt tgtgtgggta cgccacagtt   360
caagcatttg taaatgctat gtacaaaagt gaagacgaac agttaaatgc ttttgtaggt   420
ttcattaaga gtaatctaca acttaatgat gcattgaaat ctaaagactg gcaactgtt   480 gccagacttt acaatggtgc tgattataag ataaacagct acgaccagaa gctggcagtg   540
gcttac                                                             546

<210> SEQ ID NO 194
<211> LENGTH: 549
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 194
atgttaagtg aaaaatcttt tgtggaggca gctgctagtc ttggctgcga agtggcagct     60
atcaaggcaa ttgcctctgt cgagactaag ggcagtgcat ggatcacccc cggagtcccc   120
cagatcctct atgaacgtca catcatggct aggctactca aggctaaggg tgtgcccatt   180
gcgggcctcc caagcgatct ggtgaacacc acgccggggg gttatggtaa attctcggag   240
caacatggaa agctggacag agctgtgaag attgacaggg aatgtgcttt gcagtcttgt   300
tcttggggga tgttccagct gatgggattc aactataagt tgtgtgggta cgccacagtt   360
caagcatttg taaatgctat gtacaaaagt gaagacgaac agttaaatgc ttttgtaggt   420
ttcattaaga gtaatctaca acttaatgat gcattgaaat ctaaagactg gcaactgtt   480 gccagacttt acaatggtgc tgattataag ataaacagct acgaccagaa gctggcagtg   540
gcttactaa                                                          549
```

```
<210> SEQ ID NO 195
<211> LENGTH: 501
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 195
atcaaggcaa ttgcctctgt cgagactaag ggcagtgcat ggatcacccc cggagtcccc      60
cagatcctct atgaacgtca catcatggct aggctactca aggctaaggg tgtgcccatt     120
gcgggcctcc caagcgatct ggtgaacacc acgccggggg gttatggtaa attctcggag     180
caacatggaa agctggacag agctgtgaag attgacaggg aatgtgcttt gcagtcttgt     240
tcttggggga tgttccagct gatgggattc aactataagt tgtgtgggta cgccacagtt     300
caagcatttg taaatgctat gtacaaaagt gaagacgaac agttaaatgc ttttgtaggt     360
ttcattaaga gtaatctaca acttaatgat gcattgaaat ctaaagactg gcaactgtt      420 gccagacttt acaatggtgc tgattataag ataaacagct acgaccagaa gctggcagtg     480
gcttacgaat ccaacaagcg a                                               501

<210> SEQ ID NO 196
<211> LENGTH: 504
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 196
atcaaggcaa ttgcctctgt cgagactaag ggcagtgcat ggatcacccc cggagtcccc      60
cagatcctct atgaacgtca catcatggct aggctactca aggctaaggg tgtgcccatt     120
gcgggcctcc caagcgatct ggtgaacacc acgccggggg gttatggtaa attctcggag     180
caacatggaa agctggacag agctgtgaag attgacaggg aatgtgcttt gcagtcttgt     240
tcttggggga tgttccagct gatgggattc aactataagt tgtgtgggta cgccacagtt     300
caagcatttg taaatgctat gtacaaaagt gaagacgaac agttaaatgc ttttgtaggt     360
ttcattaaga gtaatctaca acttaatgat gcattgaaat ctaaagactg gcaactgtt      420 gccagacttt acaatggtgc tgattataag ataaacagct acgaccagaa gctggcagtg     480
gcttacgaat ccaacaagcg ataa                                            504

<210> SEQ ID NO 197
<211> LENGTH: 504
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 197
atgatcaagg caattgcctc tgtcgagact aagggcagtg catggatcac ccccggagtc      60
ccccagatcc tctatgaacg tcacatcatg gctaggctac tcaaggctaa gggtgtgccc     120
attgcgggcc tcccaagcga tctggtgaac accacgccgg ggggttatgg taaattctcg     180
gagcaacatg gaaagctgga cagagctgtg aagattgaca gggaatgtgc tttgcagtct     240
tgttcttggg ggatgttcca gctgatggga ttcaactata gttgtgtgg gtacgccaca      300
```

```
gttcaagcat ttgtaaatgc tatgtacaaa agtgaagacg aacagttaaa tgcttttgta      360
ggtttcatta agagtaatct acaacttaat gatgcattga aatctaaaga ctgggcaact      420
gttgccagac tttacaatgg tgctgattat aagataaaca gctacgacca gaagctggca      480
gtggcttacg aatccaacaa gcga                                             504
```

<210> SEQ ID NO 198
<211> LENGTH: 507
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 198

```
atgatcaagg caattgcctc tgtcgagact aagggcagtg catggatcac ccccggagtc       60
ccccagatcc tctatgaacg tcacatcatg gctaggctac tcaaggctaa gggtgtgccc     120
attgcgggcc tcccaagcga tctggtgaac accacgccgg ggggttatgg taaattctcg     180
gagcaacatg gaaagctgga cagagctgtg aagattgaca gggaatgtgc tttgcagtct     240
tgttcttggg ggatgttcca gctgatggga ttcaactata gttgtgtgg gtacgccaca     300 gttcaagcat ttgtaaatgc tatgtacaaa agtgaagacg aacagttaaa tgcttttgta      360
ggtttcatta agagtaatct acaacttaat gatgcattga aatctaaaga ctgggcaact      420
gttgccagac tttacaatgg tgctgattat aagataaaca gctacgacca gaagctggca      480
gtggcttacg aatccaacaa gcgataa                                          507
```

<210> SEQ ID NO 199
<211> LENGTH: 534
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 199

```
gcagctgcta gtcttggctg cgaagtggca gctatcaagg caattgcctc tgtcgagact       60
aagggcagtg catggatcac ccccggagtc ccccagatcc tctatgaacg tcacatcatg     120
gctaggctac tcaaggctaa gggtgtgccc attgcgggcc tcccaagcga tctggtgaac     180
accacgccgg ggggttatgg taaattctcg gagcaacatg gaaagctgga cagagctgtg     240
aagattgaca gggaatgtgc tttgcagtct tgttcttggg ggatgttcca gctgatggga     300
ttcaactata gttgtgtgg gtacgccaca gttcaagcat ttgtaaatgc tatgtacaaa      360
agtgaagacg aacagttaaa tgcttttgta ggtttcatta agagtaatct acaacttaat      420
gatgcattga aatctaaaga ctgggcaact gttgccagac tttacaatgg tgctgattat      480
aagataaaca gctacgacca gaagctggca gtggcttacg aatccaacaa gcga            534
```

<210> SEQ ID NO 200
<211> LENGTH: 537
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 200

```
gcagctgcta gtcttggctg cgaagtggca gctatcaagg caattgcctc tgtcgagact       60
```

```
aagggcagtg catggatcac ccccggagtc ccccagatcc tctatgaacg tcacatcatg    120
gctaggctac tcaaggctaa gggtgtgccc attgcgggcc tcccaagcga tctggtgaac    180
accacgccgg ggggttatgg taaattctcg gagcaacatg gaaagctgga cagagctgtg    240
aagattgaca gggaatgtgc tttgcagtct tgttcttggg ggatgttcca gctgatggga    300
ttcaactata agttgtgtgg gtacgccaca gttcaagcat ttgtaaatgc tatgtacaaa    360
agtgaagacg aacagttaaa tgcttttgta ggtttcatta agagtaatct acaacttaat    420
gatgcattga atctaaaga ctgggcaact gttgccagac tttacaatgg tgctgattat     480
aagataaaca gctacgacca gaagctggca gtggcttacg aatccaacaa gcgataa      537
```

<210> SEQ ID NO 201
<211> LENGTH: 537
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 201

```
atggcagctg ctagtcttgg ctgcgaagtg gcagctatca aggcaattgc ctctgtcgag    60
actaagggca gtcatggat caccccgga gtcccccaga tcctctatga acgtcacatc     120
atggctaggc tactcaaggc taagggtgtg cccattgcgg gcctcccaag cgatctggtg    180
aacaccacgc cggggggtta tgtaaaattc tcggagcaac atggaaagct ggacagagct    240
gtgaagattg acagggaatg tgctttgcag tcttgttctt gggggatgtt ccagctgatg    300
ggattcaact ataagttgtg tgggtacgcc acagttcaag catttgtaaa tgctatgtac    360
aaaagtgaag acgaacagtt aaatgctttt gtaggtttca ttaagagtaa tctacaactt    420
aatgatgcat tgaaatctaa agactgggca actgttgcca gactttacaa tggtgctgat    480
tataagataa acagctacga ccagaagctg gcagtggctt acgaatccaa caagcga     537
```

<210> SEQ ID NO 202
<211> LENGTH: 540
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 202

```
atggcagctg ctagtcttgg ctgcgaagtg gcagctatca aggcaattgc ctctgtcgag    60
actaagggca gtcatggat caccccgga gtcccccaga tcctctatga acgtcacatc     120
atggctaggc tactcaaggc taagggtgtg cccattgcgg gcctcccaag cgatctggtg    180
aacaccacgc cggggggtta tgtaaaattc tcggagcaac atggaaagct ggacagagct    240
gtgaagattg acagggaatg tgctttgcag tcttgttctt gggggatgtt ccagctgatg    300
ggattcaact ataagttgtg tgggtacgcc acagttcaag catttgtaaa tgctatgtac    360
aaaagtgaag acgaacagtt aaatgctttt gtaggtttca ttaagagtaa tctacaactt    420
aatgatgcat tgaaatctaa agactgggca actgttgcca gactttacaa tggtgctgat    480
tataagataa acagctacga ccagaagctg gcagtggctt acgaatccaa caagcgataa   540
```

<210> SEQ ID NO 203
<211> LENGTH: 549
<212> TYPE: DNA

<213> ORGANISM: Artificial Sequence
<220> FEATURE:
<223> OTHER INFORMATION: nucleic acid encoding peptidoglycan degrading enzyme

<400> SEQUENCE: 203

```
aaatcttttg tggaggcagc tgctagtctt ggctgcgaag tggcagctat caaggcaatt      60
gcctctgtcg agactaaggg cagtgcatgg atcaccccg gagtccccca gatcctctat     120
gaacgtcaca tcatggctag ctactcaag gctaagggtg tgcccattgc gggcctccca     180
agcgatctgg tgaacaccac gccgggggt tatggtaaat tctcggagca acatggaaag     240
ctggacagag ctgtgaagat tgacaggaa tgtgctttgc agtcttgttc ttggggatg      300
ttccagctga tgggattcaa ctataagttg tgtgggtacg ccacagttca agcatttgta   360
aatgctatgt acaaaagtga agacgaacag ttaaatgctt ttgtaggttt cattaagagt   420
aatctacaac ttaatgatgc attgaaatct aaagactggg caactgttgc cagactttac   480
aatggtgctg attataagat aaacagctac gaccagaagc tggcagtggc ttacgaatcc   540
aacaagcga                                                             549
```

<210> SEQ ID NO 204
<211> LENGTH: 552
<212> TYPE: DNA
<213> ORGANISM: Artificial Sequence
<220> FEATURE:
<223> OTHER INFORMATION: nucleic acid encoding peptidoglycan degrading enzyme

<400> SEQUENCE: 204

```
aaatcttttg tggaggcagc tgctagtctt ggctgcgaag tggcagctat caaggcaatt      60
gcctctgtcg agactaaggg cagtgcatgg atcaccccg gagtccccca gatcctctat     120
gaacgtcaca tcatggctag ctactcaag gctaagggtg tgcccattgc gggcctccca     180
agcgatctgg tgaacaccac gccgggggt tatggtaaat tctcggagca acatggaaag     240
ctggacagag ctgtgaagat tgacagggaa tgtgctttgc agtcttgttc ttggggatg      300
ttccagctga tgggattcaa ctataagttg tgtgggtacg ccacagttca agcatttgta   360
aatgctatgt acaaaagtga agacgaacag ttaaatgctt ttgtaggttt cattaagagt   420
aatctacaac ttaatgatgc attgaaatct aaagactggg caactgttgc cagactttac   480
aatggtgctg attataagat aaacagctac gaccagaagc tggcagtggc ttacgaatcc   540
aacaagcgat aa                                                        552
```

<210> SEQ ID NO 205
<211> LENGTH: 552
<212> TYPE: DNA
<213> ORGANISM: Artificial Sequence
<220> FEATURE:
<223> OTHER INFORMATION: nucleic acid encoding peptidoglycan degrading enzyme

<400> SEQUENCE: 205

```
atgaaatctt ttgtggaggc agctgctagt cttggctgcg aagtggcagc tatcaaggca      60
attgcctctg tcgagactaa gggcagtgca tggatcaccc ccggagtccc ccagatcctc   120
tatgaacgtc acatcatggc taggctactc aaggctaagg gtgtgcccat gcgggcctc    180
ccaagcgatc tggtgaacac cacgccgggg ggttatggta aattctcgga gcaacatgga   240
aagctggaca gagctgtgaa gattgacagg gaatgtgctt tgcagtcttg ttcttggggg   300
```

```
atgttccagc tgatgggatt caactataag ttgtgtgggt acgccacagt tcaagcattt    360
gtaaatgcta tgtacaaaag tgaagacgaa cagttaaatg cttttgtagg tttcattaag    420
agtaatctac aacttaatga tgcattgaaa tctaaagact gggcaactgt tgccagactt    480
tacaatggtg ctgattataa gataaacagc tacgaccaga agctggcagt ggcttacgaa    540
tccaacaagc ga                                                        552
```

<210> SEQ ID NO 206
<211> LENGTH: 555
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 206

```
atgaaatctt ttgtggaggc agctgctagt cttggctgcg aagtggcagc tatcaaggca     60
attgcctctg tcgagactaa gggcagtgca tggatcaccc ccggagtccc ccagatcctc    120
tatgaacgtc acatcatggc taggctactc aaggctaagg gtgtgcccat tgcgggcctc    180
ccaagcgatc tggtgaacac cacgccgggg ggttatggta aattctcgga gcaacatgga    240
aagctggaca gagctgtgaa gattgacagg gaatgtgctt tgcagtcttg ttcttggggg    300
atgttccagc tgatgggatt caactataag ttgtgtgggt acgccacagt tcaagcattt    360
gtaaatgcta tgtacaaaag tgaagacgaa cagttaaatg cttttgtagg tttcattaag    420
agtaatctac aacttaatga tgcattgaaa tctaaagact gggcaactgt tgccagactt    480
tacaatggtg ctgattataa gataaacagc tacgaccaga agctggcagt ggcttacgaa    540
tccaacaagc gataa                                                     555
```

<210> SEQ ID NO 207
<211> LENGTH: 558
<212> TYPE: DNA
<213> ORGANISM: Artificial Sequence
<220> FEATURE:
<223> OTHER INFORMATION: nucleic acid encoding peptidoglycan degrading
      enzyme

<400> SEQUENCE: 207

```
ttaagtgaaa atcttttgt ggaggcagct gctagtcttg ctgcgaagt ggcagctatc      60 aaggcaattg cctctgtcga gactaagggc agtgcatgga tcaccccgg agtcccccag    120 atcctctatg aacgtcacat catggctagg ctactcaagg ctaagggtgt gcccattgcg    180
ggcctcccaa gcgatctggt gaacaccacg ccgggggtt atggtaaatt ctcggagcaa    240
catggaaagc tggacagagc tgtgaagatt gacagggaat gtgctttgca gtcttgttct    300 tggggatgt tccagctgat gggattcaac tataagttgt gtgggtacgc cacagttcaa    360
gcatttgtaa atgctatgta caaaagtgaa gacgaacagt taaatgcttt tgtaggtttc    420
attaagagta atctacaact taatgatgca ttgaaatcta aagactgggc aactgttgcc    480
agactttaca atggtgctga ttataagata aacagctacg accagaagct ggcagtggct    540
tacgaatcca acaagcga                                                  558
```

<210> SEQ ID NO 208
<211> LENGTH: 561
<212> TYPE: DNA
<213> ORGANISM: Artificial Sequence
<220> FEATURE:
<223> OTHER INFORMATION: nucleic acid encoding peptidoglycan degrading enzyme

<400> SEQUENCE: 208

```
ttaagtgaaa aatctttttgt ggaggcagct gctagtcttg gctgcgaagt ggcagctatc    60
aaggcaattg cctctgtcga gactaagggc agtgcatgga tcaccccgg agtcccccag    120
atcctctatg aacgtcacat catggctagg ctactcaagg ctaagggtgt gcccattgcg    180
ggcctcccaa gcgatctggt gaacaccacg ccgggggtt atggtaaatt ctcggagcaa    240
catggaaagc tggacagagc tgtgaagatt gacagggaat gtgctttgca gtcttgttct    300
tgggggatgt tccagctgat gggattcaac tataagttgt gtgggtacgc cacagttcaa    360
gcatttgtaa atgctatgta caaaagtgaa gacgaacagt taaatgcttt tgtaggtttc    420
attaagagta atctacaact taatgatgca ttgaaatcta agactgggc aactgttgcc    480
agactttaca atggtgctga ttataagata aacagctacg accagaagct ggcagtggct    540
tacgaatcca acaagcgata a    561
```

<210> SEQ ID NO 209
<211> LENGTH: 561
<212> TYPE: DNA
<213> ORGANISM: Artificial Sequence
<220> FEATURE:
<223> OTHER INFORMATION: nucleic acid encoding peptidoglycan degrading enzyme

<400> SEQUENCE: 209

```
atgttaagtg aaaaatcttt tgtggaggca gctgctagtc ttggctgcga agtggcagct    60
atcaaggcaa ttgcctctgt cgagactaag ggcagtgcat ggatcacccc cggagtcccc    120
cagatcctct atgaacgtca catcatggct aggctactca aggctaaggg tgtgcccatt    180
gcgggcctcc caagcgatct ggtgaacacc acgccggggg gttatggtaa attctcggag    240
caacatggaa agctggacag agctgtgaag attgacaggg aatgtgcttt gcagtcttgt    300
tcttggggga tgttccagct gatgggattc aactataagt tgtgtgggta cgccacagtt    360
caagcatttg taaatgctat gtacaaaagt gaagacgaac agttaaatgc ttttgtaggt    420
ttcattaaga gtaatctaca acttaatgat gcattgaaat ctaaagactg gcaactgtt    480
gccagacttt acaatggtgc tgattataag ataaacagct acgaccagaa gctggcagtg    540
gcttacgaat ccaacaagcg a    561
```

<210> SEQ ID NO 210
<211> LENGTH: 564
<212> TYPE: DNA
<213> ORGANISM: Artificial Sequence
<220> FEATURE:
<223> OTHER INFORMATION: nucleic acid encoding peptidoglycan degrading enzyme

<400> SEQUENCE: 210

```
atgttaagtg aaaaatcttt tgtggaggca gctgctagtc ttggctgcga agtggcagct    60
atcaaggcaa ttgcctctgt cgagactaag ggcagtgcat ggatcacccc cggagtcccc    120
cagatcctct atgaacgtca catcatggct aggctactca aggctaaggg tgtgcccatt    180
gcgggcctcc caagcgatct ggtgaacacc acgccggggg gttatggtaa attctcggag    240
caacatggaa agctggacag agctgtgaag attgacaggg aatgtgcttt gcagtcttgt    300
tcttggggga tgttccagct gatgggattc aactataagt tgtgtgggta cgccacagtt    360
caagcatttg taaatgctat gtacaaaagt gaagacgaac agttaaatgc ttttgtaggt    420
```

```
ttcattaaga gtaatctaca acttaatgat gcattgaaat ctaaagactg ggcaactgtt    480
gccagacttt acaatggtgc tgattataag ataaacagct acgaccagaa gctggcagtg    540
gcttacgaat ccaacaagcg ataa                                            564
```

<210> SEQ ID NO 211
<211> LENGTH: 219
<212> TYPE: PRT
<213> ORGANISM: Artificial Sequence
<220> FEATURE:
<223> OTHER INFORMATION: Buforin II-SEQ ID NO:92

<400> SEQUENCE: 211

Met Thr Arg Ser Ser Arg Ala Gly Leu Gln Phe Pro Val Gly Arg Val
1               5                   10                  15

His Arg Leu Leu Arg Lys Gly Ser Met Leu Ser Glu Lys Ser Phe Val
            20                  25                  30

Glu Ala Ala Ala Ser Leu Gly Cys Glu Val Ala Ala Ile Lys Ala Ile
        35                  40                  45

Ala Ser Val Glu Thr Lys Gly Ser Ala Trp Ile Thr Pro Gly Val Pro
    50                  55                  60

Gln Ile Leu Tyr Glu Arg His Ile Met Ala Arg Leu Leu Lys Ala Lys
65                  70                  75                  80

Gly Val Pro Ile Ala Gly Leu Pro Ser Asp Leu Val Asn Thr Thr Pro
                85                  90                  95

Gly Gly Tyr Gly Lys Phe Ser Glu Gln His Gly Lys Leu Asp Arg Ala
            100                 105                 110

Val Lys Ile Asp Arg Glu Cys Ala Leu Gln Ser Cys Ser Trp Gly Met
        115                 120                 125

Phe Gln Leu Met Gly Phe Asn Tyr Lys Leu Cys Gly Tyr Ala Thr Val
    130                 135                 140

Gln Ala Phe Val Asn Ala Met Tyr Lys Ser Glu Asp Glu Gln Leu Asn
145                 150                 155                 160

Ala Phe Val Gly Phe Ile Lys Ser Asn Leu Gln Leu Asn Asp Ala Leu
                165                 170                 175

Lys Ser Lys Asp Trp Ala Thr Val Ala Arg Leu Tyr Asn Gly Ala Asp
            180                 185                 190

Tyr Lys Ile Asn Ser Tyr Asp Gln Lys Leu Ala Val Ala Tyr Glu Ser
        195                 200                 205

Asn Lys Arg Leu Glu His His His His His
    210                 215

<210> SEQ ID NO 212
<211> LENGTH: 227
<212> TYPE: PRT
<213> ORGANISM: Artificial Sequence
<220> FEATURE:
<223> OTHER INFORMATION: SMAP29-SEQ ID NO:92

<400> SEQUENCE: 212

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Met Leu Ser Glu Lys Ser Phe Val Glu Ala Ala Ala Ser Leu Gly Cys
        35                  40                  45

Glu Val Ala Ala Ile Lys Ala Ile Ala Ser Val Glu Thr Lys Gly Ser

```
                50             55              60
Ala Trp Ile Thr Pro Gly Val Pro Gln Ile Leu Tyr Glu Arg His Ile
 65                  70                  75                  80

Met Ala Arg Leu Leu Lys Ala Lys Gly Val Pro Ile Ala Gly Leu Pro
                     85                  90                  95

Ser Asp Leu Val Asn Thr Thr Pro Gly Gly Tyr Gly Lys Phe Ser Glu
                100                 105                 110

Gln His Gly Lys Leu Asp Arg Ala Val Lys Ile Asp Arg Glu Cys Ala
            115                 120                 125

Leu Gln Ser Cys Ser Trp Gly Met Phe Gln Leu Met Gly Phe Asn Tyr
        130                 135                 140

Lys Leu Cys Gly Tyr Ala Thr Val Gln Ala Phe Val Asn Ala Met Tyr
145                 150                 155                 160

Lys Ser Glu Asp Glu Gln Leu Asn Ala Phe Val Gly Phe Ile Lys Ser
                165                 170                 175

Asn Leu Gln Leu Asn Asp Ala Leu Lys Ser Lys Asp Trp Ala Thr Val
            180                 185                 190

Ala Arg Leu Tyr Asn Gly Ala Asp Tyr Lys Ile Asn Ser Tyr Asp Gln
        195                 200                 205

Lys Leu Ala Val Ala Tyr Glu Ser Asn Lys Arg Leu Glu His His His
    210                 215                 220

His His His
225

<210> SEQ ID NO 213
<211> LENGTH: 224
<212> TYPE: PRT
<213> ORGANISM: Artificial Sequence
<220> FEATURE:
<223> OTHER INFORMATION: Melittin-SEQ ID NO:92

<400> SEQUENCE: 213

Met Gly Ile Gly Ala Val Leu Lys Val Leu Thr Thr Gly Leu Pro Ala
 1               5                  10                  15

Leu Ile Ser Trp Ile Lys Arg Lys Arg Gln Gln Gly Ser Met Leu Ser
                20                  25                  30

Glu Lys Ser Phe Val Glu Ala Ala Ser Leu Gly Cys Glu Val Ala
            35                  40                  45

Ala Ile Lys Ala Ile Ala Ser Val Glu Thr Lys Gly Ser Ala Trp Ile
 50                 55                  60

Thr Pro Gly Val Pro Gln Ile Leu Tyr Glu Arg His Ile Met Ala Arg
 65                 70                  75                  80

Leu Leu Lys Ala Lys Gly Val Pro Ile Ala Gly Leu Pro Ser Asp Leu
                85                  90                  95

Val Asn Thr Thr Pro Gly Gly Tyr Gly Lys Phe Ser Glu Gln His Gly
               100                 105                 110

Lys Leu Asp Arg Ala Val Lys Ile Asp Arg Glu Cys Ala Leu Gln Ser
            115                 120                 125

Cys Ser Trp Gly Met Phe Gln Leu Met Gly Phe Asn Tyr Lys Leu Cys
        130                 135                 140

Gly Tyr Ala Thr Val Gln Ala Phe Val Asn Ala Met Tyr Lys Ser Glu
145                 150                 155                 160

Asp Glu Gln Leu Asn Ala Phe Val Gly Phe Ile Lys Ser Asn Leu Gln
                165                 170                 175

Leu Asn Asp Ala Leu Lys Ser Lys Asp Trp Ala Thr Val Ala Arg Leu
```

```
            180                 185                 190
Tyr Asn Gly Ala Asp Tyr Lys Ile Asn Ser Tyr Asp Gln Lys Leu Ala
        195                 200                 205

Val Ala Tyr Glu Ser Asn Lys Arg Leu Glu His His His His His His
    210                 215                 220

<210> SEQ ID NO 214
<211> LENGTH: 223
<212> TYPE: PRT
<213> ORGANISM: Artificial Sequence
<220> FEATURE:
<223> OTHER INFORMATION: Pleuricidin-SEQ ID NO:92

<400> SEQUENCE: 214

Met Gly Trp Gly Ser Phe Phe Lys Lys Ala Ala His Val Gly Lys His
1               5                   10                  15

Val Gly Lys Ala Ala Leu Thr His Tyr Leu Gly Ser Met Leu Ser Glu
            20                  25                  30

Lys Ser Phe Val Glu Ala Ala Ser Leu Gly Cys Glu Val Ala Ala
        35                  40                  45

Ile Lys Ala Ile Ala Ser Val Glu Thr Lys Gly Ser Ala Trp Ile Thr
50                  55                  60

Pro Gly Val Pro Gln Ile Leu Tyr Glu Arg His Ile Met Ala Arg Leu
65                  70                  75                  80

Leu Lys Ala Lys Gly Val Pro Ile Ala Gly Leu Pro Ser Asp Leu Val
                85                  90                  95

Asn Thr Thr Pro Gly Gly Tyr Gly Lys Phe Ser Glu Gln His Gly Lys
            100                 105                 110

Leu Asp Arg Ala Val Lys Ile Asp Arg Glu Cys Ala Leu Gln Ser Cys
        115                 120                 125

Ser Trp Gly Met Phe Gln Leu Met Gly Phe Asn Tyr Lys Leu Cys Gly
130                 135                 140

Tyr Ala Thr Val Gln Ala Phe Val Asn Ala Met Tyr Lys Ser Glu Asp
145                 150                 155                 160

Glu Gln Leu Asn Ala Phe Val Gly Phe Ile Lys Ser Asn Leu Gln Leu
                165                 170                 175

Asn Asp Ala Leu Lys Ser Lys Asp Trp Ala Thr Val Ala Arg Leu Tyr
            180                 185                 190

Asn Gly Ala Asp Tyr Lys Ile Asn Ser Tyr Asp Gln Lys Leu Ala Val
        195                 200                 205

Ala Tyr Glu Ser Asn Lys Arg Leu Glu His His His His His His
    210                 215                 220

<210> SEQ ID NO 215
<211> LENGTH: 218
<212> TYPE: PRT
<213> ORGANISM: Artificial Sequence
<220> FEATURE:
<223> OTHER INFORMATION: ECP19-SEQ ID NO:92

<400> SEQUENCE: 215

Met Gly Arg Pro Pro Gln Phe Thr Arg Ala Gln Trp Phe Ala Ile Gln
1               5                   10                  15

His Ile Ser Leu Asn Gly Ser Met Leu Ser Glu Lys Ser Phe Val Glu
            20                  25                  30

Ala Ala Ala Ser Leu Gly Cys Glu Val Ala Ala Ile Lys Ala Ile Ala
        35                  40                  45
```

```
Ser Val Glu Thr Lys Gly Ser Ala Trp Ile Thr Pro Gly Val Pro Gln
    50                  55                  60

Ile Leu Tyr Glu Arg His Ile Met Ala Arg Leu Leu Lys Ala Lys Gly
65                  70                  75                  80

Val Pro Ile Ala Gly Leu Pro Ser Asp Leu Val Asn Thr Thr Pro Gly
                85                  90                  95

Gly Tyr Gly Lys Phe Ser Glu Gln His Gly Lys Leu Asp Arg Ala Val
                100                 105                 110

Lys Ile Asp Arg Glu Cys Ala Leu Gln Ser Cys Ser Trp Gly Met Phe
            115                 120                 125

Gln Leu Met Gly Phe Asn Tyr Lys Leu Cys Gly Tyr Ala Thr Val Gln
130                 135                 140

Ala Phe Val Asn Ala Met Tyr Lys Ser Glu Asp Glu Gln Leu Asn Ala
145                 150                 155                 160

Phe Val Gly Phe Ile Lys Ser Asn Leu Gln Leu Asn Asp Ala Leu Lys
                165                 170                 175

Ser Lys Asp Trp Ala Thr Val Ala Arg Leu Tyr Asn Gly Ala Asp Tyr
            180                 185                 190

Lys Ile Asn Ser Tyr Asp Gln Lys Leu Ala Val Ala Tyr Glu Ser Asn
            195                 200                 205

Lys Arg Leu Glu His His His His His His
210                 215

<210> SEQ ID NO 216
<211> LENGTH: 221
<212> TYPE: PRT
<213> ORGANISM: Artificial Sequence
<220> FEATURE:
<223> OTHER INFORMATION: MSI-594-SEQ ID NO:92

<400> SEQUENCE: 216

Met Gly Ile Gly Lys Phe Leu Lys Lys Ala Lys Lys Gly Ile Gly Ala
1               5                   10                  15

Val Leu Lys Val Leu Thr Thr Gly Gly Ser Met Leu Ser Glu Lys Ser
                20                  25                  30

Phe Val Glu Ala Ala Ala Ser Leu Gly Cys Glu Val Ala Ala Ile Lys
            35                  40                  45

Ala Ile Ala Ser Val Glu Thr Lys Gly Ser Ala Trp Ile Thr Pro Gly
    50                  55                  60

Val Pro Gln Ile Leu Tyr Glu Arg His Ile Met Ala Arg Leu Leu Lys
65                  70                  75                  80

Ala Lys Gly Val Pro Ile Ala Gly Leu Pro Ser Asp Leu Val Asn Thr
                85                  90                  95

Thr Pro Gly Gly Tyr Gly Lys Phe Ser Glu Gln His Gly Lys Leu Asp
            100                 105                 110

Arg Ala Val Lys Ile Asp Arg Glu Cys Ala Leu Gln Ser Cys Ser Trp
        115                 120                 125

Gly Met Phe Gln Leu Met Gly Phe Asn Tyr Lys Leu Cys Gly Tyr Ala
    130                 135                 140

Thr Val Gln Ala Phe Val Asn Ala Met Tyr Lys Ser Glu Asp Glu Gln
145                 150                 155                 160

Leu Asn Ala Phe Val Gly Phe Ile Lys Ser Asn Leu Gln Leu Asn Asp
                165                 170                 175

Ala Leu Lys Ser Lys Asp Trp Ala Thr Val Ala Arg Leu Tyr Asn Gly
            180                 185                 190
```

Ala Asp Tyr Lys Ile Asn Ser Tyr Asp Gln Lys Leu Ala Val Ala Tyr
            195                 200                 205

Glu Ser Asn Lys Arg Leu Glu His His His His His
    210                 215                 220

<210> SEQ ID NO 217
<211> LENGTH: 237
<212> TYPE: PRT
<213> ORGANISM: Artificial Sequence
<220> FEATURE:
<223> OTHER INFORMATION: Sarcotoxin IA-SEQ ID NO:92

<400> SEQUENCE: 217

Met Gly Trp Leu Lys Lys Ile Gly Lys Lys Ile Glu Arg Val Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly Ser Met Leu Ser Glu Lys Ser
        35                  40                  45

Phe Val Glu Ala Ala Ala Ser Leu Gly Cys Glu Val Ala Ala Ile Lys
    50                  55                  60

Ala Ile Ala Ser Val Glu Thr Lys Gly Ser Ala Trp Ile Thr Pro Gly
65                  70                  75                  80

Val Pro Gln Ile Leu Tyr Glu Arg His Ile Met Ala Arg Leu Leu Lys
                85                  90                  95

Ala Lys Gly Val Pro Ile Ala Gly Leu Pro Ser Asp Leu Val Asn Thr
            100                 105                 110

Thr Pro Gly Gly Tyr Gly Lys Phe Ser Glu Gln His Gly Lys Leu Asp
        115                 120                 125

Arg Ala Val Lys Ile Asp Arg Glu Cys Ala Leu Gln Ser Cys Ser Trp
    130                 135                 140

Gly Met Phe Gln Leu Met Gly Phe Asn Tyr Lys Leu Cys Gly Tyr Ala
145                 150                 155                 160

Thr Val Gln Ala Phe Val Asn Ala Met Tyr Lys Ser Glu Asp Glu Gln
                165                 170                 175

Leu Asn Ala Phe Val Gly Phe Ile Lys Ser Asn Leu Gln Leu Asn Asp
            180                 185                 190

Ala Leu Lys Ser Lys Asp Trp Ala Thr Val Ala Arg Leu Tyr Asn Gly
        195                 200                 205

Ala Asp Tyr Lys Ile Asn Ser Tyr Asp Gln Lys Leu Ala Val Ala Tyr
    210                 215                 220

Glu Ser Asn Lys Arg Leu Glu His His His His His
225                 230                 235

<210> SEQ ID NO 218
<211> LENGTH: 234
<212> TYPE: PRT
<213> ORGANISM: Artificial Sequence
<220> FEATURE:
<223> OTHER INFORMATION: Cecropin A (A.aeg) - SEQ ID NO:92

<400> SEQUENCE: 218

Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
            20                  25                  30

Lys Ala Leu Arg Lys Gly Ser Met Leu Ser Glu Lys Ser Phe Val Glu
        35                  40                  45

```
Ala Ala Ala Ser Leu Gly Cys Glu Val Ala Ile Lys Ala Ile Ala
         50                  55                  60

Ser Val Glu Thr Lys Gly Ser Ala Trp Ile Thr Pro Gly Val Pro Gln
 65                  70                  75                  80

Ile Leu Tyr Glu Arg His Ile Met Ala Arg Leu Leu Lys Ala Lys Gly
                 85                  90                  95

Val Pro Ile Ala Gly Leu Pro Ser Asp Leu Val Asn Thr Thr Pro Gly
                100                 105                 110

Gly Tyr Gly Lys Phe Ser Glu Gln His Gly Lys Leu Asp Arg Ala Val
                115                 120                 125

Lys Ile Asp Arg Glu Cys Ala Leu Gln Ser Cys Ser Trp Gly Met Phe
130                 135                 140

Gln Leu Met Gly Phe Asn Tyr Lys Leu Cys Gly Tyr Ala Thr Val Gln
145                 150                 155                 160

Ala Phe Val Asn Ala Met Tyr Lys Ser Glu Asp Glu Gln Leu Asn Ala
                165                 170                 175

Phe Val Gly Phe Ile Lys Ser Asn Leu Gln Leu Asn Asp Ala Leu Lys
                180                 185                 190

Ser Lys Asp Trp Ala Thr Val Ala Arg Leu Tyr Asn Gly Ala Asp Tyr
                195                 200                 205

Lys Ile Asn Ser Tyr Asp Gln Lys Leu Ala Val Ala Tyr Glu Ser Asn
                210                 215                 220

Lys Arg Leu Glu His His His His His His
225                 230

<210> SEQ ID NO 219
<211> LENGTH: 232
<212> TYPE: PRT
<213> ORGANISM: Artificial Sequence
<220> FEATURE:
<223> OTHER INFORMATION: TL-ColM-SEQ ID NO:92

<400> SEQUENCE: 219

Met Glu Thr Leu Thr Val His Ala Pro Ser Pro Ser Thr Asn Leu Pro
 1               5                  10                  15

Ser Tyr Gly Asn Gly Ala Phe Ser Leu Ser Ala Pro His Val Pro Gly
                 20                  25                  30

Ala Gly Pro Gly Ser Met Leu Ser Glu Lys Ser Phe Val Glu Ala Ala
             35                  40                  45

Ala Ser Leu Gly Cys Glu Val Ala Ala Ile Lys Ala Ile Ala Ser Val
         50                  55                  60

Glu Thr Lys Gly Ser Ala Trp Ile Thr Pro Gly Val Pro Gln Ile Leu
 65                  70                  75                  80

Tyr Glu Arg His Ile Met Ala Arg Leu Leu Lys Ala Lys Gly Val Pro
                 85                  90                  95

Ile Ala Gly Leu Pro Ser Asp Leu Val Asn Thr Thr Pro Gly Gly Tyr
                100                 105                 110

Gly Lys Phe Ser Glu Gln His Gly Lys Leu Asp Arg Ala Val Lys Ile
            115                 120                 125

Asp Arg Glu Cys Ala Leu Gln Ser Cys Ser Trp Gly Met Phe Gln Leu
130                 135                 140

Met Gly Phe Asn Tyr Lys Leu Cys Gly Tyr Ala Thr Val Gln Ala Phe
145                 150                 155                 160

Val Asn Ala Met Tyr Lys Ser Glu Asp Glu Gln Leu Asn Ala Phe Val
                165                 170                 175
```

Gly Phe Ile Lys Ser Asn Leu Gln Leu Asn Asp Ala Leu Lys Ser Lys
                180                 185                 190

Asp Trp Ala Thr Val Ala Arg Leu Tyr Asn Gly Ala Asp Tyr Lys Ile
            195                 200                 205

Asn Ser Tyr Asp Gln Lys Leu Ala Val Ala Tyr Glu Ser Asn Lys Arg
        210                 215                 220

Leu Glu His His His His His His
225                 230

<210> SEQ ID NO 220
<211> LENGTH: 217
<212> TYPE: PRT
<213> ORGANISM: Artificial Sequence
<220> FEATURE:
<223> OTHER INFORMATION: SEQ ID NO:92-SBO

<400> SEQUENCE: 220

Met Gly Leu Ser Glu Lys Ser Phe Val Glu Ala Ala Ser Leu Gly
1               5                   10                  15

Cys Glu Val Ala Ala Ile Lys Ala Ile Ala Ser Val Glu Thr Lys Gly
                20                  25                  30

Ser Ala Trp Ile Thr Pro Gly Val Pro Gln Ile Leu Tyr Glu Arg His
            35                  40                  45

Ile Met Ala Arg Leu Leu Lys Ala Lys Gly Val Pro Ile Ala Gly Leu
        50                  55                  60

Pro Ser Asp Leu Val Asn Thr Thr Pro Gly Gly Tyr Gly Lys Phe Ser
65                  70                  75                  80

Glu Gln His Gly Lys Leu Asp Arg Ala Val Lys Ile Asp Arg Glu Cys
                85                  90                  95

Ala Leu Gln Ser Cys Ser Trp Gly Met Phe Gln Leu Met Gly Phe Asn
            100                 105                 110

Tyr Lys Leu Cys Gly Tyr Ala Thr Val Gln Ala Phe Val Asn Ala Met
        115                 120                 125

Tyr Lys Ser Glu Asp Glu Gln Leu Asn Ala Phe Val Gly Phe Ile Lys
    130                 135                 140

Ser Asn Leu Gln Leu Asn Asp Ala Leu Lys Ser Lys Asp Trp Ala Thr
145                 150                 155                 160

Val Ala Arg Leu Tyr Asn Gly Ala Asp Tyr Lys Ile Asn Ser Tyr Asp
                165                 170                 175

Gln Lys Leu Ala Val Ala Tyr Glu Ser Asn Lys Arg His His His His
            180                 185                 190

His His Leu Lys Met Lys Leu Lys Lys Ile Ala Gln Lys Ile Lys Asn
        195                 200                 205

Phe Phe Ala Lys Leu Val Ala Leu Glu
    210                 215

<210> SEQ ID NO 221
<211> LENGTH: 215
<212> TYPE: PRT
<213> ORGANISM: Artificial Sequence
<220> FEATURE:
<223> OTHER INFORMATION: SEQ ID NO:92-Apidaecin

<400> SEQUENCE: 221

Met Gly Leu Ser Glu Lys Ser Phe Val Glu Ala Ala Ser Leu Gly
1               5                   10                  15

Cys Glu Val Ala Ala Ile Lys Ala Ile Ala Ser Val Glu Thr Lys Gly

-continued

```
                20                  25                  30
Ser Ala Trp Ile Thr Pro Gly Val Pro Gln Ile Leu Tyr Glu Arg His
        35                  40                  45
Ile Met Ala Arg Leu Leu Lys Ala Lys Gly Val Pro Ile Ala Gly Leu
    50                  55                  60
Pro Ser Asp Leu Val Asn Thr Thr Pro Gly Gly Tyr Gly Lys Phe Ser
65                  70                  75                  80
Glu Gln His Gly Lys Leu Asp Arg Ala Val Lys Ile Asp Arg Glu Cys
                85                  90                  95
Ala Leu Gln Ser Cys Ser Trp Gly Met Phe Gln Leu Met Gly Phe Asn
            100                 105                 110
Tyr Lys Leu Cys Gly Tyr Ala Thr Val Gln Ala Phe Val Asn Ala Met
            115                 120                 125
Tyr Lys Ser Glu Asp Glu Gln Leu Asn Ala Phe Val Gly Phe Ile Lys
            130                 135                 140
Ser Asn Leu Gln Leu Asn Asp Ala Leu Lys Ser Lys Asp Trp Ala Thr
145                 150                 155                 160
Val Ala Arg Leu Tyr Asn Gly Ala Asp Tyr Lys Ile Asn Ser Tyr Asp
                165                 170                 175
Gln Lys Leu Ala Val Ala Tyr Glu Ser Asn Lys Arg His His His His
            180                 185                 190
His His Leu Lys Ala Asn Arg Pro Val Tyr Ile Pro Pro Arg Pro
            195                 200                 205
Pro His Pro Arg Leu Leu Glu
        210                 215
```

<210> SEQ ID NO 222
<211> LENGTH: 224
<212> TYPE: PRT
<213> ORGANISM: Artificial Sequence
<220> FEATURE:
<223> OTHER INFORMATION: SEQ ID NO:92-Melittin

<400> SEQUENCE: 222

```
Met Gly Leu Ser Glu Lys Ser Phe Val Glu Ala Ala Ala Ser Leu Gly
1               5                   10                  15
Cys Glu Val Ala Ala Ile Lys Ala Ile Ala Ser Val Glu Thr Lys Gly
                20                  25                  30
Ser Ala Trp Ile Thr Pro Gly Val Pro Gln Ile Leu Tyr Glu Arg His
        35                  40                  45
Ile Met Ala Arg Leu Leu Lys Ala Lys Gly Val Pro Ile Ala Gly Leu
    50                  55                  60
Pro Ser Asp Leu Val Asn Thr Thr Pro Gly Gly Tyr Gly Lys Phe Ser
65                  70                  75                  80
Glu Gln His Gly Lys Leu Asp Arg Ala Val Lys Ile Asp Arg Glu Cys
                85                  90                  95
Ala Leu Gln Ser Cys Ser Trp Gly Met Phe Gln Leu Met Gly Phe Asn
            100                 105                 110
Tyr Lys Leu Cys Gly Tyr Ala Thr Val Gln Ala Phe Val Asn Ala Met
            115                 120                 125
Tyr Lys Ser Glu Asp Glu Gln Leu Asn Ala Phe Val Gly Phe Ile Lys
            130                 135                 140
Ser Asn Leu Gln Leu Asn Asp Ala Leu Lys Ser Lys Asp Trp Ala Thr
145                 150                 155                 160
Val Ala Arg Leu Tyr Asn Gly Ala Asp Tyr Lys Ile Asn Ser Tyr Asp
```

165                 170                 175
Gln Lys Leu Ala Val Ala Tyr Glu Ser Asn Lys Arg His His His
            180                 185                 190

His His Leu Lys Gly Ile Gly Ala Val Leu Lys Val Leu Thr Thr Gly
        195                 200                 205

Leu Pro Ala Leu Ile Ser Trp Ile Lys Arg Lys Arg Gln Gln Leu Glu
    210                 215                 220

<210> SEQ ID NO 223
<211> LENGTH: 210
<212> TYPE: PRT
<213> ORGANISM: Artificial Sequence
<220> FEATURE:
<223> OTHER INFORMATION: SEQ ID NO:92-Indolicidin

<400> SEQUENCE: 223

Met Leu Ser Glu Lys Ser Phe Val Glu Ala Ala Ser Leu Gly Cys
1               5                   10                  15

Glu Val Ala Ala Ile Lys Ala Ile Ala Ser Val Glu Thr Lys Gly Ser
            20                  25                  30

Ala Trp Ile Thr Pro Gly Val Pro Gln Ile Leu Tyr Glu Arg His Ile
        35                  40                  45

Met Ala Arg Leu Leu Lys Ala Lys Gly Val Pro Ile Ala Gly Leu Pro
    50                  55                  60

Ser Asp Leu Val Asn Thr Thr Pro Gly Gly Tyr Gly Lys Phe Ser Glu
65                  70                  75                  80

Gln His Gly Lys Leu Asp Arg Ala Val Lys Ile Asp Arg Glu Cys Ala
                85                  90                  95

Leu Gln Ser Cys Ser Trp Gly Met Phe Gln Leu Met Gly Phe Asn Tyr
            100                 105                 110

Lys Leu Cys Gly Tyr Ala Thr Val Gln Ala Phe Val Asn Ala Met Tyr
        115                 120                 125

Lys Ser Glu Asp Glu Gln Leu Asn Ala Phe Val Gly Phe Ile Lys Ser
    130                 135                 140

Asn Leu Gln Leu Asn Asp Ala Leu Lys Ser Lys Asp Trp Ala Thr Val
145                 150                 155                 160

Ala Arg Leu Tyr Asn Gly Ala Asp Tyr Lys Ile Asn Ser Tyr Asp Gln
                165                 170                 175

Lys Leu Ala Val Ala Tyr Glu Ser Asn Lys Arg Leu Lys Ile Leu Pro
            180                 185                 190

Trp Lys Trp Pro Trp Trp Pro Trp Arg Arg Leu Glu His His His
        195                 200                 205

His His
    210

<210> SEQ ID NO 224
<211> LENGTH: 218
<212> TYPE: PRT
<213> ORGANISM: Artificial Sequence
<220> FEATURE:
<223> OTHER INFORMATION: SEQ ID NO:92-Pyrrhocoricin

<400> SEQUENCE: 224

Met Gly Leu Ser Glu Lys Ser Phe Val Glu Ala Ala Ser Leu Gly
1               5                   10                  15

Cys Glu Val Ala Ala Ile Lys Ala Ile Ala Ser Val Glu Thr Lys Gly
            20                  25                  30

```
Ser Ala Trp Ile Thr Pro Gly Val Pro Gln Ile Leu Tyr Glu Arg His
            35                  40                  45

Ile Met Ala Arg Leu Leu Lys Ala Lys Gly Val Pro Ile Ala Gly Leu
 50                  55                  60

Pro Ser Asp Leu Val Asn Thr Thr Pro Gly Gly Tyr Gly Lys Phe Ser
 65                  70                  75                  80

Glu Gln His Gly Lys Leu Asp Arg Ala Val Lys Ile Asp Arg Glu Cys
                85                  90                  95

Ala Leu Gln Ser Cys Ser Trp Gly Met Phe Gln Leu Met Gly Phe Asn
                100                 105                 110

Tyr Lys Leu Cys Gly Tyr Ala Thr Val Gln Ala Phe Val Asn Ala Met
                115                 120                 125

Tyr Lys Ser Glu Asp Glu Gln Leu Asn Ala Phe Val Gly Phe Ile Lys
            130                 135                 140

Ser Asn Leu Gln Leu Asn Asp Ala Leu Lys Ser Lys Asp Trp Ala Thr
145                 150                 155                 160

Val Ala Arg Leu Tyr Asn Gly Ala Asp Tyr Lys Ile Asn Ser Tyr Asp
                165                 170                 175

Gln Lys Leu Ala Val Ala Tyr Glu Ser Asn Lys Arg His His His His
                180                 185                 190

His His Leu Lys Val Asp Lys Gly Ser Tyr Leu Pro Arg Pro Thr Pro
            195                 200                 205

Pro Arg Pro Ile Tyr Asn Arg Asn Leu Glu
            210                 215

<210> SEQ ID NO 225
<211> LENGTH: 299
<212> TYPE: PRT
<213> ORGANISM: Artificial Sequence
<220> FEATURE:
<223> OTHER INFORMATION: SMAP29+KZ144

<400> SEQUENCE: 225

Met Arg Gly Leu Arg Arg Leu Gly Arg Lys Ile Ala His Gly Val Lys
 1               5                  10                  15

Lys Tyr Gly Pro Thr Val Leu Arg Ile Ile Arg Ile Ala Gly Gly Ser
                20                  25                  30

Lys Val Leu Arg Lys Gly Asp Arg Gly Asp Glu Val Ser Gln Leu Gln
            35                  40                  45

Thr Leu Leu Asn Leu Ser Gly Tyr Asp Val Gly Lys Pro Asp Gly Ile
 50                  55                  60

Phe Gly Asn Asn Thr Phe Asn Gln Val Val Lys Phe Gln Lys Asp Asn
 65                  70                  75                  80

Ser Leu Asp Ser Asp Gly Ile Val Gly Lys Asn Thr Trp Ala Glu Leu
                85                  90                  95

Phe Ser Lys Tyr Ser Pro Ile Pro Tyr Lys Thr Ile Pro Met Pro
                100                 105                 110

Thr Ala Asn Lys Ser Arg Ala Ala Ala Thr Pro Val Met Asn Ala Val
            115                 120                 125

Glu Asn Ala Thr Gly Val Arg Ser Gln Leu Leu Leu Thr Phe Ala Ser
            130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                165                 170                 175
```

```
Asn Tyr Gly Met Lys Tyr Gly Val Leu Thr Asp Pro Thr Gly Ala Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
    210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys Leu Glu His His His His His His
            290                 295

<210> SEQ ID NO 226
<211> LENGTH: 260
<212> TYPE: PRT
<213> ORGANISM: Unknown
<220> FEATURE:
<223> OTHER INFORMATION: phiKZgp144

<400> SEQUENCE: 226

Met Lys Val Leu Arg Lys Gly Asp Arg Gly Asp Glu Val Cys Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Cys Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Thr Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Ile Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Met Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Ala Ala Arg
        195                 200                 205

Arg Phe Leu Thr Thr Gly Gln Asn Glu Leu Ala Ala Thr His Phe Pro
    210                 215                 220

Lys Glu Ala Gln Ala Asn Pro Ser Ile Phe Tyr Asn Lys Asp Gly Ser
225                 230                 235                 240
```

-continued

```
Pro Lys Thr Ile Gln Glu Val Tyr Asn Leu Met Asp Gly Lys Val Ala
            245                 250                 255
Ala His Arg Lys
        260

<210> SEQ ID NO 227
<211> LENGTH: 260
<212> TYPE: PRT
<213> ORGANISM: Unknown
<220> FEATURE:
<223> OTHER INFORMATION: OBPgpLYS

<400> SEQUENCE: 227

Met Lys Val Leu Arg Lys Gly Asp Arg Gly Asp Glu Val Cys Gln Leu
1               5                   10                  15
Gln Thr Leu Leu Asn Leu Cys Gly Tyr Asp Val Gly Lys Pro Asp Gly
            20                  25                  30
Ile Phe Gly Asn Asn Thr Phe Asn Gln Val Val Lys Phe Gln Lys Asp
        35                  40                  45
Asn Cys Leu Asp Ser Asp Gly Ile Val Gly Lys Asn Thr Trp Ala Glu
    50                  55                  60
Leu Phe Ser Lys Tyr Ser Pro Pro Ile Pro Tyr Lys Thr Ile Pro Met
65                  70                  75                  80
Pro Thr Ala Asn Lys Ser Arg Ala Ala Ala Thr Pro Val Met Asn Ala
                85                  90                  95
Val Glu Asn Ala Thr Gly Val Arg Ser Gln Leu Leu Leu Thr Phe Ala
            100                 105                 110
Ser Ile Glu Ser Ala Phe Asp Tyr Glu Ile Lys Ala Lys Thr Ser Ser
        115                 120                 125
Ala Thr Gly Trp Phe Gln Phe Leu Thr Gly Thr Trp Lys Thr Met Ile
    130                 135                 140
Glu Asn Tyr Gly Met Lys Tyr Gly Val Leu Thr Asp Pro Thr Gly Ala
145                 150                 155                 160
Leu Arg Lys Asp Pro Arg Ile Ser Ala Leu Met Gly Ala Glu Leu Ile
                165                 170                 175
Lys Glu Asn Met Asn Ile Leu Arg Pro Val Leu Lys Arg Glu Pro Thr
            180                 185                 190
Asp Thr Asp Leu Tyr Leu Ala His Phe Phe Gly Pro Gly Ala Ala Arg
        195                 200                 205
Arg Phe Leu Thr Thr Gly Gln Asn Glu Leu Ala Ala Thr His Phe Pro
    210                 215                 220
Lys Glu Ala Gln Ala Asn Pro Ser Ile Phe Tyr Asn Lys Asp Gly Ser
225                 230                 235                 240
Pro Lys Thr Ile Gln Glu Val Tyr Asn Leu Met Asp Gly Lys Val Ala
                245                 250                 255
Ala His Arg Lys
            260

<210> SEQ ID NO 228
<211> LENGTH: 235
<212> TYPE: PRT
<213> ORGANISM: Unknown
<220> FEATURE:
<223> OTHER INFORMATION: wt PVPSE1gp146

<400> SEQUENCE: 228

Met Asn Ala Ala Ile Ala Glu Ile Gln Arg Met Leu Ile Glu Gly Gly
1               5                   10                  15
```

-continued

```
Phe Ser Val Gly Lys Ser Gly Ala Asp Gly Leu Tyr Gly Pro Ala Thr
         20              25              30
Lys Ala Ala Leu Gln Lys Cys Ile Ala Gln Ala Thr Ser Gly Asn Asn
             35              40              45
Lys Gly Gly Thr Leu Lys Leu Thr Gln Ala Gln Leu Asp Lys Ile Phe
         50              55              60
Pro Val Gly Ala Ser Ser Gly Arg Asn Ala Lys Leu Lys Pro Leu Asn
65              70              75              80
Asp Leu Phe Glu Lys Thr Glu Ile Asn Thr Val Asn Arg Val Ala Gly
                 85              90              95
Phe Leu Ser Gln Ile Gly Val Glu Ser Ala Glu Phe Arg Tyr Val Arg
             100             105             110
Glu Leu Gly Asn Asp Ala Tyr Phe Asp Lys Tyr Asp Thr Gly Pro Ile
         115             120             125
Ala Glu Arg Leu Gly Asn Thr Pro Gln Lys Asp Gly Asp Gly Ala Lys
         130             135             140
Tyr Lys Gly Arg Gly Leu Ile Gln Val Thr Gly Leu Ala Asn Tyr Lys
145             150             155             160
Ala Cys Gly Lys Ala Leu Gly Leu Asp Leu Val Asn His Pro Glu Leu
                 165             170             175
Leu Glu Gln Pro Glu Tyr Ala Val Ala Ser Ala Gly Trp Tyr Trp Asp
             180             185             190
Thr Arg Asn Ile Asn Ala Ala Cys Asp Ala Asp Asp Ile Val Lys Ile
             195             200             205
Thr Lys Leu Val Asn Gly Gly Thr Asn His Leu Ala Glu Arg Thr Ala
         210             215             220
Tyr Tyr Lys Lys Ala Lys Ser Val Leu Thr Ser
225             230             235
```